US006902924B2

(12) United States Patent
Turner, Jr. et al.

(10) Patent No.: US 6,902,924 B2
(45) Date of Patent: Jun. 7, 2005

(54) HUMAN KINASES AND POLYNUCLEOTIDES ENCODING THE SAME

(75) Inventors: C. Alexander Turner, Jr., The Woodlands, TX (US); Brian Mathur, The Woodlands, TX (US); Carl Johan Friddle, The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 125 days.

(21) Appl. No.: 10/413,437

(22) Filed: Apr. 11, 2003

(65) Prior Publication Data

US 2003/0225257 A1 Dec. 4, 2003

Related U.S. Application Data

(63) Continuation of application No. 10/020,079, filed on Dec. 12, 2001, now Pat. No. 6,579,710.

(60) Provisional application No. 60/255,103, filed on Dec. 12, 2000, and provisional application No. 60/289,422, filed on May 8, 2001.

(51) Int. Cl.[7] .......................... C12N 1/20; C12N 9/20; C12N 15/00; C12N 5/00; C07H 21/04

(52) U.S. Cl. ................ 435/252.3; 435/194; 435/320.1; 435/325; 435/6; 536/23.2

(58) Field of Search .......................... 435/252.3, 320.1, 435/325, 6, 194; 536/23.2

(56) References Cited

U.S. PATENT DOCUMENTS 4,215,051 A 7/1980 Schroeder et al.
4,376,110 A 3/1983 David et al.
4,594,595 A 6/1986 Struckman
4,631,211 A 12/1986 Houghten
4,689,405 A 8/1987 Frank et al.
4,713,326 A 12/1987 Dattagupta et al.
4,873,191 A 10/1989 Wagner et al.
4,946,778 A 8/1990 Ladner et al.
5,252,743 A 10/1993 Barrett et al.
5,272,057 A 12/1993 Smulson et al.
5,424,186 A 6/1995 Fodor et al.
5,445,934 A 8/1995 Fodor et al.
5,459,127 A 10/1995 Felgner et al.
5,556,752 A 9/1996 Lockhart et al.
5,700,637 A 12/1997 Southern
5,723,323 A 3/1998 Kauffman et al.
5,744,305 A 4/1998 Fodor et al.
5,830,721 A 11/1998 Stemmer et al.
5,837,458 A 11/1998 Minshull et al.
5,869,336 A 2/1999 Meyer et al.
5,877,397 A 3/1999 Lonberg et al.
5,948,767 A 9/1999 Scheule et al.
6,075,181 A 6/2000 Kucherlapati et al.
6,110,490 A 8/2000 Thierry
6,117,679 A 9/2000 Stemmer
6,150,584 A 11/2000 Kucherlapati et al.

FOREIGN PATENT DOCUMENTS

WO WO 00/73469 A2 12/2000

OTHER PUBLICATIONS

Bird et al, 1988, "Single–Chain Antigen–Binding Proteins", Science 242:423–426.

Bitter et al, 1987, "Expression and Secretion Vectors for Yeast", Methods in Enzymology 153:516–544.

Colbere–Garapin et al, 1981, "A New Dominant Hybrid Selective Marker for Higher Eukaryotic Cells", J. Mol. Biol. 150:1–14.

Gautier et al, 1987, "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.

Gordon, 1989, "Transgenic Animals", International Review of Cytology, 115:171–229.

Greenspan et al, 1993, "Idiotypes: structure and immunogenicity", FASEB Journal 7:437–444.

Gu et al, 1994, "Deletion of DNA Polymerase β Gene Segment in T Cells Using Cell Type–Specific Gene Targeting", Science 265:103–106.

Huse et al, 1989, "Generation of a Large Combinatorial Library of the Immunoglobulin Repertoire in Phage Lambda", Science 246:1275–1281.

Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.

Inoue et al, 1987, "Sequence–dependent hydrolysis of RNA using modified oligonucleotide splints and R Nase H", FEBS Letters 215(2):327–330.

Inoue et al, 1987, "Synthesis and hybridization studies on two complementary nona(2'–O–methyl)ribonucleotides", Nucleic Acids Research 15(15):6131–6149.

Inouye & Inouye, 1985, "Up–promoter mutations in the lpp gene of *Escherichia coli*", Nucleic Acids Research 13(9):3101–3110.

Janknecht et al, 1991, "Rapid and efficient purification of native histidine–tagged protein expressed by recombinant vaccinia virus", PNAS 88:8972–8976.

Kohler & Milstein, 1975, "Continuous cultures of fused cells secreting antibody of predefined specificity", Nature 256:495–497.

Lakso et al, 1992, "Targeted oncogene activation by site–specific recombination in transgenic mice", Proc. Natl. Acad. Sci. USA 89:6232–6236.

Lavitrano et al, 1989, "Sperm Cells as Vectors for Introducing Foreign DNA into Eggs: Genetic Transformation of Mice", Cell 57:717–723.

(Continued)

*Primary Examiner*—Maryam Monshipouri

(57) ABSTRACT

Novel human polynucleotide and polypeptide sequences are disclosed that can be used in therapeutic, diagnostic, and pharmacogenomic applications.

6 Claims, No Drawings

OTHER PUBLICATIONS

Lo, 1983, "Transformation by Iontophoretic Microinjection of DNA: Multiple Integrations without Tandem Insertions", Mol. & Cell. Biology 3(10):1803–1814.

Logan et al, 1984, "Adenovirus tripartite leader sequence enhances translation of mRNAs late after infection", Proc. Natl. Acad. Sci. USA 81:3655–3659.

Lowy et al, 1980, "Isolation of Transforming DNA: Cloning the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli* gene coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expresssing a prokaryotic dihydrofolate reductase", Proc. Natl. Acad. Sci. USA 78(3):1527–1531.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the *Autographa califomica* Nuclear Polyhedrosis Virus Genome: Deletion Mutations within the Polyhedrin Gene", J. Virol. 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Thompson et al, 1989, "Germ Line Transmission and Expression of a Corrected HPRT Gene Produced by Gene Targeting in Embryonic Stem Cells", Cell 56:313–321.

Van Der Putten et al, 1985, "Efficient insertion of genes into the mouse germ line via retroviral vectors", Proc. Natl. Acad. Sci. USA 82:6148–6152.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci. USA 77(6):3567–3570.

Database EBI 'Online' EMBL, Hinxton, Cambridgeshire, UK; May 10, 2001, Ohara et al., "Homo sapiens mRNA for KIAA1855 protein, partial cds." Database accession No. AB058758, XP002211382, abstract.

Database EBI 'Online' EMBL, Hinxton, Cambridgeshire, UK; Sep. 29, 2000, Sugano et al., "Homo sapiens cDNA: FLJ22032 is, clone HEP08743," Database accession No. AK025685, XP002211383, abstract.

Database EBI 'Online', EMBL, Hinxton, Cambridgeshire, UK, Mar. 23, 2000, Birren et al., "Homo sapiens clone RP11–117C11, working draft sequence, 36 unordered pieces," Database accession No. AC026532, XP002211384, abstract.

Database EBI 'Online', EMBL, Hinxton, Cambridgeshire, UK, Dec. 8, 1999, Skuce, C., "Human DNA sequence from clon RP3–330M21 on chromosome 6," Database accession No. AL133375, XP002211385, abstract.

Hanks, S.K., et al, "Protein Kinase Catalytic Domain Sequence Database: Identification of Conserved Features of Primary Structure and Classification of Family Members," Melk–Systeme Bou–Matic, Oldenburg, DE, vol. 200, 1991, pp. 38–62, XP000563379.

Hanks, S.K., et al., "The Protein Kinase Family: Conserved Features and Deduced Phylogeny of the Catalytic Domains," Science, American Association for the Advancement of Science, US., vol. 241, No. 4861, Jul. 1, 1988, pp. 42–52, XP000613735, ISSN: 0036–8075.

Hanks, S.K., et al., "The Eukaryotic Protein Kinase Superfamily: Kinase (Catalytic) Domain Structure and Classification," FASEB Journal, Fed. of American Soc. for Experimental Biology, Bethesda, MD, US, No. 9, May 1995, pp. 576–596, XP001078836, ISSN: 0892–6638.

Hanks, S.K., et al., "Use of degenerate oligonucleotide probes to identify clones that encode protein kinases," Methods in Enzymology, US, vol. 200, 1991, pp. 525–532, XP001096015, ISSN: 0076–6879.

International Search Report, International Application No. PCT/US01/49068, Dec. 12, 2001.

HUMAN KINASES AND POLYNUCLEOTIDES ENCODING THE SAME

The present application is a continuation of U.S. application Ser. No. 10/020,079, filed Dec. 12, 2001, now U.S. Pat. No. 6,579,710 which issued on Jun. 17, 2003, which claims the benefit of U.S. Provisional Application Nos. 60/255,103 and 60/289,422 which were filed on Dec. 12, 2000 and May 8, 2001 and are herein incorporated by reference in their entirety.

1. INTRODUCTION

The present invention relates to the discovery, identification, and characterization of novel human polynucleotides encoding proteins sharing sequence similarity with animal kinases. The invention encompasses the described polynucleotides, host cell expression systems, the encoded proteins, fusion proteins, polypeptides and peptides, antibodies to the encoded proteins and peptides, and genetically engineered animals that either lack or over-express the disclosed genes, antagonists and agonists of the proteins, and other compounds that modulate the expression or activity of the proteins encoded by the disclosed genes, which can be used for diagnosis, drug screening, clinical trial monitoring, the treatment of diseases and disorders, and cosmetic or nutriceutical applications.

2. BACKGROUND OF THE INVENTION

Kinases mediate the phosphorylation of a wide variety of proteins and compounds in the cell. Along with phosphatases, kinases are involved in a range of regulatory pathways. Given the physiological importance of kinases, they have been subject to intense scrutiny and are proven drug targets.

3. SUMMARY OF THE INVENTION

The present invention relates to the discovery, identification, and characterization of nucleotides that encode novel human proteins and the corresponding amino acid sequences of these proteins. The novel human proteins (NHPs) described for the first time herein share structural similarity with animal kinases, including, but not limited to, serine-threonine kinases, casein kinases, calcium/calmodulin-dependent protein kinases, and mitogen activated kinases. Accordingly, the described NHPs encode novel kinases having homologues and orthologs across a range of phyla and species.

The novel human polynucleotides described herein, encode open reading frames (ORFs) encoding proteins of 870, 864, 764, 751, 654, 648, 548, 535, 895, 889, 789, 776, 982, 976, 876, 863, 957, 951, 851, and 838 amino acids in length (see respectively SEQ ID NOS: 2, 4, 6, 8, 10, 12, 14, 16, 18, 20, 22, 24, 26, 28, 30, 32, 34, 36, 38, and 40).

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and open reading frame or regulatory sequence replacement constructs) or to enhance the expression of the described NHPs (e.g., expression constructs that place the described polynucleotide under the control of a strong promoter system), and transgenic animals that express a NHP sequence, or "knock-outs" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPs. When the unique NHP sequences described in SEQ ID NOS:1–40 are "knocked-out" they provide a method of identifying phenotypic expression of the particular gene as well as a method of assigning function to previously unknown genes. In addition, animals in which the unique NHP sequences described in SEQ ID NOS:1–40 are "knocked-out" provide a unique source in which to elicit antibodies to homologous and orthologous proteins which would have been previously viewed by the immune system as "self" and therefore would have failed to elicit significant antibody responses. To these ends, gene trapped knockout ES cells have been generated in murine homologs of the described NHPs.

Additionally, the unique NHP sequences described in SEQ ID NOS:1–40 are useful for the identification of protein coding sequence and mapping a unique gene to a particular chromosome. These sequences identify actual, biologically verified, and therefore relevant, exon splice junctions as opposed to those that may have been bioinformatically predicted from genomic sequence alone. The sequences of the present invention are also useful as additional DNA markers for restriction fragment length polymorphism (RFLP) analysis, and in forensic biology.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequence of the novel human ORFs encoding the described novel human kinase proteins.

5. DETAILED DESCRIPTION OF THE INVENTION

The NHPs described for the first time herein are novel proteins that are expressed in, inter alia, human cell lines and human fetal brain, brain, pituitary, cerebellum, and fetal lung, kidney, and embryo cells. The described sequences were compiled from sequences available in GENBANK, and cDNAs generated from human brain and cerebellum mRNAs (Edge Biosystems, Gaithersburg, Md.) that were identified using primers generated from human genomic DNA.

The present invention encompasses the nucleotides presented in the Sequence Listing, host cells expressing such nucleotides, the expression products of such nucleotides, and: (a) nucleotides that encode mammalian homologs of the described genes, including the specifically described NHPs, and the NHP products; (b) nucleotides that encode one or more portions of an NHP that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal sequence is deleted; (d) nucleotides that encode chimeric fusion proteins containing all or a portion of a coding region of a NHP, or one of its domains (e.g., a receptor/ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing. As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & Sons, Inc., NY, at p. 2.10.3) and encodes a functionally equivalent expression product.

Additionally, contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. Nos. 5,837,458 or 5,723,323 both of which are herein incorporated by reference). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar to corresponding regions of SEQ ID NO:1 (as measured by BLAST sequence comparison analysis using, for example, the GCG sequence analysis package using default parameters).

The invention also includes nucleic acid molecules, preferably DNA molecules, that hybridize to, and are therefore the complements of, the described NHP encoding polynucleotides. Such hybridization conditions can be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–40 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–40, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–40 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–40.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–40 provides detailed information about transcriptional changes involved in a specific pathway, potentially leading to the identification of novel components or gene functions that manifest themselves as novel phenotypes.

Probes consisting of sequences first disclosed in SEQ ID NOS:1–40 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–40 can be utilized in microarrays or other assay formats, to screen collections of genetic material from patients who have a particular medical condition. These investigations can also be carried out using the sequences first disclosed in SEQ ID NOS:1–40 in silico and by comparing previously collected genetic databases and the disclosed sequences using computer software known to those in the art.

Thus the sequences first disclosed in SEQ ID NOS:1–40 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–40. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relative to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation and/or as antisense primers in amplification reactions of NHP gene nucleic acid sequences. With respect to NHP gene regulation, such techniques can be used to regulate biological functions. Further, such sequences can be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well-known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Spring Harbor Press, NY; and Ausubel et al., 1989, Current Protocols in Molecular Biology, Green Publishing Associates and Wiley Interscience, NY.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

For example, the present sequences can be used in restriction fragment length polymorphism (RFLP) analysis to identify specific individuals. In this technique, an individual's genomic DNA is digested with one or more restriction enzymes, and probed on a Southern blot to yield unique bands for identification (as generally described in U.S. Pat. No. 5,272,057, incorporated herein by reference). In addition, the sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). Actual base sequence information can be used for identification as an accurate alternative to patterns formed by restriction enzyme generated fragments.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from, for example, human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP sequence can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal sequence. Using these two primers, the product is then amplified via PCR, optionally cloned into a suitable vector, and subjected to DNA sequence analysis through methods well-known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, behavioral disorders, immune disorders, obesity, high blood pressure, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP sequences can then be purified and subjected to sequence analysis according to methods well-known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue may be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor, N.Y.).

Additionally, screening can be accomplished by screening with labeled NHP fusion proteins, such as, for example, alkaline phosphatase-NHP or NHP-alkaline phosphatase fusion proteins. In cases where a NHP mutation results in an expression product with altered function (e.g., as a result of a missense or a frameshift mutation), polyclonal antibodies to NHP are likely to cross-react with a corresponding mutant NHP expression product. Library clones detected via their reaction with such labeled antibodies can be purified and subjected to sequence analysis according to methods well-known in the art.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721, 5,837,458, 6,117,679, and 5,723,323 which are herein incorporated by reference in their entirety.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculovirus as described in U.S. Pat. No. 5,869, 336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP sequence under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

Where, as in the present instance, some of the described NHP peptides or polypeptides are thought to be cytoplasmic or nuclear proteins (although processed forms or fragments can be secreted or membrane associated), expression systems can be engineered that produce soluble derivatives of a NHP (corresponding to a NHP extracellular and/or intracellular domains, or truncated polypeptides lacking one or more hydrophobic domains) and/or NHP fusion protein products (especially NHP-Ig fusion proteins, i.e., fusions of a NHP domain to an IgFc), NHP antibodies, and anti-idiotypic antibodies (including Fab fragments) that can be used in therapeutic applications. Preferably, the above expression systems are engineered to allow the desired peptide or polypeptide to be recovered from the culture media.

The present invention also encompasses antibodies and anti-idiotypic antibodies (including Fab fragments), antagonists and agonists of a NHP, as well as compounds or nucleotide constructs that inhibit expression of a NHP sequence (transcription factor inhibitors, antisense and ribozyme molecules, or open reading frame sequence or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of a NHP in the body. The use of engineered host cells and/or animals can offer an advantage in that such systems allow not only for the identification of compounds that bind to the endogenous receptor/ligand of a NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP or a protein interactive therewith. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and corresponding deduced amino acid sequences of the described NHPs are presented in the Sequence Listing.

Expression analysis has provided evidence that the described NHPs can be expressed in a relatively narrow range of human tissues. In addition to serine-threonine kinases, the described NHPs also share significant similarity to a range of additional kinase families, including kinases associated with signal transduction, from a variety of phyla and species. Several polymorphisms were detected in regions of sequence common to several of the described NHPs including a C/G polymorphism at the region represented by nucleotide position number 2166 of, for example, SEQ ID NO:1 which can result in a gly or ala being present at corresponding amino acid (aa) position 729 of, for example, SEQ ID NO:2, and a C/G polymorphism at the region represented by nucleotide position number 1901 of, for example, SEQ ID NO:9 which can result in a arg or thr being present at corresponding amino acid (aa) position 634 of, for example, SEQ ID NO:10.

The gene encoding the described NHPs is apparently encoded on human chromosome 6. Accordingly, the described sequences are useful for mapping and identifying the coding regions of the human genome, and for defining exon splice junctions.

The described novel human polynucleotide sequences can be used, among other things, in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458 which are herein incorporated by reference in their entirety.

NHP gene products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate NHP transgenic animals.

Any technique known in the art may be used to introduce a NHP transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus-mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the NHP transgene in all their cells, as well as animals which carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell-type by following, for example, the teaching of Lasko et al., 1992, Proc. Natl. Acad. Sci. USA 89:6232–6236. The regulatory sequences required for such a cell-type specific activation will depend upon the particular cell-type of interest, and will be apparent to those of skill in the art.

When it is desired that a NHP transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals).

The transgene can also be selectively introduced into a particular cell-type, thus inactivating the endogenous NHP gene in only that cell-type, by following, for example, the teaching of Gu et al., 1994, Science, 265:103–106. The regulatory sequences required for such a cell-type specific inactivation will depend upon the particular cell-type of interest, and will be apparent to those of skill in the art.

Once transgenic animals have been generated, the expression of the recombinant NHP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of NHP gene-expressing tissue, may also be evaluated immunocytochemically using antibodies specific for the NHP transgene product.

5.2 NHPS and NHP Polypeptides

NHP products, polypeptides, peptide fragments, mutated, truncated, or deleted forms of the NHPs, and/or NHP fusion proteins can be prepared for a variety of uses. These uses include, but are not limited to, the generation of antibodies, as reagents in diagnostic assays, the identification of other cellular gene products related to the NHP, as reagents in assays for screening for compounds that can be used as pharmaceutical reagents useful in the therapeutic treatment of mental, biological, or medical disorders and disease.

The Sequence Listing discloses the amino acid sequences encoded by the described NHP-encoding polynucleotides. The NHPs display initiator methionines that are present in DNA sequence contexts consistent with eucaryotic translation initiation sites. The NHPs do not display consensus signal sequences which indicates that they may be cytoplasmic or possibly nuclear proteins, although they may also be secreted or membrane associated.

The NHP amino acid sequences of the invention include the amino acid sequences presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well-known, and, accordingly, each amino acid presented in the Sequence Listing, is generically representative of the well-known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and modify a NHP substrate, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent expression product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where the NHP peptide or polypeptide can exist, or has been engineered to exist, as a soluble or secreted molecule, the soluble NHP peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well-known to those skilled in the art. However, such engineered host cells themselves may be used in situations where it is important not only to retain the structural and functional characteristics of the NHP, but to assess biological activity, e.g., in certain drug screening assays.

The expression systems that may be used for purposes of the invention include, but are not limited to, microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., *Saccharomyces, Pichia*) transformed with recombinant yeast expression vectors containing NHP nucleotide sequences; insect cell systems infected with recombinant virus expression vectors (e.g., baculovirus) containing NHP nucleotide sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing NHP nucleotide sequences and promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target expression product can be released from the GST moiety.

In an insect system, *Autographa californica* nuclear polyhedrosis virus (AcNPV) is used as a vector to express foreign polynucleotide sequences. The virus grows in *Spodoptera frugiperda* cells. A NHP coding sequence can be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the expression product in the specific fashion desired. Such modifications (e.g., glycosylation) and processing (e.g., cleavage) of protein products may be important for the function of the protein. Different host cells have characteristic and specific mechanisms for the post-translational processing and modification of proteins and expression products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the expression product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines that stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler et al., 1977, Cell 11:223), hypoxanthine-guanine phosphoribosyltransferase (Szybalska and Szybalski, 1962, Proc. Natl. Acad. Sci. USA 48:2026), and adenine phosphoribosyltransferase (Lowy et al., 1980, Cell 22:817) genes, which can be employed in $tk^-$, $hgprt^-$ or $aprt^-$ cells, respectively. Also, antimetabolite resistance can be used as the basis of selection for the following genes: dhfr, which confers resistance to methotrexate (Wigler et al., 1980, Proc. Natl. Acad. Sci. USA 77:3567; O'Hare et al., 1981, Proc. Natl. Acad. Sci. USA 78:1527); gpt, which confers resistance to mycophenolic acid (Mulligan and Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the sequence of interest is subcloned into a vaccinia recombination plasmid such that the sequence's open reading frame is translationally fused to an amino-terminal tag consisting of six histidine residues. Extracts from cells infected with recombinant vaccinia virus are loaded onto $Ni^{2+}$.nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in "Liposomes: A Practical Approach", New, R.R.C., ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NHP to the target site or desired organ, where they cross the cell membrane and/or the nucleus where the NHP can exert its functional activity. This goal may be achieved by coupling of the NHP to a cytokine or other ligand that provides targeting specificity, and/or to a protein transducing domain (see generally U.S. application Ser. Nos. 60/111,701 and 60/056,713, both of which are herein incorporated by reference, for examples of such transducing sequences) to facilitate passage across cellular membranes and can optionally be engineered to include nuclear localization.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention can be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP expression product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, a NHP peptide (e.g., one corresponding to a functional domain of a NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including, but not limited to, Freund's adjuvant (complete and incomplete), mineral salts such as aluminum hydroxide or aluminum phosphate, chitosan, surface active substances such as lysolecithin, pluronic polyols, polyanions, peptides, oil emulsions, and potentially useful human adjuvants such as BCG (bacille Calmette-Guerin) and *Corynebacterium parvum.* Alternatively, the immune response could be enhanced by combination and or coupling with molecules such as keyhole limpet hemocyanin, tetanus toxoid, diphtheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety. Also encompassed by the present invention is the use of fully humanized monoclonal antibodies as described in U.S. Pat. No. 6,150, 584 and respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP expression products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well-known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor/ligand can be used to generate anti-idiotypes that "mimic" the NHP and, therefore, bind, activate, or neutralize a NHP, NHP receptor, or NHP ligand. Such anti-idiotypic antibodies or Fab fragments of such anti-idiotypes can be used in therapeutic regimens involving a NHP-mediated pathway.

Additionally given the high, degree of relatedness of mammalian NHPs, the presently described knock-out mice (having never seen NHP, and thus never been tolerized to NHP) have a unique utility, as they can be advantageously applied to the generation of antibodies against the disclosed mammalian NHP (i.e., NHP will be immunogenic in NHP knock-out animals).

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising a nucleotide sequence encoding the amino acid sequence shown in SEQ ID NO:8.

2. An isolated nucleic acid molecule of claim 1 wherein said nucleotide sequence is that shown in SEQ ID NO:7.

3. A recombinant expression vector comprising a nucleotide sequence encoding the amino acid sequence shown in SEQ ID NO:8.

4. The recombinant expression vector of claim 3 wherein said nucleotide sequence is that shown in SEQ ID NO:7.

5. A host cell comprising the vector of claim 3.

6. A host cell comprising the vector of claim 4.

* * * * *

SEQUENCE LISTING

<160> NUMBER OF SEQ ID NOS: 40

<210> SEQ ID NO 1
<211> LENGTH: 2613
<212> TYPE: DNA
<213> ORGANISM: homo sapiens

<400> SEQUENCE: 1
atgtcagggc tggtgctgat gctggcggcg cggtgcattg tgggcagctc cccgctctgc 60
cgctgccgcc gccgtcgccc aaggaggatc ggggccgggc cgggccggga tgatccgggt 120
cggaaggccg ccgccgccgg agggagcggg tcacccaacg ccgcactgag ccgccccccgc 180 cccgccccgg ccccgggggga tgcgccgccc cgagctgctg cctccgccgc cgccgcagcc 240
gcagccgcag cgggcacaga gcaggtagat ggccccctca gggcaggccc ggcggacacc 300
cctccctctg gctggcggat gcagtgccta gcggccgccc ttaaggacga aaccaacatg 360
agtgggggag gggagcaggc cgacatcctg ccggccaact acgtggtcaa ggatcgctgg 420
aaggtgctga aaaagatcgg gggcgggggc tttggtgaga tctacgaggc catggacctg 480
ctgaccaggg agaatgtggc cctcaaggtg gagtcagccc agcagcccaa gcaggtcctc 540
aagatggagg tggccgtgct caagaagttg caagggaagg accatgtgtg caggttcatt 600
ggctgtggca ggaacgagaa gtttaactat gtagtgatgc agctccaggg ccggaacctg 660
gccgacctgc gccgtagcca gccgcgaggc accttcacgc tgagcaccac attgcggctg 720
ggcaagcaga tcttggagtc catcgaggcc atccactctg tgggcttcct gcaccgtgac 780
atcaagcctt caaactttgc catgggcagg ctgccctcca cctacaggaa gtgctatatg 840
ctggacttcg ggctggcccg gcagtacacc aacaccacgg gggatgtgcg gccccctcgg 900
aatgtggccg ggtttcgagg aacggttcgc tatgcctcag tcaatgccca caagaaccgg 960
gagatgggcc gccacgacga cctgtggtcc ctcttctaca tgctggtgga gtttgcagtg 1020
ggccagctgc cctggaggaa gatcaaggac aaggaacagg tagggatgat caaggagaag 1080
tatgagcacc ggatgctgct gaagcacatg ccgtcagagt tccacctctt cctggaccac 1140
attgccagcc tcgactactt caccaagccc gactaccagt tgatcatgtc agtgtttgag 1200
aacagcatga aggagagggg cattgccgag aatgaggcct ttgactggga gaaggcaggc 1260
accgatgccc tcctgtccac gagcacctct accccgcccc agcagaacac ccggcagacg 1320
gcagccatgt ttggggtggt caatgtgacg ccagtgcctg gggacctgct ccgggagaac 1380
accgaggatg tgctacaggg agagcacctg agtgaccagg agaatgcacc cccaattctg 1440
cccgggaggc cctctgaggg gctgggcccc agtccccacc ttgtccccca ccccgggggt 1500
cctgaggctg aagtctggga ggagacagat gtcaaccgga acaaactccg gatcaacatc 1560
ggcaaaagcc cctgtgtgga ggaggaacag agccgaggca tgggggtccc cagctcccca 1620

-continued

```
gtgcgtgccc ccccagactc ccccacaacc ccagtccgtt ctctgcgcta ccggagggtg   1680

aacagccctg agtcagaaag gctgtccacg gcggacgggc gagtggagct acctgagagg   1740

aggtcacgga tggatctgcc tggctcgccc tcgcgccagg cctgctcctc tcagccagcc   1800

cagatgctgt cagtggacac aggccacgct gaccgacagg ccagtggccg catggaygtg   1860

tcagcctctg tggagcagga ggccctgagc aacgccttcc gctcggtgcc gctggctgag   1920

gaggaggatt tcgacagcaa agagtgggtc atcatcgaca aggagacgga gctcaaggac   1980

ttccctccag ggctgagcc cagcacatcg ggcaccacgg atgaggagcc cgaggagctg    2040

cggccactgc ccgaggaggg cgaagagcgg cggcggctgg gggcagagcc caccgtccgg   2100

ccccggggac gcagcatgca ggcgctggcg gaggaggacc tgcagcattt gccgccccag   2160

cccctgccac cccagctgag ccaggscgat ggccgttccg agacgtcaca gccccccacg   2220

cctggcagcc cttcccactc accccctgcac tcgggacccc gccctcgacg gagagagtcg  2280

gaccccacag gcccacagag acagttggag gaggacagac tctcggggca ctccctcccg   2340

cggtacagcc ccctgcgacg actggcgtcc tccgtgttct cctcctccac gctggagacg   2400

gagcattacc ctcaccccgg cggcggcggc tcctcgggct cctccggttc cctcattcag   2460

cgcagccgct cggctgagag cagccctgtg cgggcgcccc accggcgcca cgcgcccctc   2520

gctgctggca accacagact catgccctcg gtgctccgca tctcgcggtc ccagctgcag   2580

caggtgtggg cccggttcac ccacaagacc tag                                2613
```

<210> SEQ ID NO 2
<211> LENGTH: 870
<212> TYPE: PRT
<213> ORGANISM: homo sapiens
<220> FEATURE:
<221> NAME/KEY: VARIANT
<222> LOCATION: (1)...(870)
<223> OTHER INFORMATION: Xaa = Any Amino Acid

<400> SEQUENCE: 2

```
Met Ser Gly Leu Val Leu Met Leu Ala Ala Arg Cys Ile Val Gly Ser
 1               5                  10                  15

Ser Pro Leu Cys Arg Cys Arg Arg Arg Arg Pro Arg Arg Ile Gly Ala
            20                  25                  30

Gly Pro Gly Arg Asp Asp Pro Gly Arg Lys Ala Ala Ala Ala Gly Gly
        35                  40                  45

Ser Gly Ser Pro Asn Ala Ala Leu Ser Arg Pro Arg Pro Ala Pro Ala
    50                  55                  60

Pro Gly Asp Ala Pro Pro Arg Ala Ala Ala Ser Ala Ala Ala Ala Ala
65                  70                  75                  80

Ala Ala Ala Ala Gly Thr Glu Gln Val Asp Gly Pro Leu Arg Ala Gly
                85                  90                  95

Pro Ala Asp Thr Pro Pro Ser Gly Trp Arg Met Gln Cys Leu Ala Ala
            100                 105                 110

Ala Leu Lys Asp Glu Thr Asn Met Ser Gly Gly Gly Glu Gln Ala Asp
        115                 120                 125

Ile Leu Pro Ala Asn Tyr Val Val Lys Asp Arg Trp Lys Val Leu Lys
    130                 135                 140

Lys Ile Gly Gly Gly Gly Phe Gly Glu Ile Tyr Glu Ala Met Asp Leu
145                 150                 155                 160

Leu Thr Arg Glu Asn Val Ala Leu Lys Val Glu Ser Ala Gln Gln Pro
                165                 170                 175
```

-continued

```
Lys Gln Val Leu Lys Met Glu Val Ala Val Leu Lys Lys Leu Gln Gly
            180                 185                 190

Lys Asp His Val Cys Arg Phe Ile Gly Cys Gly Arg Asn Glu Lys Phe
        195                 200                 205

Asn Tyr Val Val Met Gln Leu Gln Gly Arg Asn Leu Ala Asp Leu Arg
    210                 215                 220

Arg Ser Gln Pro Arg Gly Thr Phe Thr Leu Ser Thr Thr Leu Arg Leu
225                 230                 235                 240

Gly Lys Gln Ile Leu Glu Ser Ile Glu Ala Ile His Ser Val Gly Phe
                245                 250                 255

Leu His Arg Asp Ile Lys Pro Ser Asn Phe Ala Met Gly Arg Leu Pro
            260                 265                 270

Ser Thr Tyr Arg Lys Cys Tyr Met Leu Asp Phe Gly Leu Ala Arg Gln
        275                 280                 285

Tyr Thr Asn Thr Thr Gly Asp Val Arg Pro Pro Arg Asn Val Ala Gly
    290                 295                 300

Phe Arg Gly Thr Val Arg Tyr Ala Ser Val Asn Ala His Lys Asn Arg
305                 310                 315                 320

Glu Met Gly Arg His Asp Asp Leu Trp Ser Leu Phe Tyr Met Leu Val
                325                 330                 335

Glu Phe Ala Val Gly Gln Leu Pro Trp Arg Lys Ile Lys Asp Lys Glu
            340                 345                 350

Gln Val Gly Met Ile Lys Glu Lys Tyr Glu His Arg Met Leu Leu Lys
        355                 360                 365

His Met Pro Ser Glu Phe His Leu Phe Leu Asp His Ile Ala Ser Leu
    370                 375                 380

Asp Tyr Phe Thr Lys Pro Asp Tyr Gln Leu Ile Met Ser Val Phe Glu
385                 390                 395                 400

Asn Ser Met Lys Glu Arg Gly Ile Ala Glu Asn Glu Ala Phe Asp Trp
                405                 410                 415

Glu Lys Ala Gly Thr Asp Ala Leu Leu Ser Thr Ser Thr Ser Thr Pro
            420                 425                 430

Pro Gln Gln Asn Thr Arg Gln Thr Ala Ala Met Phe Gly Val Val Asn
        435                 440                 445

Val Thr Pro Val Pro Gly Asp Leu Leu Arg Glu Asn Thr Glu Asp Val
    450                 455                 460

Leu Gln Gly Glu His Leu Ser Asp Gln Glu Asn Ala Pro Pro Ile Leu
465                 470                 475                 480

Pro Gly Arg Pro Ser Glu Gly Leu Gly Pro Ser Pro His Leu Val Pro
                485                 490                 495

His Pro Gly Gly Pro Glu Ala Glu Val Trp Glu Glu Thr Asp Val Asn
            500                 505                 510

Arg Asn Lys Leu Arg Ile Asn Ile Gly Lys Ser Pro Cys Val Glu Glu
        515                 520                 525

Glu Gln Ser Arg Gly Met Gly Val Pro Ser Ser Pro Val Arg Ala Pro
    530                 535                 540

Pro Asp Ser Pro Thr Thr Pro Val Arg Ser Leu Arg Tyr Arg Arg Val
545                 550                 555                 560

Asn Ser Pro Glu Ser Glu Arg Leu Ser Thr Ala Asp Gly Arg Val Glu
                565                 570                 575

Leu Pro Glu Arg Arg Ser Arg Met Asp Leu Pro Gly Ser Pro Ser Arg
            580                 585                 590

Gln Ala Cys Ser Ser Gln Pro Ala Gln Met Leu Ser Val Asp Thr Gly
```

-continued

```
        595                 600                 605

His Ala Asp Arg Gln Ala Ser Gly Arg Met Asp Val Ser Ala Ser Val
    610                 615                 620

Glu Gln Glu Ala Leu Ser Asn Ala Phe Arg Ser Val Pro Leu Ala Glu
625                 630                 635                 640

Glu Glu Asp Phe Asp Ser Lys Glu Trp Val Ile Ile Asp Lys Glu Thr
                645                 650                 655

Glu Leu Lys Asp Phe Pro Pro Gly Ala Glu Pro Ser Thr Ser Gly Thr
            660                 665                 670

Thr Asp Glu Glu Pro Glu Glu Leu Arg Pro Leu Pro Glu Glu Gly Glu
        675                 680                 685

Glu Arg Arg Arg Leu Gly Ala Glu Pro Thr Val Arg Pro Arg Gly Arg
    690                 695                 700

Ser Met Gln Ala Leu Ala Glu Glu Asp Leu Gln His Leu Pro Pro Gln
705                 710                 715                 720

Pro Leu Pro Pro Gln Leu Ser Gln Xaa Asp Gly Arg Ser Glu Thr Ser
                725                 730                 735

Gln Pro Pro Thr Pro Gly Ser Pro Ser His Ser Pro Leu His Ser Gly
            740                 745                 750

Pro Arg Pro Arg Arg Arg Glu Ser Asp Pro Thr Gly Pro Gln Arg Gln
        755                 760                 765

Leu Glu Glu Asp Arg Leu Ser Gly His Ser Leu Pro Arg Tyr Ser Pro
    770                 775                 780

Leu Arg Arg Leu Ala Ser Ser Val Phe Ser Ser Ser Thr Leu Glu Thr
785                 790                 795                 800

Glu His Tyr Pro His Pro Gly Gly Gly Gly Ser Ser Gly Ser Ser Gly
                805                 810                 815

Ser Leu Ile Gln Arg Ser Arg Ser Ala Glu Ser Ser Pro Val Arg Ala
            820                 825                 830

Pro His Arg Arg His Ala Pro Leu Ala Ala Gly Asn His Arg Leu Met
        835                 840                 845

Pro Ser Val Leu Arg Ile Ser Arg Ser Gln Leu Gln Gln Val Trp Ala
    850                 855                 860

Arg Phe Thr His Lys Thr
865                 870
```

<210> SEQ ID NO 3
<211> LENGTH: 2595
<212> TYPE: DNA
<213> ORGANISM: homo sapiens

<400> SEQUENCE: 3

```
atgctggcgg cgcggtgcat tgtgggcagc tccccgctct gccgctgccg ccgccgtcgc      60

ccaaggagga tcggggccgg gccgggccgg gatgatccgg gtcggaaggc cgccgccgcc     120

ggagggagcg ggtcacccaa cgccgcactg agccgccccc gccccgcccc ggccccgggg     180

gatgcgccgc cccgagctgc tgcctccgcc gccgccgcag ccgcagccgc agcgggcaca     240

gagcaggtag atggccccct cagggcaggc ccggcggaca cccctccctc tggctggcgg     300

atgcagtgcc tagcggccgc ccttaaggac gaaaccaaca tgagtggggg aggggagcag     360

gccgacatcc tgccggccaa ctacgtggtc aaggatcgct ggaaggtgct gaaaaagatc     420

gggggcgggg gctttggtga gatctacgag gccatggacc tgctgaccag ggagaatgtg     480

gccctcaagg tggagtcagc ccagcagccc aagcaggtcc tcaagatgga ggtggccgtg     540
```

-continued

```
ctcaagaagt tgcaagggaa ggaccatgtg tgcaggttca ttggctgtgg caggaacgag    600

aagtttaact atgtagtgat gcagctccag ggccggaacc tggccgacct gcgccgtagc    660

cagccgcgag gcaccttcac gctgagcacc acattgcggc tgggcaagca gatcttggag    720

tccatcgagg ccatccactc tgtgggcttc ctgcaccgtg acatcaagcc ttcaaacttt    780

gccatgggca ggctgccctc cacctacagg aagtgctata tgctggactt cgggctggcc    840

cggcagtaca ccaacaccac gggggatgtg cggcccccctc ggaatgtggc cgggtttcga    900

ggaacggttc gctatgcctc agtcaatgcc cacaagaacc gggagatggg ccgccacgac    960

gacctgtggt ccctcttcta catgctggtg gagtttgcag tgggccagct gccctggagg   1020

aagatcaagg acaaggaaca ggtagggatg atcaaggaga agtatgagca ccggatgctg   1080

ctgaagcaca tgccgtcaga gttccacctc ttcctggacc acattgccag cctcgactac   1140

ttcaccaagc ccgactacca gttgatcatg tcagtgtttg agaacagcat gaaggagagg   1200

ggcattgccg agaatgaggc ctttgactgg gagaaggcag gcaccgatgc cctcctgtcc   1260

acgagcacct ctaccccgcc ccagcagaac acccggcaga cggcagccat gtttggggtg   1320

gtcaatgtga cgccagtgcc tggggacctg ctccgggaga acaccgagga tgtgctacag   1380

ggagagcacc tgagtgacca ggagaatgca cccccaattc tgcccgggag gccctctgag   1440

gggctgggcc ccagtcccca ccttgtcccc caccccgggg gtcctgaggc tgaagtctgg   1500

gaggagacag atgtcaaccg gaacaaactc cggatcaaca tcggcaaaag cccctgtgtg   1560

gaggaggaac agagccgagg catgggggtc cccagctccc cagtgcgtgc ccccccagac   1620

tcccccacaa ccccagtccg ttctctgcgc taccggaggg tgaacagccc tgagtcagaa   1680

aggctgtcca cggcggacgg gcgagtggag ctacctgaga ggaggtcacg gatggatctg   1740

cctggctcgc cctcgcgcca ggcctgctcc tctcagccag cccagatgct gtcagtggac   1800

acaggccacg ctgaccgaca ggccagtggc cgcatggayg tgtcagcctc tgtggagcag   1860

gaggccctga gcaacgcctt ccgctcggtg ccgctggctg aggaggagga tttcgacagc   1920

aaagagtggg tcatcatcga caaggagacg gagctcaagg acttccctcc aggggctgag   1980

cccagcacat cgggcaccac ggatgaggag cccgaggagc tgcggccact gcccgaggag   2040

ggcgaagagc ggcggcggct gggggcagag cccaccgtcc ggccccgggg acgcagcatg   2100

caggcgctgg cggaggagga cctgcagcat ttgccgcccc agcccctgcc accccagctg   2160

agccaggscg atggccgttc cgagacgtca cagcccccca cgcctggcag cccttcccac   2220

tcacccctgc actcgggacc ccgccctcga cggagagagt cggaccccac aggcccacag   2280

agacagttgg aggaggacag actctcgggg cactccctcc cgcggtacag ccccctgcga   2340

cgactggcgt cctccgtgtt ctcctcctcc acgctggaga cggagcatta ccctcacccc   2400

ggcggcggcg gctcctcggg ctcctccggt tccctcattc agcgcagccg ctcggctgag   2460

agcagccctg tgcgggcgcc ccaccggcgc cacgcgcccc tcgctgctgg caaccacaga   2520

ctcatgccct cggtgctccg catctcgcgg tcccagctgc agcaggtgtg ggcccggttc   2580

acccacaaga cctag                                                    2595
```

<210> SEQ ID NO 4
<211> LENGTH: 864
<212> TYPE: PRT
<213> ORGANISM: homo sapiens
<220> FEATURE:
<221> NAME/KEY: VARIANT
<222> LOCATION: (1)...(864)
<223> OTHER INFORMATION: Xaa = Any Amino Acid

<400> SEQUENCE: 4

```
Met Leu Ala Ala Arg Cys Ile Val Gly Ser Ser Pro Leu Cys Arg Cys
 1               5                  10                  15

Arg Arg Arg Arg Pro Arg Arg Ile Gly Ala Gly Pro Gly Arg Asp Asp
            20                  25                  30

Pro Gly Arg Lys Ala Ala Ala Ala Gly Gly Ser Gly Ser Pro Asn Ala
        35                  40                  45

Ala Leu Ser Arg Pro Arg Pro Ala Pro Ala Pro Gly Asp Ala Pro Pro
    50                  55                  60

Arg Ala Ala Ala Ser Ala Ala Ala Ala Ala Ala Ala Ala Ala Gly Thr
65                  70                  75                  80

Glu Gln Val Asp Gly Pro Leu Arg Ala Gly Pro Ala Asp Thr Pro Pro
                85                  90                  95

Ser Gly Trp Arg Met Gln Cys Leu Ala Ala Ala Leu Lys Asp Glu Thr
            100                 105                 110

Asn Met Ser Gly Gly Gly Glu Gln Ala Asp Ile Leu Pro Ala Asn Tyr
        115                 120                 125

Val Val Lys Asp Arg Trp Lys Val Leu Lys Lys Ile Gly Gly Gly Gly
    130                 135                 140

Phe Gly Glu Ile Tyr Glu Ala Met Asp Leu Leu Thr Arg Glu Asn Val
145                 150                 155                 160

Ala Leu Lys Val Glu Ser Ala Gln Gln Pro Lys Gln Val Leu Lys Met
                165                 170                 175

Glu Val Ala Val Leu Lys Lys Leu Gln Gly Lys Asp His Val Cys Arg
            180                 185                 190

Phe Ile Gly Cys Gly Arg Asn Glu Lys Phe Asn Tyr Val Val Met Gln
        195                 200                 205

Leu Gln Gly Arg Asn Leu Ala Asp Leu Arg Arg Ser Gln Pro Arg Gly
    210                 215                 220

Thr Phe Thr Leu Ser Thr Thr Leu Arg Leu Gly Lys Gln Ile Leu Glu
225                 230                 235                 240

Ser Ile Glu Ala Ile His Ser Val Gly Phe Leu His Arg Asp Ile Lys
                245                 250                 255

Pro Ser Asn Phe Ala Met Gly Arg Leu Pro Ser Thr Tyr Arg Lys Cys
            260                 265                 270

Tyr Met Leu Asp Phe Gly Leu Ala Arg Gln Tyr Thr Asn Thr Thr Gly
        275                 280                 285

Asp Val Arg Pro Pro Arg Asn Val Ala Gly Phe Arg Gly Thr Val Arg
    290                 295                 300

Tyr Ala Ser Val Asn Ala His Lys Asn Arg Glu Met Gly Arg His Asp
305                 310                 315                 320

Asp Leu Trp Ser Leu Phe Tyr Met Leu Val Glu Phe Ala Val Gly Gln
                325                 330                 335

Leu Pro Trp Arg Lys Ile Lys Asp Lys Glu Gln Val Gly Met Ile Lys
            340                 345                 350

Glu Lys Tyr Glu His Arg Met Leu Leu Lys His Met Pro Ser Glu Phe
        355                 360                 365

His Leu Phe Leu Asp His Ile Ala Ser Leu Asp Tyr Phe Thr Lys Pro
    370                 375                 380

Asp Tyr Gln Leu Ile Met Ser Val Phe Glu Asn Ser Met Lys Glu Arg
385                 390                 395                 400

Gly Ile Ala Glu Asn Glu Ala Phe Asp Trp Glu Lys Ala Gly Thr Asp
```

-continued

```
                405                 410                 415

Ala Leu Leu Ser Thr Ser Thr Ser Thr Pro Pro Gln Gln Asn Thr Arg
            420                 425                 430

Gln Thr Ala Ala Met Phe Gly Val Val Asn Val Thr Pro Val Pro Gly
        435                 440                 445

Asp Leu Leu Arg Glu Asn Thr Glu Asp Val Leu Gln Gly Glu His Leu
    450                 455                 460

Ser Asp Gln Glu Asn Ala Pro Pro Ile Leu Pro Gly Arg Pro Ser Glu
465                 470                 475                 480

Gly Leu Gly Pro Ser Pro His Leu Val Pro His Pro Gly Gly Pro Glu
                485                 490                 495

Ala Glu Val Trp Glu Glu Thr Asp Val Asn Arg Asn Lys Leu Arg Ile
            500                 505                 510

Asn Ile Gly Lys Ser Pro Cys Val Glu Glu Glu Gln Ser Arg Gly Met
        515                 520                 525

Gly Val Pro Ser Ser Pro Val Arg Ala Pro Pro Asp Ser Pro Thr Thr
    530                 535                 540

Pro Val Arg Ser Leu Arg Tyr Arg Arg Val Asn Ser Pro Glu Ser Glu
545                 550                 555                 560

Arg Leu Ser Thr Ala Asp Gly Arg Val Glu Leu Pro Glu Arg Arg Ser
                565                 570                 575

Arg Met Asp Leu Pro Gly Ser Pro Ser Arg Gln Ala Cys Ser Ser Gln
            580                 585                 590

Pro Ala Gln Met Leu Ser Val Asp Thr Gly His Ala Asp Arg Gln Ala
        595                 600                 605

Ser Gly Arg Met Asp Val Ser Ala Ser Val Glu Gln Glu Ala Leu Ser
    610                 615                 620

Asn Ala Phe Arg Ser Val Pro Leu Ala Glu Glu Glu Asp Phe Asp Ser
625                 630                 635                 640

Lys Glu Trp Val Ile Ile Asp Lys Glu Thr Glu Leu Lys Asp Phe Pro
                645                 650                 655

Pro Gly Ala Glu Pro Ser Thr Ser Gly Thr Thr Asp Glu Glu Pro Glu
            660                 665                 670

Glu Leu Arg Pro Leu Pro Glu Glu Gly Glu Glu Arg Arg Arg Leu Gly
        675                 680                 685

Ala Glu Pro Thr Val Arg Pro Arg Gly Arg Ser Met Gln Ala Leu Ala
    690                 695                 700

Glu Glu Asp Leu Gln His Leu Pro Pro Gln Pro Leu Pro Pro Gln Leu
705                 710                 715                 720

Ser Gln Xaa Asp Gly Arg Ser Glu Thr Ser Gln Pro Pro Thr Pro Gly
                725                 730                 735

Ser Pro Ser His Ser Pro Leu His Ser Gly Pro Arg Pro Arg Arg Arg
            740                 745                 750

Glu Ser Asp Pro Thr Gly Pro Gln Arg Gln Leu Glu Glu Asp Arg Leu
        755                 760                 765

Ser Gly His Ser Leu Pro Arg Tyr Ser Pro Leu Arg Arg Leu Ala Ser
    770                 775                 780

Ser Val Phe Ser Ser Ser Thr Leu Glu Thr Glu His Tyr Pro His Pro
785                 790                 795                 800

Gly Gly Gly Gly Ser Ser Gly Ser Ser Gly Ser Leu Ile Gln Arg Ser
                805                 810                 815

Arg Ser Ala Glu Ser Ser Pro Val Arg Ala Pro His Arg Arg His Ala
            820                 825                 830
```

-continued

```
Pro Leu Ala Ala Gly Asn His Arg Leu Met Pro Ser Val Leu Arg Ile
        835                 840                 845

Ser Arg Ser Gln Leu Gln Gln Val Trp Ala Arg Phe Thr His Lys Thr
    850                 855                 860
```

```
<210> SEQ ID NO 5
<211> LENGTH: 2295
<212> TYPE: DNA
<213> ORGANISM: homo sapiens

<400> SEQUENCE: 5

atgcagtgcc tagcggccgc ccttaaggac gaaaccaaca tgagtggggg aggggagcag      60

gccgacatcc tgccggccaa ctacgtggtc aaggatcgct ggaaggtgct gaaaaagatc     120

gggggcgggg gctttggtga gatctacgag gccatggacc tgctgaccag ggagaatgtg     180

gccctcaagg tggagtcagc ccagcagccc aagcaggtcc tcaagatgga ggtggccgtg     240

ctcaagaagt tgcaagggaa ggaccatgtg tgcaggttca ttggctgtgg caggaacgag     300

aagtttaact atgtagtgat gcagctccag ggccggaacc tggccgacct gcgccgtagc     360

cagccgcgag gcaccttcac gctgagcacc acattgcggc tgggcaagca gatcttggag     420

tccatcgagg ccatccactc tgtgggcttc ctgcaccgtg acatcaagcc ttcaaacttt     480

gccatgggca ggctgccctc cacctacagg aagtgctata tgctggactt cgggctggcc     540

cggcagtaca ccaacaccac gggggatgtg cggcccccctc ggaatgtggc cgggtttcga     600

ggaacggttc gctatgcctc agtcaatgcc cacaagaacc gggagatggg ccgccacgac     660

gacctgtggt ccctcttcta catgctggtg gagtttgcag tgggccagct gccctggagg     720

aagatcaagg acaaggaaca ggtagggatg atcaaggaga agtatgagca ccggatgctg     780

ctgaagcaca tgccgtcaga gttccacctc ttcctggacc acattgccag cctcgactac     840

ttcaccaagc ccgactacca gttgatcatg tcagtgtttg agaacagcat gaaggagagg     900

ggcattgccg agaatgaggc ctttgactgg gagaaggcag gcaccgatgc cctcctgtcc     960

acgagcacct ctaccccgcc ccagcagaac acccggcaga cggcagccat gtttggggtg    1020

gtcaatgtga cgccagtgcc tggggacctg ctccgggaga acaccgagga tgtgctacag    1080

ggagagcacc tgagtgacca ggagaatgca cccccaattc tgcccgggag gccctctgag    1140

gggctgggcc ccagtcccca ccttgtcccc caccccgggg gtcctgaggc tgaagtctgg    1200

gaggagacag atgtcaaccg gaacaaactc cggatcaaca tcggcaaaag cccctgtgtg    1260

gaggaggaac agagccgagg catgggggtc cccagctccc cagtgcgtgc ccccccagac    1320

tcccccacaa ccccagtccg ttctctgcgc taccggaggg tgaacagccc tgagtcagaa    1380

aggctgtcca cggcggacgg gcgagtggag ctacctgaga ggaggtcacg gatggatctg    1440

cctggctcgc cctcgcgcca ggcctgctcc tctcagccag cccagatgct gtcagtggac    1500

acaggccacg ctgaccgaca ggccagtggc cgcatggayg tgtcagcctc tgtggagcag    1560

gaggccctga gcaacgcctt ccgctcggtg ccgctggctg aggaggagga tttcgacagc    1620

aaagagtggg tcatcatcga caaggagacg gagctcaagg acttccctcc aggggctgag    1680

cccagcacat cgggcaccac ggatgaggag cccgaggagc tgcggccact gcccgaggag    1740

ggcgaagagc ggcggcggct gggggcagag cccaccgtcc ggccccgggg acgcagcatg    1800

caggcgctgg cggaggagga cctgcagcat ttgccgcccc agcccctgcc accccagctg    1860

agccaggscg atggccgttc cgagacgtca cagcccccca cgcctggcag cccttcccac    1920
```

-continued

```
tcacccctgc actcgggacc ccgccctcga cggagagagt cggaccccac aggcccacag   1980

agacagttgg aggaggacag actctcgggg cactccctcc cgcggtacag ccccctgcga   2040

cgactggcgt cctccgtgtt ctcctcctcc acgctggaga cggagcatta ccctcacccc   2100

ggcggcggcg gctcctcggg ctcctccggt tccctcattc agcgcagccg ctcggctgag   2160

agcagccctg tgcgggcgcc ccaccggcgc cacgcgcccc tcgctgctgg caaccacaga   2220

ctcatgccct cggtgctccg catctcgcgg tcccagctgc agcaggtgtg ggcccggttc   2280

acccacaaga cctag                                                    2295
```

```
<210> SEQ ID NO 6
<211> LENGTH: 764
<212> TYPE: PRT
<213> ORGANISM: homo sapiens
<220> FEATURE:
<221> NAME/KEY: VARIANT
<222> LOCATION: (1)...(764)
<223> OTHER INFORMATION: Xaa = Any Amino Acid

<400> SEQUENCE: 6

Met Gln Cys Leu Ala Ala Ala Leu Lys Asp Glu Thr Asn Met Ser Gly
 1               5                  10                  15

Gly Gly Glu Gln Ala Asp Ile Leu Pro Ala Asn Tyr Val Val Lys Asp
            20                  25                  30

Arg Trp Lys Val Leu Lys Lys Ile Gly Gly Gly Gly Phe Gly Glu Ile
        35                  40                  45

Tyr Glu Ala Met Asp Leu Leu Thr Arg Glu Asn Val Ala Leu Lys Val
    50                  55                  60

Glu Ser Ala Gln Gln Pro Lys Gln Val Leu Lys Met Glu Val Ala Val
65                  70                  75                  80

Leu Lys Lys Leu Gln Gly Lys Asp His Val Cys Arg Phe Ile Gly Cys
                85                  90                  95

Gly Arg Asn Glu Lys Phe Asn Tyr Val Val Met Gln Leu Gln Gly Arg
            100                 105                 110

Asn Leu Ala Asp Leu Arg Arg Ser Gln Pro Arg Gly Thr Phe Thr Leu
        115                 120                 125

Ser Thr Thr Leu Arg Leu Gly Lys Gln Ile Leu Glu Ser Ile Glu Ala
    130                 135                 140

Ile His Ser Val Gly Phe Leu His Arg Asp Ile Lys Pro Ser Asn Phe
145                 150                 155                 160

Ala Met Gly Arg Leu Pro Ser Thr Tyr Arg Lys Cys Tyr Met Leu Asp
                165                 170                 175

Phe Gly Leu Ala Arg Gln Tyr Thr Asn Thr Thr Gly Asp Val Arg Pro
            180                 185                 190

Pro Arg Asn Val Ala Gly Phe Arg Gly Thr Val Arg Tyr Ala Ser Val
        195                 200                 205

Asn Ala His Lys Asn Arg Glu Met Gly Arg His Asp Asp Leu Trp Ser
    210                 215                 220

Leu Phe Tyr Met Leu Val Glu Phe Ala Val Gly Gln Leu Pro Trp Arg
225                 230                 235                 240

Lys Ile Lys Asp Lys Glu Gln Val Gly Met Ile Lys Glu Lys Tyr Glu
                245                 250                 255

His Arg Met Leu Leu Lys His Met Pro Ser Glu Phe His Leu Phe Leu
            260                 265                 270

Asp His Ile Ala Ser Leu Asp Tyr Phe Thr Lys Pro Asp Tyr Gln Leu
        275                 280                 285
```

-continued

```
Ile Met Ser Val Phe Glu Asn Ser Met Lys Glu Arg Gly Ile Ala Glu
    290                 295                 300

Asn Glu Ala Phe Asp Trp Glu Lys Ala Gly Thr Asp Ala Leu Leu Ser
305                 310                 315                 320

Thr Ser Thr Ser Thr Pro Pro Gln Gln Asn Thr Arg Gln Thr Ala Ala
                325                 330                 335

Met Phe Gly Val Val Asn Val Thr Pro Val Pro Gly Asp Leu Leu Arg
            340                 345                 350

Glu Asn Thr Glu Asp Val Leu Gln Gly Glu His Leu Ser Asp Gln Glu
        355                 360                 365

Asn Ala Pro Pro Ile Leu Pro Gly Arg Pro Ser Glu Gly Leu Gly Pro
    370                 375                 380

Ser Pro His Leu Val Pro His Pro Gly Gly Pro Glu Ala Glu Val Trp
385                 390                 395                 400

Glu Glu Thr Asp Val Asn Arg Asn Lys Leu Arg Ile Asn Ile Gly Lys
                405                 410                 415

Ser Pro Cys Val Glu Glu Glu Gln Ser Arg Gly Met Gly Val Pro Ser
            420                 425                 430

Ser Pro Val Arg Ala Pro Pro Asp Ser Pro Thr Thr Pro Val Arg Ser
        435                 440                 445

Leu Arg Tyr Arg Arg Val Asn Ser Pro Glu Ser Glu Arg Leu Ser Thr
    450                 455                 460

Ala Asp Gly Arg Val Glu Leu Pro Glu Arg Arg Ser Arg Met Asp Leu
465                 470                 475                 480

Pro Gly Ser Pro Ser Arg Gln Ala Cys Ser Ser Gln Pro Ala Gln Met
                485                 490                 495

Leu Ser Val Asp Thr Gly His Ala Asp Arg Gln Ala Ser Gly Arg Met
            500                 505                 510

Asp Val Ser Ala Ser Val Glu Gln Glu Ala Leu Ser Asn Ala Phe Arg
        515                 520                 525

Ser Val Pro Leu Ala Glu Glu Glu Asp Phe Asp Ser Lys Glu Trp Val
    530                 535                 540

Ile Ile Asp Lys Glu Thr Glu Leu Lys Asp Phe Pro Pro Gly Ala Glu
545                 550                 555                 560

Pro Ser Thr Ser Gly Thr Thr Asp Glu Glu Pro Glu Glu Leu Arg Pro
                565                 570                 575

Leu Pro Glu Glu Gly Glu Glu Arg Arg Arg Leu Gly Ala Glu Pro Thr
            580                 585                 590

Val Arg Pro Arg Gly Arg Ser Met Gln Ala Leu Ala Glu Glu Asp Leu
        595                 600                 605

Gln His Leu Pro Pro Gln Pro Leu Pro Pro Gln Leu Ser Gln Xaa Asp
    610                 615                 620

Gly Arg Ser Glu Thr Ser Gln Pro Pro Thr Pro Gly Ser Pro Ser His
625                 630                 635                 640

Ser Pro Leu His Ser Gly Pro Arg Pro Arg Arg Arg Glu Ser Asp Pro
                645                 650                 655

Thr Gly Pro Gln Arg Gln Leu Glu Glu Asp Arg Leu Ser Gly His Ser
            660                 665                 670

Leu Pro Arg Tyr Ser Pro Leu Arg Arg Leu Ala Ser Ser Val Phe Ser
        675                 680                 685

Ser Ser Thr Leu Glu Thr Glu His Tyr Pro His Pro Gly Gly Gly Gly
    690                 695                 700
```

-continued

```
Ser Ser Gly Ser Ser Gly Ser Leu Ile Gln Arg Ser Arg Ser Ala Glu
705                 710                 715                 720

Ser Ser Pro Val Arg Ala Pro His Arg Arg His Ala Pro Leu Ala Ala
                725                 730                 735

Gly Asn His Arg Leu Met Pro Ser Val Leu Arg Ile Ser Arg Ser Gln
            740                 745                 750

Leu Gln Gln Val Trp Ala Arg Phe Thr His Lys Thr
        755                 760
```

<210> SEQ ID NO 7
<211> LENGTH: 2256
<212> TYPE: DNA
<213> ORGANISM: homo sapiens

<400> SEQUENCE: 7

```
atgagtgggg gaggggagca ggccgacatc ctgccggcca actacgtggt caaggatcgc     60

tggaaggtgc tgaaaaagat cgggggcggg ggctttggtg agatctacga ggccatggac    120

ctgctgacca gggagaatgt ggccctcaag gtggagtcag cccagcagcc caagcaggtc    180

ctcaagatgg aggtggccgt gctcaagaag ttgcaaggga aggaccatgt gtgcaggttc    240

attggctgtg gcaggaacga gaagtttaac tatgtagtga tgcagctcca gggccggaac    300

ctggccgacc tgcgccgtag ccagccgcga ggcaccttca cgctgagcac cacattgcgg    360

ctgggcaagc agatcttgga gtccatcgag gccatccact ctgtgggctt cctgcaccgt    420

gacatcaagc cttcaaactt tgccatgggc aggctgccct ccacctacag gaagtgctat    480

atgctggact tcgggctggc ccggcagtac accaacacca cgggggatgt gcggcccccct    540

cggaatgtgg ccgggtttcg aggaacggtt cgctatgcct cagtcaatgc ccacaagaac    600

cgggagatgg gccgccacga cgacctgtgg tccctcttct acatgctggt ggagtttgca    660

gtgggccagc tgccctggag gaagatcaag gacaaggaac aggtagggat gatcaaggag    720

aagtatgagc accggatgct gctgaagcac atgccgtcag agttccacct cttcctggac    780

cacattgcca gcctcgacta cttcaccaag cccgactacc agttgatcat gtcagtgttt    840

gagaacagca tgaaggagag ggcattgcc gagaatgagg cctttgactg ggagaaggca    900

ggcaccgatg ccctcctgtc cacgagcacc tctaccccgc cccagcagaa cacccggcag    960

acggcagcca tgtttggggt ggtcaatgtg acgccagtgc ctggggacct gctccgggag   1020

aacaccgagg atgtgctaca gggagagcac ctgagtgacc aggagaatgc acccccaatt   1080

ctgcccggga ggccctctga ggggctgggc cccagtcccc accttgtccc ccaccccggg   1140

ggtcctgagg ctgaagtctg ggaggagaca gatgtcaacc ggaacaaact ccggatcaac   1200

atcggcaaaa gcccctgtgt ggaggaggaa cagagccgag gcatgggggt ccccagctcc   1260

ccagtgcgtg cccccccaga ctcccccaca accccagtcc gttctctgcg ctaccggagg   1320

gtgaacagcc ctgagtcaga aaggctgtcc acggcggacg ggcgagtgga gctacctgag   1380

aggaggtcac ggatggatct gcctggctcg ccctcgcgcc aggcctgctc ctctcagcca   1440

gcccagatgc tgtcagtgga cacaggccac gctgaccgac aggccagtgg ccgcatggay   1500

gtgtcagcct ctgtggagca ggaggccctg agcaacgcct tccgctcggt gccgctggct   1560

gaggaggagg atttcgacag caaagagtgg gtcatcatcg acaaggagac ggagctcaag   1620

gacttccctc caggggctga gcccagcaca tcgggcacca cggatgagga gcccgaggag   1680

ctgcggccac tgcccgagga gggcgaagag cggcggcggc tgggggcaga gcccaccgtc   1740

cggccccggg gacgcagcat gcaggcgctg gcggaggagg acctgcagca tttgccgccc   1800
```

```
cagcccctgc caccccagct gagccaggsc gatggccgtt ccgagacgtc acagcccccc   1860

acgcctggca gcccttccca ctcaccccctg cactcgggac cccgccctcg acggagagag   1920

tcggacccca caggcccaca gagacagttg gaggaggaca gactctcggg gcactccctc   1980

ccgcggtaca gccccctgcg acgactggcg tcctccgtgt tctcctcctc cacgctggag   2040

acggagcatt accctcaccc cggcggcggc ggctcctcgg gctcctccgg ttccctcatt   2100

cagcgcagcc gctcggctga gagcagccct gtgcgggcgc cccaccggcg ccacgcgccc   2160

ctcgctgctg gcaaccacag actcatgccc tcggtgctcc gcatctcgcg gtcccagctg   2220

cagcaggtgt gggcccggtt cacccacaag acctag                             2256
```

```
<210> SEQ ID NO 8
<211> LENGTH: 751
<212> TYPE: PRT
<213> ORGANISM: homo sapiens
<220> FEATURE:
<221> NAME/KEY: VARIANT
<222> LOCATION: (1)...(751)
<223> OTHER INFORMATION: Xaa = Any Amino Acid

<400> SEQUENCE: 8

Met Ser Gly Gly Gly Glu Gln Ala Asp Ile Leu Pro Ala Asn Tyr Val
 1               5                  10                  15

Val Lys Asp Arg Trp Lys Val Leu Lys Lys Ile Gly Gly Gly Gly Phe
            20                  25                  30

Gly Glu Ile Tyr Glu Ala Met Asp Leu Leu Thr Arg Glu Asn Val Ala
        35                  40                  45

Leu Lys Val Glu Ser Ala Gln Gln Pro Lys Gln Val Leu Lys Met Glu
    50                  55                  60

Val Ala Val Leu Lys Lys Leu Gln Gly Lys Asp His Val Cys Arg Phe
65                  70                  75                  80

Ile Gly Cys Gly Arg Asn Glu Lys Phe Asn Tyr Val Val Met Gln Leu
                85                  90                  95

Gln Gly Arg Asn Leu Ala Asp Leu Arg Arg Ser Gln Pro Arg Gly Thr
            100                 105                 110

Phe Thr Leu Ser Thr Thr Leu Arg Leu Gly Lys Gln Ile Leu Glu Ser
        115                 120                 125

Ile Glu Ala Ile His Ser Val Gly Phe Leu His Arg Asp Ile Lys Pro
    130                 135                 140

Ser Asn Phe Ala Met Gly Arg Leu Pro Ser Thr Tyr Arg Lys Cys Tyr
145                 150                 155                 160

Met Leu Asp Phe Gly Leu Ala Arg Gln Tyr Thr Asn Thr Thr Gly Asp
                165                 170                 175

Val Arg Pro Pro Arg Asn Val Ala Gly Phe Arg Gly Thr Val Arg Tyr
            180                 185                 190

Ala Ser Val Asn Ala His Lys Asn Arg Glu Met Gly Arg His Asp Asp
        195                 200                 205

Leu Trp Ser Leu Phe Tyr Met Leu Val Glu Phe Ala Val Gly Gln Leu
    210                 215                 220

Pro Trp Arg Lys Ile Lys Asp Lys Glu Gln Val Gly Met Ile Lys Glu
225                 230                 235                 240

Lys Tyr Glu His Arg Met Leu Leu Lys His Met Pro Ser Glu Phe His
                245                 250                 255

Leu Phe Leu Asp His Ile Ala Ser Leu Asp Tyr Phe Thr Lys Pro Asp
            260                 265                 270
```

-continued

```
Tyr Gln Leu Ile Met Ser Val Phe Glu Asn Ser Met Lys Glu Arg Gly
        275                 280                 285

Ile Ala Glu Asn Glu Ala Phe Asp Trp Glu Lys Ala Gly Thr Asp Ala
    290                 295                 300

Leu Leu Ser Thr Ser Thr Ser Thr Pro Pro Gln Gln Asn Thr Arg Gln
305                 310                 315                 320

Thr Ala Ala Met Phe Gly Val Val Asn Val Thr Pro Val Pro Gly Asp
                325                 330                 335

Leu Leu Arg Glu Asn Thr Glu Asp Val Leu Gln Gly Glu His Leu Ser
            340                 345                 350

Asp Gln Glu Asn Ala Pro Pro Ile Leu Pro Gly Arg Pro Ser Glu Gly
        355                 360                 365

Leu Gly Pro Ser Pro His Leu Val Pro His Pro Gly Gly Pro Glu Ala
    370                 375                 380

Glu Val Trp Glu Glu Thr Asp Val Asn Arg Asn Lys Leu Arg Ile Asn
385                 390                 395                 400

Ile Gly Lys Ser Pro Cys Val Glu Glu Glu Gln Ser Arg Gly Met Gly
                405                 410                 415

Val Pro Ser Ser Pro Val Arg Ala Pro Pro Asp Ser Pro Thr Thr Pro
            420                 425                 430

Val Arg Ser Leu Arg Tyr Arg Arg Val Asn Ser Pro Glu Ser Glu Arg
        435                 440                 445

Leu Ser Thr Ala Asp Gly Arg Val Glu Leu Pro Glu Arg Arg Ser Arg
    450                 455                 460

Met Asp Leu Pro Gly Ser Pro Ser Arg Gln Ala Cys Ser Ser Gln Pro
465                 470                 475                 480

Ala Gln Met Leu Ser Val Asp Thr Gly His Ala Asp Arg Gln Ala Ser
                485                 490                 495

Gly Arg Met Asp Val Ser Ala Ser Val Glu Gln Glu Ala Leu Ser Asn
            500                 505                 510

Ala Phe Arg Ser Val Pro Leu Ala Glu Glu Glu Asp Phe Asp Ser Lys
        515                 520                 525

Glu Trp Val Ile Ile Asp Lys Glu Thr Glu Leu Lys Asp Phe Pro Pro
    530                 535                 540

Gly Ala Glu Pro Ser Thr Ser Gly Thr Thr Asp Glu Glu Pro Glu Glu
545                 550                 555                 560

Leu Arg Pro Leu Pro Glu Glu Gly Glu Glu Arg Arg Arg Leu Gly Ala
                565                 570                 575

Glu Pro Thr Val Arg Pro Arg Gly Arg Ser Met Gln Ala Leu Ala Glu
            580                 585                 590

Glu Asp Leu Gln His Leu Pro Pro Gln Pro Leu Pro Pro Gln Leu Ser
        595                 600                 605

Gln Xaa Asp Gly Arg Ser Glu Thr Ser Gln Pro Pro Thr Pro Gly Ser
    610                 615                 620

Pro Ser His Ser Pro Leu His Ser Gly Pro Arg Pro Arg Arg Arg Glu
625                 630                 635                 640

Ser Asp Pro Thr Gly Pro Gln Arg Gln Leu Glu Glu Asp Arg Leu Ser
                645                 650                 655

Gly His Ser Leu Pro Arg Tyr Ser Pro Leu Arg Arg Leu Ala Ser Ser
            660                 665                 670

Val Phe Ser Ser Ser Thr Leu Glu Thr Glu His Tyr Pro His Pro Gly
        675                 680                 685
```

-continued

```
Gly Gly Gly Ser Ser Gly Ser Ser Gly Ser Leu Ile Gln Arg Ser Arg
    690                 695                 700

Ser Ala Glu Ser Ser Pro Val Arg Ala Pro His Arg Arg His Ala Pro
705                 710                 715                 720

Leu Ala Ala Gly Asn His Arg Leu Met Pro Ser Val Leu Arg Ile Ser
                725                 730                 735

Arg Ser Gln Leu Gln Gln Val Trp Ala Arg Phe Thr His Lys Thr
            740                 745                 750


<210> SEQ ID NO 9
<211> LENGTH: 1965
<212> TYPE: DNA
<213> ORGANISM: homo sapiens

<400> SEQUENCE: 9

atgtcagggc tggtgctgat gctggcggcg cggtgcattg tgggcagctc cccgctctgc      60

cgctgccgcc gccgtcgccc aaggaggatc ggggccgggc cgggccggga tgatccgggt     120

cggaaggccg ccgccgccgg agggagcggg tcacccaacg ccgcactgag ccgccccccgc     180

cccgccccgg ccccggggga tgcgccgccc cgagctgctg cctccgccgc cgccgcagcc     240

gcagccgcag cgggcacaga gcaggtagat ggccccctca gggcaggccc ggcggacacc     300

cctccctctg gctggcggat gcagtgccta gcggccgccc ttaaggacga aaccaacatg     360

agtgggggag gggagcaggc cgacatcctg ccggccaact acgtggtcaa ggatcgctgg     420

aaggtgctga aaaagatcgg gggcgggggc tttggtgaga tctacgaggc catggacctg     480

ctgaccaggg agaatgtggc cctcaaggtg gagtcagccc agcagcccaa gcaggtcctc     540

aagatggagg tggccgtgct caagaagttg caagggaagg accatgtgtg caggttcatt     600

ggctgtggca ggaacgagaa gtttaactat gtagtgatgc agctccaggg ccggaacctg     660

gccgacctgc gccgtagcca gccgcgaggc accttcacgc tgagcaccac attgcggctg     720

ggcaagcaga tcttggagtc catcgaggcc atccactctg tgggcttcct gcaccgtgac     780

atcaagcctt caaactttgc catgggcagg ctgccctcca cctacaggaa gtgctatatg     840

ctggacttcg ggctggcccg gcagtacacc aacaccacgg gggatgtgcg gccccctcgg     900

aatgtggccg ggtttcgagg aacggttcgc tatgcctcag tcaatgccca caagaaccgg     960

gagatgggcc gccacgacga cctgtggtcc ctcttctaca tgctggtgga gtttgcagtg    1020

ggccagctgc cctggaggaa gatcaaggac aaggaacagg tagggatgat caaggagaag    1080

tatgagcacc ggatgctgct gaagcacatg ccgtcagagt tccacctctt cctggaccac    1140

attgccagcc tcgactactt caccaagccc gactaccagt tgatcatgtc agtgtttgag    1200

aacagcatga aggagagggg cattgccgag aatgaggcct ttgactggga gaaggcaggc    1260

accgatgccc tcctgtccac gagcacctct accccgcccc agcagaacac ccggcagacg    1320

gcagccatgt ttggggtggt caatgtgacg ccagtgcctg ggggacctgct ccgggagaac    1380

accgaggatg tgctacaggg agagcacctg agtgaccagg agaatgcacc cccaattctg    1440

cccgggaggc cctctgaggg gctgggcccc agtccccacc ttgtccccca ccccgggggt    1500

cctgaggctg aagtctggga ggagacagat gtcaaccgga acaaactccg gatcaacatc    1560

ggcaaaagcc cctgtgtgga ggaggaacag agccgaggca tgggggtccc cagctcccca    1620

gtgcgtgccc ccccagactc cccccacaacc ccagtccgtt ctctgcgcta ccggagggtg    1680

aacagccctg agtcagaaag gctgtccacg gcggacgggc gagtggagct acctgagagg    1740

aggtgggtct ggggccaggg gcatggttgg ggcccaaggc cctctccgcc ttcacgtggc    1800
```

```
tggtctggag gaaaagttag atgtgtggcg gaggtgggca gaccctggga agtgctgaga   1860

gggttatact tgggcctggg gtcagactca gttggggcca sagacagggc ctgggaraac   1920

cagtgggga tccagagagg tcccggctca tgccaggaaa cgtaa                   1965


<210> SEQ ID NO 10
<211> LENGTH: 654
<212> TYPE: PRT
<213> ORGANISM: homo sapiens
<220> FEATURE:
<221> NAME/KEY: VARIANT
<222> LOCATION: (1)...(654)
<223> OTHER INFORMATION: Xaa = Any Amino Acid

<400> SEQUENCE: 10

Met Ser Gly Leu Val Leu Met Leu Ala Ala Arg Cys Ile Val Gly Ser
 1               5                  10                  15

Ser Pro Leu Cys Arg Cys Arg Arg Arg Arg Pro Arg Arg Ile Gly Ala
            20                  25                  30

Gly Pro Gly Arg Asp Asp Pro Gly Arg Lys Ala Ala Ala Ala Gly Gly
        35                  40                  45

Ser Gly Ser Pro Asn Ala Ala Leu Ser Arg Pro Arg Pro Ala Pro Ala
    50                  55                  60

Pro Gly Asp Ala Pro Pro Arg Ala Ala Ala Ser Ala Ala Ala Ala Ala
65                  70                  75                  80

Ala Ala Ala Ala Gly Thr Glu Gln Val Asp Gly Pro Leu Arg Ala Gly
                85                  90                  95

Pro Ala Asp Thr Pro Pro Ser Gly Trp Arg Met Gln Cys Leu Ala Ala
            100                 105                 110

Ala Leu Lys Asp Glu Thr Asn Met Ser Gly Gly Gly Glu Gln Ala Asp
        115                 120                 125

Ile Leu Pro Ala Asn Tyr Val Val Lys Asp Arg Trp Lys Val Leu Lys
    130                 135                 140

Lys Ile Gly Gly Gly Gly Phe Gly Glu Ile Tyr Glu Ala Met Asp Leu
145                 150                 155                 160

Leu Thr Arg Glu Asn Val Ala Leu Lys Val Glu Ser Ala Gln Gln Pro
                165                 170                 175

Lys Gln Val Leu Lys Met Glu Val Ala Val Leu Lys Lys Leu Gln Gly
            180                 185                 190

Lys Asp His Val Cys Arg Phe Ile Gly Cys Gly Arg Asn Glu Lys Phe
        195                 200                 205

Asn Tyr Val Val Met Gln Leu Gln Gly Arg Asn Leu Ala Asp Leu Arg
    210                 215                 220

Arg Ser Gln Pro Arg Gly Thr Phe Thr Leu Ser Thr Thr Leu Arg Leu
225                 230                 235                 240

Gly Lys Gln Ile Leu Glu Ser Ile Glu Ala Ile His Ser Val Gly Phe
                245                 250                 255

Leu His Arg Asp Ile Lys Pro Ser Asn Phe Ala Met Gly Arg Leu Pro
            260                 265                 270

Ser Thr Tyr Arg Lys Cys Tyr Met Leu Asp Phe Gly Leu Ala Arg Gln
        275                 280                 285

Tyr Thr Asn Thr Thr Gly Asp Val Arg Pro Pro Arg Asn Val Ala Gly
    290                 295                 300

Phe Arg Gly Thr Val Arg Tyr Ala Ser Val Asn Ala His Lys Asn Arg
305                 310                 315                 320
```

-continued

```
Glu Met Gly Arg His Asp Asp Leu Trp Ser Leu Phe Tyr Met Leu Val
                325                 330                 335

Glu Phe Ala Val Gly Gln Leu Pro Trp Arg Lys Ile Lys Asp Lys Glu
            340                 345                 350

Gln Val Gly Met Ile Lys Glu Lys Tyr Glu His Arg Met Leu Leu Lys
        355                 360                 365

His Met Pro Ser Glu Phe His Leu Phe Leu Asp His Ile Ala Ser Leu
    370                 375                 380

Asp Tyr Phe Thr Lys Pro Asp Tyr Gln Leu Ile Met Ser Val Phe Glu
385                 390                 395                 400

Asn Ser Met Lys Glu Arg Gly Ile Ala Glu Asn Glu Ala Phe Asp Trp
                405                 410                 415

Glu Lys Ala Gly Thr Asp Ala Leu Leu Ser Thr Ser Thr Ser Thr Pro
            420                 425                 430

Pro Gln Gln Asn Thr Arg Gln Thr Ala Ala Met Phe Gly Val Val Asn
        435                 440                 445

Val Thr Pro Val Pro Gly Asp Leu Leu Arg Glu Asn Thr Glu Asp Val
    450                 455                 460

Leu Gln Gly Glu His Leu Ser Asp Gln Glu Asn Ala Pro Pro Ile Leu
465                 470                 475                 480

Pro Gly Arg Pro Ser Glu Gly Leu Gly Pro Ser Pro His Leu Val Pro
                485                 490                 495

His Pro Gly Gly Pro Glu Ala Glu Val Trp Glu Glu Thr Asp Val Asn
            500                 505                 510

Arg Asn Lys Leu Arg Ile Asn Ile Gly Lys Ser Pro Cys Val Glu Glu
        515                 520                 525

Glu Gln Ser Arg Gly Met Gly Val Pro Ser Ser Pro Val Arg Ala Pro
    530                 535                 540

Pro Asp Ser Pro Thr Thr Pro Val Arg Ser Leu Arg Tyr Arg Arg Val
545                 550                 555                 560

Asn Ser Pro Glu Ser Glu Arg Leu Ser Thr Ala Asp Gly Arg Val Glu
                565                 570                 575

Leu Pro Glu Arg Arg Trp Val Trp Gly Gln Gly His Gly Trp Gly Pro
            580                 585                 590

Arg Pro Ser Pro Pro Ser Arg Gly Trp Ser Gly Gly Lys Val Arg Cys
        595                 600                 605

Val Ala Glu Val Gly Arg Pro Trp Glu Val Leu Arg Gly Leu Tyr Leu
    610                 615                 620

Gly Leu Gly Ser Asp Ser Val Gly Ala Xaa Asp Arg Ala Trp Glu Asn
625                 630                 635                 640

Gln Trp Gly Ile Gln Arg Gly Pro Gly Ser Cys Gln Glu Thr
                645                 650
```

```
<210> SEQ ID NO 11
<211> LENGTH: 1947
<212> TYPE: DNA
<213> ORGANISM: homo sapiens

<400> SEQUENCE: 11

atgctggcgg cgcggtgcat tgtgggcagc tccccgctct gccgctgccg ccgccgtcgc     60

ccaaggagga tcggggccgg gccgggccgg gatgatccgg gtcggaaggc cgccgccgcc    120

ggagggagcg ggtcacccaa cgccgcactg agccgccccc gccccgcccc ggccccgggg    180

gatgcgccgc cccgagctgc tgcctccgcc gccgccgcag ccgcagccgc agcgggcaca    240
```

-continued

```
gagcaggtag atggcccccct cagggcaggc ccggcggaca cccctccctc tggctggcgg    300

atgcagtgcc tagcggccgc ccttaaggac gaaaccaaca tgagtggggg aggggagcag    360

gccgacatcc tgccggccaa ctacgtggtc aaggatcgct ggaaggtgct gaaaaagatc    420

gggggcgggg gctttggtga gatctacgag gccatggacc tgctgaccag ggagaatgtg    480

gccctcaagg tggagtcagc ccagcagccc aagcaggtcc tcaagatgga ggtggccgtg    540

ctcaagaagt tgcaagggaa ggaccatgtg tgcaggttca ttggctgtgg caggaacgag    600

aagtttaact atgtagtgat gcagctccag ggccggaacc tggccgacct gcgccgtagc    660

cagccgcgag gcaccttcac gctgagcacc acattgcggc tgggcaagca gatcttggag    720

tccatcgagg ccatccactc tgtgggcttc ctgcaccgtg acatcaagcc ttcaaacttt    780

gccatgggca ggctgccctc cacctacagg aagtgctata tgctggactt cgggctggcc    840

cggcagtaca ccaacaccac gggggatgtg cggcccccctc ggaatgtggc cgggtttcga    900

ggaacggttc gctatgcctc agtcaatgcc cacaagaacc gggagatggg ccgccacgac    960

gacctgtggt ccctcttcta catgctggtg gagtttgcag tgggccagct gccctggagg   1020

aagatcaagg acaaggaaca ggtagggatg atcaaggaga agtatgagca ccggatgctg   1080

ctgaagcaca tgccgtcaga gttccacctc ttcctggacc acattgccag cctcgactac   1140

ttcaccaagc ccgactacca gttgatcatg tcagtgtttg agaacagcat gaaggagagg   1200

ggcattgccg agaatgaggc ctttgactgg gagaaggcag gcaccgatgc cctcctgtcc   1260

acgagcacct ctaccccgcc ccagcagaac acccggcaga cggcagccat gtttggggtg   1320

gtcaatgtga cgccagtgcc tggggacctg ctccgggaga acaccgagga tgtgctacag   1380

ggagagcacc tgagtgacca ggagaatgca cccccaattc tgcccgggag gccctctgag   1440

gggctgggcc ccagtcccca ccttgtcccc caccccgggg gtcctgaggc tgaagtctgg   1500

gaggagacag atgtcaaccg gaacaaactc cggatcaaca tcggcaaaag cccctgtgtg   1560

gaggaggaac agagccgagg catgggggtc cccagctccc cagtgcgtgc ccccccagac   1620

tcccccacaa ccccagtccg ttctctgcgc taccggaggg tgaacagccc tgagtcagaa   1680

aggctgtcca cggcggacgg gcgagtggag ctacctgaga ggaggtgggt ctggggccag   1740

gggcatggtt ggggcccaag gccctctccg ccttcacgtg gctggtctgg aggaaaagtt   1800

agatgtgtgg cggaggtggg cagaccctgg gaagtgctga gagggttata cttgggcctg   1860

gggtcagact cagttggggc casagacagg gcctgggara accagtgggg gatccagaga   1920

ggtcccggct catgccagga aacgtaa                                        1947
```

<210> SEQ ID NO 12
<211> LENGTH: 648
<212> TYPE: PRT
<213> ORGANISM: homo sapiens
<220> FEATURE:
<221> NAME/KEY: VARIANT
<222> LOCATION: (1)...(648)
<223> OTHER INFORMATION: Xaa = Any Amino Acid

<400> SEQUENCE: 12

```
Met Leu Ala Ala Arg Cys Ile Val Gly Ser Ser Pro Leu Cys Arg Cys
 1               5                  10                  15

Arg Arg Arg Arg Pro Arg Arg Ile Gly Ala Gly Pro Gly Arg Asp Asp
            20                  25                  30

Pro Gly Arg Lys Ala Ala Ala Ala Gly Gly Ser Gly Ser Pro Asn Ala
        35                  40                  45
```

-continued

```
Ala Leu Ser Arg Pro Arg Pro Ala Pro Ala Pro Gly Asp Ala Pro Pro
    50                  55                  60

Arg Ala Ala Ala Ser Ala Ala Ala Ala Ala Ala Ala Ala Ala Gly Thr
65                  70                  75                  80

Glu Gln Val Asp Gly Pro Leu Arg Ala Gly Pro Ala Asp Thr Pro Pro
                85                  90                  95

Ser Gly Trp Arg Met Gln Cys Leu Ala Ala Ala Leu Lys Asp Glu Thr
            100                 105                 110

Asn Met Ser Gly Gly Gly Glu Gln Ala Asp Ile Leu Pro Ala Asn Tyr
        115                 120                 125

Val Val Lys Asp Arg Trp Lys Val Leu Lys Lys Ile Gly Gly Gly Gly
    130                 135                 140

Phe Gly Glu Ile Tyr Glu Ala Met Asp Leu Leu Thr Arg Glu Asn Val
145                 150                 155                 160

Ala Leu Lys Val Glu Ser Ala Gln Gln Pro Lys Gln Val Leu Lys Met
                165                 170                 175

Glu Val Ala Val Leu Lys Lys Leu Gln Gly Lys Asp His Val Cys Arg
            180                 185                 190

Phe Ile Gly Cys Gly Arg Asn Glu Lys Phe Asn Tyr Val Val Met Gln
        195                 200                 205

Leu Gln Gly Arg Asn Leu Ala Asp Leu Arg Arg Ser Gln Pro Arg Gly
    210                 215                 220

Thr Phe Thr Leu Ser Thr Thr Leu Arg Leu Gly Lys Gln Ile Leu Glu
225                 230                 235                 240

Ser Ile Glu Ala Ile His Ser Val Gly Phe Leu His Arg Asp Ile Lys
                245                 250                 255

Pro Ser Asn Phe Ala Met Gly Arg Leu Pro Ser Thr Tyr Arg Lys Cys
            260                 265                 270

Tyr Met Leu Asp Phe Gly Leu Ala Arg Gln Tyr Thr Asn Thr Thr Gly
        275                 280                 285

Asp Val Arg Pro Pro Arg Asn Val Ala Gly Phe Arg Gly Thr Val Arg
    290                 295                 300

Tyr Ala Ser Val Asn Ala His Lys Asn Arg Glu Met Gly Arg His Asp
305                 310                 315                 320

Asp Leu Trp Ser Leu Phe Tyr Met Leu Val Glu Phe Ala Val Gly Gln
                325                 330                 335

Leu Pro Trp Arg Lys Ile Lys Asp Lys Glu Gln Val Gly Met Ile Lys
            340                 345                 350

Glu Lys Tyr Glu His Arg Met Leu Leu Lys His Met Pro Ser Glu Phe
        355                 360                 365

His Leu Phe Leu Asp His Ile Ala Ser Leu Asp Tyr Phe Thr Lys Pro
    370                 375                 380

Asp Tyr Gln Leu Ile Met Ser Val Phe Glu Asn Ser Met Lys Glu Arg
385                 390                 395                 400

Gly Ile Ala Glu Asn Glu Ala Phe Asp Trp Glu Lys Ala Gly Thr Asp
                405                 410                 415

Ala Leu Leu Ser Thr Ser Thr Ser Thr Pro Pro Gln Gln Asn Thr Arg
            420                 425                 430

Gln Thr Ala Ala Met Phe Gly Val Val Asn Val Thr Pro Val Pro Gly
        435                 440                 445

Asp Leu Leu Arg Glu Asn Thr Glu Asp Val Leu Gln Gly Glu His Leu
    450                 455                 460

Ser Asp Gln Glu Asn Ala Pro Pro Ile Leu Pro Gly Arg Pro Ser Glu
```

-continued

```
465                 470                 475                 480

Gly Leu Gly Pro Ser Pro His Leu Val Pro His Pro Gly Gly Pro Glu
                485                 490                 495

Ala Glu Val Trp Glu Glu Thr Asp Val Asn Arg Asn Lys Leu Arg Ile
            500                 505                 510

Asn Ile Gly Lys Ser Pro Cys Val Glu Glu Glu Gln Ser Arg Gly Met
        515                 520                 525

Gly Val Pro Ser Ser Pro Val Arg Ala Pro Pro Asp Ser Pro Thr Thr
    530                 535                 540

Pro Val Arg Ser Leu Arg Tyr Arg Arg Val Asn Ser Pro Glu Ser Glu
545                 550                 555                 560

Arg Leu Ser Thr Ala Asp Gly Arg Val Glu Leu Pro Glu Arg Arg Trp
                565                 570                 575

Val Trp Gly Gln Gly His Gly Trp Gly Pro Arg Pro Ser Pro Pro Ser
            580                 585                 590

Arg Gly Trp Ser Gly Gly Lys Val Arg Cys Val Ala Glu Val Gly Arg
        595                 600                 605

Pro Trp Glu Val Leu Arg Gly Leu Tyr Leu Gly Leu Gly Ser Asp Ser
    610                 615                 620

Val Gly Ala Xaa Asp Arg Ala Trp Glu Asn Gln Trp Gly Ile Gln Arg
625                 630                 635                 640

Gly Pro Gly Ser Cys Gln Glu Thr
                645


<210> SEQ ID NO 13
<211> LENGTH: 1647
<212> TYPE: DNA
<213> ORGANISM: homo sapiens

<400> SEQUENCE: 13

atgcagtgcc tagcggccgc ccttaaggac gaaaccaaca tgagtggggg aggggagcag     60

gccgacatcc tgccggccaa ctacgtggtc aaggatcgct ggaaggtgct gaaaaagatc    120

gggggcgggg gctttggtga gatctacgag gccatggacc tgctgaccag ggagaatgtg    180

gccctcaagg tggagtcagc ccagcagccc aagcaggtcc tcaagatgga ggtggccgtg    240

ctcaagaagt tgcaagggaa ggaccatgtg tgcaggttca ttggctgtgg caggaacgag    300

aagtttaact atgtagtgat gcagctccag ggccggaacc tggccgacct gcgccgtagc    360

cagccgcgag gcaccttcac gctgagcacc acattgcggc tgggcaagca gatcttggag    420

tccatcgagg ccatccactc tgtgggcttc ctgcaccgtg acatcaagcc ttcaaacttt    480

gccatgggca ggctgccctc cacctacagg aagtgctata tgctggactt cgggctggcc    540

cggcagtaca ccaacaccac gggggatgtg cggcccccctc ggaatgtggc cgggtttcga    600

ggaacggttc gctatgcctc agtcaatgcc cacaagaacc gggagatggg ccgccacgac    660

gacctgtggt ccctcttcta catgctggtg gagtttgcag tgggccagct gccctggagg    720

aagatcaagg acaaggaaca ggtagggatg atcaaggaga agtatgagca ccggatgctg    780

ctgaagcaca tgccgtcaga gttccacctc ttcctggacc acattgccag cctcgactac    840

ttcaccaagc ccgactacca gttgatcatg tcagtgtttg agaacagcat gaaggagagg    900

ggcattgccg agaatgaggc ctttgactgg gagaaggcag gcaccgatgc cctcctgtcc    960

acgagcacct ctaccccgcc ccagcagaac acccggcaga cggcagccat gtttggggtg   1020

gtcaatgtga cgccagtgcc tggggacctg ctccgggaga acaccgagga tgtgctacag   1080
```

-continued

```
ggagagcacc tgagtgacca ggagaatgca cccccaattc tgcccgggag gccctctgag   1140

gggctgggcc ccagtcccca ccttgtcccc caccccgggg gtcctgaggc tgaagtctgg   1200

gaggagacag atgtcaaccg gaacaaactc cggatcaaca tcggcaaaag cccctgtgtg   1260

gaggaggaac agagccgagg catgggggtc cccagctccc cagtgcgtgc ccccccagac   1320

tcccccacaa ccccagtccg ttctctgcgc taccggaggg tgaacagccc tgagtcagaa   1380

aggctgtcca cggcggacgg gcgagtggag ctacctgaga ggaggtgggt ctggggccag   1440

gggcatggtt ggggcccaag gccctctccg ccttcacgtg gctggtctgg aggaaaagtt   1500

agatgtgtgg cggaggtggg cagaccctgg gaagtgctga gagggttata cttgggcctg   1560

gggtcagact cagttggggc casagacagg gcctgggara accagtgggg gatccagaga   1620

ggtcccggct catgccagga aacgtaa                                       1647


<210> SEQ ID NO 14
<211> LENGTH: 548
<212> TYPE: PRT
<213> ORGANISM: homo sapiens
<220> FEATURE:
<221> NAME/KEY: VARIANT
<222> LOCATION: (1)...(548)
<223> OTHER INFORMATION: Xaa = Any Amino Acid

<400> SEQUENCE: 14

Met Gln Cys Leu Ala Ala Ala Leu Lys Asp Glu Thr Asn Met Ser Gly
 1               5                  10                  15

Gly Gly Glu Gln Ala Asp Ile Leu Pro Ala Asn Tyr Val Val Lys Asp
            20                  25                  30

Arg Trp Lys Val Leu Lys Lys Ile Gly Gly Gly Gly Phe Gly Glu Ile
        35                  40                  45

Tyr Glu Ala Met Asp Leu Leu Thr Arg Glu Asn Val Ala Leu Lys Val
    50                  55                  60

Glu Ser Ala Gln Gln Pro Lys Gln Val Leu Lys Met Glu Val Ala Val
65                  70                  75                  80

Leu Lys Lys Leu Gln Gly Lys Asp His Val Cys Arg Phe Ile Gly Cys
                85                  90                  95

Gly Arg Asn Glu Lys Phe Asn Tyr Val Val Met Gln Leu Gln Gly Arg
            100                 105                 110

Asn Leu Ala Asp Leu Arg Arg Ser Gln Pro Arg Gly Thr Phe Thr Leu
        115                 120                 125

Ser Thr Thr Leu Arg Leu Gly Lys Gln Ile Leu Glu Ser Ile Glu Ala
    130                 135                 140

Ile His Ser Val Gly Phe Leu His Arg Asp Ile Lys Pro Ser Asn Phe
145                 150                 155                 160

Ala Met Gly Arg Leu Pro Ser Thr Tyr Arg Lys Cys Tyr Met Leu Asp
                165                 170                 175

Phe Gly Leu Ala Arg Gln Tyr Thr Asn Thr Thr Gly Asp Val Arg Pro
            180                 185                 190

Pro Arg Asn Val Ala Gly Phe Arg Gly Thr Val Arg Tyr Ala Ser Val
        195                 200                 205

Asn Ala His Lys Asn Arg Glu Met Gly Arg His Asp Asp Leu Trp Ser
    210                 215                 220

Leu Phe Tyr Met Leu Val Glu Phe Ala Val Gly Gln Leu Pro Trp Arg
225                 230                 235                 240

Lys Ile Lys Asp Lys Glu Gln Val Gly Met Ile Lys Glu Lys Tyr Glu
                245                 250                 255
```

```
His Arg Met Leu Leu Lys His Met Pro Ser Glu Phe His Leu Phe Leu
            260                 265                 270

Asp His Ile Ala Ser Leu Asp Tyr Phe Thr Lys Pro Asp Tyr Gln Leu
        275                 280                 285

Ile Met Ser Val Phe Glu Asn Ser Met Lys Glu Arg Gly Ile Ala Glu
    290                 295                 300

Asn Glu Ala Phe Asp Trp Glu Lys Ala Gly Thr Asp Ala Leu Leu Ser
305                 310                 315                 320

Thr Ser Thr Ser Thr Pro Pro Gln Gln Asn Thr Arg Gln Thr Ala Ala
                325                 330                 335

Met Phe Gly Val Val Asn Val Thr Pro Val Pro Gly Asp Leu Leu Arg
            340                 345                 350

Glu Asn Thr Glu Asp Val Leu Gln Gly Glu His Leu Ser Asp Gln Glu
        355                 360                 365

Asn Ala Pro Pro Ile Leu Pro Gly Arg Pro Ser Glu Gly Leu Gly Pro
    370                 375                 380

Ser Pro His Leu Val Pro His Pro Gly Gly Pro Glu Ala Glu Val Trp
385                 390                 395                 400

Glu Glu Thr Asp Val Asn Arg Asn Lys Leu Arg Ile Asn Ile Gly Lys
                405                 410                 415

Ser Pro Cys Val Glu Glu Glu Gln Ser Arg Gly Met Gly Val Pro Ser
            420                 425                 430

Ser Pro Val Arg Ala Pro Pro Asp Ser Pro Thr Thr Pro Val Arg Ser
        435                 440                 445

Leu Arg Tyr Arg Arg Val Asn Ser Pro Glu Ser Glu Arg Leu Ser Thr
    450                 455                 460

Ala Asp Gly Arg Val Glu Leu Pro Glu Arg Arg Trp Val Trp Gly Gln
465                 470                 475                 480

Gly His Gly Trp Gly Pro Arg Pro Ser Pro Pro Ser Arg Gly Trp Ser
                485                 490                 495

Gly Gly Lys Val Arg Cys Val Ala Glu Val Gly Arg Pro Trp Glu Val
            500                 505                 510

Leu Arg Gly Leu Tyr Leu Gly Leu Gly Ser Asp Ser Val Gly Ala Xaa
        515                 520                 525

Asp Arg Ala Trp Glu Asn Gln Trp Gly Ile Gln Arg Gly Pro Gly Ser
    530                 535                 540

Cys Gln Glu Thr
545
```

```
<210> SEQ ID NO 15
<211> LENGTH: 1608
<212> TYPE: DNA
<213> ORGANISM: homo sapiens

<400> SEQUENCE: 15

atgagtgggg gaggggagca ggccgacatc ctgccggcca actacgtggt caaggatcgc     60

tggaaggtgc tgaaaaagat cgggggcggg ggctttggtg agatctacga ggccatggac    120

ctgctgacca gggagaatgt ggccctcaag gtggagtcag cccagcagcc caagcaggtc    180

ctcaagatgg aggtggccgt gctcaagaag ttgcaaggga aggaccatgt gtgcaggttc    240

attggctgtg gcaggaacga gaagtttaac tatgtagtga tgcagctcca gggccggaac    300

ctggccgacc tgcgccgtag ccagccgcga ggcaccttca cgctgagcac cacattgcgg    360

ctgggcaagc agatcttgga gtccatcgag gccatccact ctgtgggctt cctgcaccgt    420
```

```
gacatcaagc cttcaaactt tgccatgggc aggctgccct ccacctacag gaagtgctat    480

atgctggact tcgggctggc ccggcagtac accaacacca cgggggatgt gcggcccccct   540

cggaatgtgg ccgggtttcg aggaacggtt cgctatgcct cagtcaatgc ccacaagaac    600

cgggagatgg gccgccacga cgacctgtgg tccctcttct acatgctggt ggagtttgca    660

gtgggccagc tgccctggag gaagatcaag gacaaggaac aggtagggat gatcaaggag    720

aagtatgagc accggatgct gctgaagcac atgccgtcag agttccacct cttcctggac    780

cacattgcca gcctcgacta cttcaccaag cccgactacc agttgatcat gtcagtgttt    840

gagaacagca tgaaggagag ggcattgcc gagaatgagg cctttgactg ggagaaggca    900

ggcaccgatg ccctcctgtc cacgagcacc tctaccccgc cccagcagaa cacccggcag    960

acggcagcca tgtttggggt ggtcaatgtg acgccagtgc ctggggacct gctccgggag   1020

aacaccgagg atgtgctaca gggagagcac ctgagtgacc aggagaatgc acccccaatt   1080

ctgcccggga ggccctctga ggggctgggc cccagtcccc accttgtccc ccaccccggg   1140

ggtcctgagg ctgaagtctg ggaggagaca gatgtcaacc ggaacaaact ccggatcaac   1200

atcggcaaaa gcccctgtgt ggaggaggaa cagagccgag gcatgggggt ccccagctcc   1260

ccagtgcgtg cccccccaga ctcccccaca accccagtcc gttctctgcg ctaccggagg   1320

gtgaacagcc ctgagtcaga aaggctgtcc acggcggacg ggcgagtgga gctacctgag   1380

aggaggtggg tctggggcca ggggcatggt tggggcccaa ggccctctcc gccttcacgt   1440

ggctggtctg gaggaaaagt tagatgtgtg gcggaggtgg gcagaccctg ggaagtgctg   1500

agagggttat acttgggcct ggggtcagac tcagttgggg ccasagacag ggcctgggar   1560

aaccagtggg ggatccagag aggtcccggc tcatgccagg aaacgtaa                1608
```

<210> SEQ ID NO 16
<211> LENGTH: 535
<212> TYPE: PRT
<213> ORGANISM: homo sapiens
<220> FEATURE:
<221> NAME/KEY: VARIANT
<222> LOCATION: (1)...(535)
<223> OTHER INFORMATION: Xaa = Any Amino Acid

<400> SEQUENCE: 16

```
Met Ser Gly Gly Gly Glu Gln Ala Asp Ile Leu Pro Ala Asn Tyr Val
 1               5                  10                  15

Val Lys Asp Arg Trp Lys Val Leu Lys Lys Ile Gly Gly Gly Gly Phe
            20                  25                  30

Gly Glu Ile Tyr Glu Ala Met Asp Leu Leu Thr Arg Glu Asn Val Ala
        35                  40                  45

Leu Lys Val Glu Ser Ala Gln Gln Pro Lys Gln Val Leu Lys Met Glu
    50                  55                  60

Val Ala Val Leu Lys Lys Leu Gln Gly Lys Asp His Val Cys Arg Phe
65                  70                  75                  80

Ile Gly Cys Gly Arg Asn Glu Lys Phe Asn Tyr Val Val Met Gln Leu
                85                  90                  95

Gln Gly Arg Asn Leu Ala Asp Leu Arg Arg Ser Gln Pro Arg Gly Thr
            100                 105                 110

Phe Thr Leu Ser Thr Thr Leu Arg Leu Gly Lys Gln Ile Leu Glu Ser
        115                 120                 125

Ile Glu Ala Ile His Ser Val Gly Phe Leu His Arg Asp Ile Lys Pro
    130                 135                 140
```

-continued

```
Ser Asn Phe Ala Met Gly Arg Leu Pro Ser Thr Tyr Arg Lys Cys Tyr
145                 150                 155                 160

Met Leu Asp Phe Gly Leu Ala Arg Gln Tyr Thr Asn Thr Thr Gly Asp
                165                 170                 175

Val Arg Pro Pro Arg Asn Val Ala Gly Phe Arg Gly Thr Val Arg Tyr
            180                 185                 190

Ala Ser Val Asn Ala His Lys Asn Arg Glu Met Gly Arg His Asp Asp
        195                 200                 205

Leu Trp Ser Leu Phe Tyr Met Leu Val Glu Phe Ala Val Gly Gln Leu
    210                 215                 220

Pro Trp Arg Lys Ile Lys Asp Lys Glu Gln Val Gly Met Ile Lys Glu
225                 230                 235                 240

Lys Tyr Glu His Arg Met Leu Leu Lys His Met Pro Ser Glu Phe His
                245                 250                 255

Leu Phe Leu Asp His Ile Ala Ser Leu Asp Tyr Phe Thr Lys Pro Asp
            260                 265                 270

Tyr Gln Leu Ile Met Ser Val Phe Glu Asn Ser Met Lys Glu Arg Gly
        275                 280                 285

Ile Ala Glu Asn Glu Ala Phe Asp Trp Glu Lys Ala Gly Thr Asp Ala
    290                 295                 300

Leu Leu Ser Thr Ser Thr Ser Thr Pro Pro Gln Gln Asn Thr Arg Gln
305                 310                 315                 320

Thr Ala Ala Met Phe Gly Val Val Asn Val Thr Pro Val Pro Gly Asp
                325                 330                 335

Leu Leu Arg Glu Asn Thr Glu Asp Val Leu Gln Gly Glu His Leu Ser
            340                 345                 350

Asp Gln Glu Asn Ala Pro Pro Ile Leu Pro Gly Arg Pro Ser Glu Gly
        355                 360                 365

Leu Gly Pro Ser Pro His Leu Val Pro His Pro Gly Gly Pro Glu Ala
    370                 375                 380

Glu Val Trp Glu Glu Thr Asp Val Asn Arg Asn Lys Leu Arg Ile Asn
385                 390                 395                 400

Ile Gly Lys Ser Pro Cys Val Glu Glu Glu Gln Ser Arg Gly Met Gly
                405                 410                 415

Val Pro Ser Ser Pro Val Arg Ala Pro Pro Asp Ser Pro Thr Thr Pro
            420                 425                 430

Val Arg Ser Leu Arg Tyr Arg Arg Val Asn Ser Pro Glu Ser Glu Arg
        435                 440                 445

Leu Ser Thr Ala Asp Gly Arg Val Glu Leu Pro Glu Arg Arg Trp Val
    450                 455                 460

Trp Gly Gln Gly His Gly Trp Gly Pro Arg Pro Ser Pro Pro Ser Arg
465                 470                 475                 480

Gly Trp Ser Gly Gly Lys Val Arg Cys Val Ala Glu Val Gly Arg Pro
                485                 490                 495

Trp Glu Val Leu Arg Gly Leu Tyr Leu Gly Leu Gly Ser Asp Ser Val
            500                 505                 510

Gly Ala Xaa Asp Arg Ala Trp Glu Asn Gln Trp Gly Ile Gln Arg Gly
        515                 520                 525

Pro Gly Ser Cys Gln Glu Thr
    530                 535

<210> SEQ ID NO 17
<211> LENGTH: 2688
```

<212> TYPE: DNA
<213> ORGANISM: homo sapiens

<400> SEQUENCE: 17

```
atgtcagggc tggtgctgat gctggcggcg cggtgcattg tgggcagctc cccgctctgc     60
cgctgccgcc gccgtcgccc aaggaggatc ggggccgggc cgggccggga tgatccgggt    120
cggaaggccg ccgccgccgg agggagcggg tcacccaacg ccgcactgag ccgcccccgc    180
cccgccccgg ccccggggga tgcgccgccc cgagctgctg cctccgccgc cgccgcagcc    240
gcagccgcag cgggcacaga gcaggtagat ggcccccctca gggcaggccc ggcggacacc    300
cctccctctg gctggcggat gcagtgccta gcggccgccc ttaaggacga aaccaacatg    360
agtgggggag gggagcaggc cgacatcctg ccggccaact acgtggtcaa ggatcgctgg    420
aaggtgctga aaaagatcgg gggcgggggc tttggtgaga tctacgaggc catggacctg    480
ctgaccaggg agaatgtggc cctcaaggtg gagtcagccc agcagcccaa gcaggtcctc    540
aagatggagg tggccgtgct caagaagttg caagggaagg accatgtgtg caggttcatt    600
ggctgtggca ggaacgagaa gtttaactat gtagtgatgc agctccaggg ccggaacctg    660
gccgacctgc gccgtagcca gccgcgaggc accttcacgc tgagcaccac attgcggctg    720
ggcaagcaga tcttggagtc catcgaggcc atccactctg tgggcttcct gcaccgtgac    780
atcaagcctt caaactttgc catgggcagg ctgccctcca cctacaggaa gtgctatatg    840
ctggacttcg ggctggcccg gcagtacacc aacaccacgg gggatgtgcg gccccctcgg    900
aatgtggccg ggtttcgagg aacggttcgc tatgcctcag tcaatgccca caagaaccgg    960
gagatgggcc gccacgacga cctgtggtcc ctcttctaca tgctggtgga gtttgcagtg   1020
ggccagctgc cctggaggaa gatcaaggac aaggaacagg tagggatgat caaggagaag   1080
tatgagcacc ggatgctgct gaagcacatg ccgtcagagt tccacctctt cctggaccac   1140
attgccagcc tcgactactt caccaagccc gactaccagt tgatcatgtc agtgtttgag   1200
aacagcatga aggagagggg cattgccgag aatgaggcct ttgactggga gaaggcaggc   1260
accgatgccc tcctgtccac gagcacctct accccgcccc agcagaacac ccggcagacg   1320
gcagccatgt ttggggtggt caatgtgacg ccagtgcctg ggacctgct ccgggagaac    1380
accgaggatg tgctacaggg agagcacctg agtgaccagg agaatgcacc cccaattctg   1440
cccgggaggc cctctgaggg gctgggcccc agtccccacc ttgtccccca ccccgggggt   1500
cctgaggctg aagtctggga ggagacagat gtcaaccgga acaaactccg gatcaacatc   1560
ggcaaaagcc cctgtgtgga ggaggaacag agccgaggca tgggggtccc cagctcccca   1620
gtgcgtgccc ccccagactc cccccacaacc ccagtccgtt ctctgcgcta ccggagggtg  1680
aacagccctg agtcagaaag gctgtccacg gcggacgggc gagtggagct acctgagagg   1740
aggtcacgga tggatctgcc tggctcgccc tcgcgccagg cctgctcctc tcagccagcc   1800
cagatgctgt cagtggacac aggccacgct gaccgacagg ccagtggccg catggaygtg   1860
tcagcctctg tggagcagga ggccctgagc aacgccttcc gctcggtgcc gctggctgag   1920
gaggaggatt tcgacagcaa agagtgggtc atcatcgaca aggagacgga gctcaaggac   1980
ttccctccag ggctgagcc cagcacatcg ggcaccacgg atgaggagcc cgaggagctg    2040
cggccactgc ccgaggaggg cgaagagcgg cggcggctgg gggcagagcc caccgtccgg   2100
ccccggggac gcagcatgca ggcgctggcg gaggaggacc tgcagcattt gccgccccag   2160
cccctgccac cccagctgag ccaggscgat ggccgttccg agacgtcaca gccccccacg   2220
```

-continued

```
cctggcagcc cttcccactc acccctgcac tcgggacccc gccctcgacg gagagagtcg   2280

gaccccacag gcccacagag acaggctgga gtgcaatggc gtgatctcgg ctcactgcaa   2340

cctccacctc ccaggttcaa gcaattctcc tgcctcagcc tcccgagaag ctgggattac   2400

aggcatgcac caccaccaca cccggctaat tttgtatttt tagtagagac ggggtttctc   2460

catgttgagg ctggtcttga gctcctgacc tcaggtgatc tgcctgcctc ggcctcccaa   2520

attgctggga ttacaggcgt gagccatcgc gcccagcctg aggtctgtga gtttaacaga   2580

aaacatacag gccagagaga gcagatggtt tgtgcaggat cagagagagc ctggagcatg   2640

cgtgacctgc ccgggcggcc gctcgagccc tatagtgagt cgtattag               2688
```

```
<210> SEQ ID NO 18
<211> LENGTH: 895
<212> TYPE: PRT
<213> ORGANISM: homo sapiens
<220> FEATURE:
<221> NAME/KEY: VARIANT
<222> LOCATION: (1)...(895)
<223> OTHER INFORMATION: Xaa = Any Amino Acid

<400> SEQUENCE: 18

Met Ser Gly Leu Val Leu Met Leu Ala Ala Arg Cys Ile Val Gly Ser
 1               5                  10                  15

Ser Pro Leu Cys Arg Cys Arg Arg Arg Arg Pro Arg Arg Ile Gly Ala
            20                  25                  30

Gly Pro Gly Arg Asp Asp Pro Gly Arg Lys Ala Ala Ala Ala Gly Gly
        35                  40                  45

Ser Gly Ser Pro Asn Ala Ala Leu Ser Arg Pro Arg Pro Ala Pro Ala
    50                  55                  60

Pro Gly Asp Ala Pro Pro Arg Ala Ala Ala Ser Ala Ala Ala Ala Ala
65                  70                  75                  80

Ala Ala Ala Ala Gly Thr Glu Gln Val Asp Gly Pro Leu Arg Ala Gly
                85                  90                  95

Pro Ala Asp Thr Pro Pro Ser Gly Trp Arg Met Gln Cys Leu Ala Ala
            100                 105                 110

Ala Leu Lys Asp Glu Thr Asn Met Ser Gly Gly Gly Glu Gln Ala Asp
        115                 120                 125

Ile Leu Pro Ala Asn Tyr Val Val Lys Asp Arg Trp Lys Val Leu Lys
    130                 135                 140

Lys Ile Gly Gly Gly Gly Phe Gly Glu Ile Tyr Glu Ala Met Asp Leu
145                 150                 155                 160

Leu Thr Arg Glu Asn Val Ala Leu Lys Val Glu Ser Ala Gln Gln Pro
                165                 170                 175

Lys Gln Val Leu Lys Met Glu Val Ala Val Leu Lys Lys Leu Gln Gly
            180                 185                 190

Lys Asp His Val Cys Arg Phe Ile Gly Cys Gly Arg Asn Glu Lys Phe
        195                 200                 205

Asn Tyr Val Val Met Gln Leu Gln Gly Arg Asn Leu Ala Asp Leu Arg
    210                 215                 220

Arg Ser Gln Pro Arg Gly Thr Phe Thr Leu Ser Thr Thr Leu Arg Leu
225                 230                 235                 240

Gly Lys Gln Ile Leu Glu Ser Ile Glu Ala Ile His Ser Val Gly Phe
                245                 250                 255

Leu His Arg Asp Ile Lys Pro Ser Asn Phe Ala Met Gly Arg Leu Pro
            260                 265                 270
```

-continued

```
Ser Thr Tyr Arg Lys Cys Tyr Met Leu Asp Phe Gly Leu Ala Arg Gln
        275                 280                 285

Tyr Thr Asn Thr Thr Gly Asp Val Arg Pro Pro Arg Asn Val Ala Gly
    290                 295                 300

Phe Arg Gly Thr Val Arg Tyr Ala Ser Val Asn Ala His Lys Asn Arg
305                 310                 315                 320

Glu Met Gly Arg His Asp Asp Leu Trp Ser Leu Phe Tyr Met Leu Val
                325                 330                 335

Glu Phe Ala Val Gly Gln Leu Pro Trp Arg Lys Ile Lys Asp Lys Glu
            340                 345                 350

Gln Val Gly Met Ile Lys Glu Lys Tyr Glu His Arg Met Leu Leu Lys
        355                 360                 365

His Met Pro Ser Glu Phe His Leu Phe Leu Asp His Ile Ala Ser Leu
    370                 375                 380

Asp Tyr Phe Thr Lys Pro Asp Tyr Gln Leu Ile Met Ser Val Phe Glu
385                 390                 395                 400

Asn Ser Met Lys Glu Arg Gly Ile Ala Glu Asn Glu Ala Phe Asp Trp
                405                 410                 415

Glu Lys Ala Gly Thr Asp Ala Leu Leu Ser Thr Ser Thr Ser Thr Pro
            420                 425                 430

Pro Gln Gln Asn Thr Arg Gln Thr Ala Ala Met Phe Gly Val Val Asn
        435                 440                 445

Val Thr Pro Val Pro Gly Asp Leu Leu Arg Glu Asn Thr Glu Asp Val
    450                 455                 460

Leu Gln Gly Glu His Leu Ser Asp Gln Glu Asn Ala Pro Pro Ile Leu
465                 470                 475                 480

Pro Gly Arg Pro Ser Glu Gly Leu Gly Pro Ser Pro His Leu Val Pro
                485                 490                 495

His Pro Gly Gly Pro Glu Ala Glu Val Trp Glu Glu Thr Asp Val Asn
            500                 505                 510

Arg Asn Lys Leu Arg Ile Asn Ile Gly Lys Ser Pro Cys Val Glu Glu
        515                 520                 525

Glu Gln Ser Arg Gly Met Gly Val Pro Ser Ser Pro Val Arg Ala Pro
    530                 535                 540

Pro Asp Ser Pro Thr Thr Pro Val Arg Ser Leu Arg Tyr Arg Arg Val
545                 550                 555                 560

Asn Ser Pro Glu Ser Glu Arg Leu Ser Thr Ala Asp Gly Arg Val Glu
                565                 570                 575

Leu Pro Glu Arg Arg Ser Arg Met Asp Leu Pro Gly Ser Pro Ser Arg
            580                 585                 590

Gln Ala Cys Ser Ser Gln Pro Ala Gln Met Leu Ser Val Asp Thr Gly
        595                 600                 605

His Ala Asp Arg Gln Ala Ser Gly Arg Met Asp Val Ser Ala Ser Val
    610                 615                 620

Glu Gln Glu Ala Leu Ser Asn Ala Phe Arg Ser Val Pro Leu Ala Glu
625                 630                 635                 640

Glu Glu Asp Phe Asp Ser Lys Glu Trp Val Ile Ile Asp Lys Glu Thr
                645                 650                 655

Glu Leu Lys Asp Phe Pro Pro Gly Ala Glu Pro Ser Thr Ser Gly Thr
            660                 665                 670

Thr Asp Glu Glu Pro Glu Glu Leu Arg Pro Leu Pro Glu Glu Gly Glu
        675                 680                 685

Glu Arg Arg Arg Leu Gly Ala Glu Pro Thr Val Arg Pro Arg Gly Arg
```

-continued

```
    690                 695                 700

Ser Met Gln Ala Leu Ala Glu Glu Asp Leu Gln His Leu Pro Pro Gln
705                 710                 715                 720

Pro Leu Pro Pro Gln Leu Ser Gln Xaa Asp Gly Arg Ser Glu Thr Ser
                725                 730                 735

Gln Pro Pro Thr Pro Gly Ser Pro Ser His Ser Pro Leu His Ser Gly
            740                 745                 750

Pro Arg Pro Arg Arg Arg Glu Ser Asp Pro Thr Gly Pro Gln Arg Gln
        755                 760                 765

Ala Gly Val Gln Trp Arg Asp Leu Gly Ser Leu Gln Pro Pro Pro Pro
    770                 775                 780

Arg Phe Lys Gln Phe Ser Cys Leu Ser Leu Pro Arg Ser Trp Asp Tyr
785                 790                 795                 800

Arg His Ala Pro Pro Pro His Pro Ala Asn Phe Val Phe Leu Val Glu
                805                 810                 815

Thr Gly Phe Leu His Val Glu Ala Gly Leu Glu Leu Leu Thr Ser Gly
            820                 825                 830

Asp Leu Pro Ala Ser Ala Ser Gln Ile Ala Gly Ile Thr Gly Val Ser
        835                 840                 845

His Arg Ala Gln Pro Glu Val Cys Glu Phe Asn Arg Lys His Thr Gly
    850                 855                 860

Gln Arg Glu Gln Met Val Cys Ala Gly Ser Glu Arg Ala Trp Ser Met
865                 870                 875                 880

Arg Asp Leu Pro Gly Arg Pro Leu Glu Pro Tyr Ser Glu Ser Tyr
                885                 890                 895
```

<210> SEQ ID NO 19
<211> LENGTH: 2670
<212> TYPE: DNA
<213> ORGANISM: homo sapiens

<400> SEQUENCE: 19

```
atgctggcgg cgcggtgcat tgtgggcagc tccccgctct gccgctgccg ccgccgtcgc     60

ccaaggagga tcggggccgg gccgggccgg gatgatccgg gtcggaaggc cgccgccgcc    120

ggagggagcg ggtcacccaa cgccgcactg agccgccccc gccccgcccc ggccccgggg    180

gatgcgccgc cccgagctgc tgcctccgcc gccgccgcag ccgcagccgc agcgggcaca    240

gagcaggtag atggccccct cagggcaggc ccggcggaca cccctccctc tggctggcgg    300

atgcagtgcc tagcggccgc ccttaaggac gaaaccaaca tgagtggggg aggggagcag    360

gccgacatcc tgccggccaa ctacgtggtc aaggatcgct ggaaggtgct gaaaaagatc    420

gggggcgggg gctttggtga gatctacgag gccatggacc tgctgaccag ggagaatgtg    480

gccctcaagg tggagtcagc ccagcagccc aagcaggtcc tcaagatgga ggtggccgtg    540

ctcaagaagt tgcaagggaa ggaccatgtg tgcaggttca ttggctgtgg caggaacgag    600

aagtttaact atgtagtgat gcagctccag ggccggaacc tggccgacct gcgccgtagc    660

cagccgcgag gcaccttcac gctgagcacc acattgcggc tgggcaagca gatcttggag    720

tccatcgagg ccatccactc tgtgggcttc ctgcaccgtg acatcaagcc ttcaaacttt    780

gccatgggca ggctgccctc cacctacagg aagtgctata tgctggactt cgggctggcc    840

cggcagtaca ccaacaccac gggggatgtg cggccccctc ggaatgtggc cgggtttcga    900

ggaacggttc gctatgcctc agtcaatgcc cacaagaacc gggagatggg ccgccacgac    960

gacctgtggt ccctcttcta catgctggtg gagtttgcag tgggccagct gccctggagg   1020
```

-continued

```
aagatcaagg acaaggaaca ggtagggatg atcaaggaga agtatgagca ccggatgctg   1080
ctgaagcaca tgccgtcaga gttccacctc ttcctggacc acattgccag cctcgactac   1140
ttcaccaagc ccgactacca gttgatcatg tcagtgtttg agaacagcat gaaggagagg   1200
ggcattgccg agaatgaggc ctttgactgg gagaaggcag gcaccgatgc cctcctgtcc   1260
acgagcacct ctaccccgcc ccagcagaac acccggcaga cggcagccat gtttggggtg   1320
gtcaatgtga cgccagtgcc tggggacctg ctccgggaga acaccgagga tgtgctacag   1380
ggagagcacc tgagtgacca ggagaatgca cccccaattc tgcccgggag gccctctgag   1440
gggctgggcc ccagtcccca ccttgtcccc caccccgggg gtcctgaggc tgaagtctgg   1500
gaggagacag atgtcaaccg gaacaaactc cggatcaaca tcggcaaaag cccctgtgtg   1560
gaggaggaac agagccgagg catgggggtc cccagctccc cagtgcgtgc ccccccagac   1620
tcccccacaa ccccagtccg ttctctgcgc taccggaggg tgaacagccc tgagtcagaa   1680
aggctgtcca cggcggacgg gcgagtggag ctacctgaga ggaggtcacg gatggatctg   1740
cctggctcgc cctcgcgcca ggcctgctcc tctcagccag cccagatgct gtcagtggac   1800
acaggccacg ctgaccgaca ggccagtggc cgcatggayg tgtcagcctc tgtggagcag   1860
gaggccctga gcaacgcctt ccgctcggtg ccgctggctg aggaggagga tttcgacagc   1920
aaagagtggg tcatcatcga caaggagacg gagctcaagg acttccctcc aggggctgag   1980
cccagcacat cgggcaccac ggatgaggag cccgaggagc tgcggccact gcccgaggag   2040
ggcgaagagc ggcggcggct gggggcagag cccaccgtcc ggccccgggg acgcagcatg   2100
caggcgctgg cggaggagga cctgcagcat ttgccgcccc agcccctgcc accccagctg   2160
agccaggscg atggccgttc cgagacgtca cagcccccca cgcctggcag cccttcccac   2220
tcacccctgc actcgggacc ccgccctcga cggagagagt cggaccccac aggcccacag   2280
agacaggctg gagtgcaatg gcgtgatctc ggctcactgc aacctccacc tcccaggttc   2340
aagcaattct cctgcctcag cctcccgaga agctgggatt acaggcatgc accaccacca   2400
cacccggcta attttgtatt tttagtagag acggggtttc tccatgttga ggctggtctt   2460
gagctcctga cctcaggtga tctgcctgcc tcggcctccc aaattgctgg gattacaggc   2520
gtgagccatc gcgcccagcc tgaggtctgt gagtttaaca gaaaacatac aggccagaga   2580
gagcagatgg tttgtgcagg atcagagaga gcctggagca tgcgtgacct gcccgggcgg   2640
ccgctcgagc cctatagtga gtcgtattag                                    2670
```

```
<210> SEQ ID NO 20
<211> LENGTH: 889
<212> TYPE: PRT
<213> ORGANISM: homo sapiens
<220> FEATURE:
<221> NAME/KEY: VARIANT
<222> LOCATION: (1)...(889)
<223> OTHER INFORMATION: Xaa = Any Amino Acid

<400> SEQUENCE: 20

Met Leu Ala Ala Arg Cys Ile Val Gly Ser Ser Pro Leu Cys Arg Cys
 1               5                  10                  15

Arg Arg Arg Arg Pro Arg Arg Ile Gly Ala Gly Pro Gly Arg Asp Asp
            20                  25                  30

Pro Gly Arg Lys Ala Ala Ala Ala Gly Gly Ser Gly Ser Pro Asn Ala
        35                  40                  45

Ala Leu Ser Arg Pro Arg Pro Ala Pro Ala Pro Gly Asp Ala Pro Pro
```

-continued

```
    50                  55                  60

Arg Ala Ala Ala Ser Ala Ala Ala Ala Ala Ala Ala Ala Ala Gly Thr
65                  70                  75                  80

Glu Gln Val Asp Gly Pro Leu Arg Ala Gly Pro Ala Asp Thr Pro Pro
                85                  90                  95

Ser Gly Trp Arg Met Gln Cys Leu Ala Ala Ala Leu Lys Asp Glu Thr
            100                 105                 110

Asn Met Ser Gly Gly Gly Glu Gln Ala Asp Ile Leu Pro Ala Asn Tyr
        115                 120                 125

Val Val Lys Asp Arg Trp Lys Val Leu Lys Lys Ile Gly Gly Gly Gly
    130                 135                 140

Phe Gly Glu Ile Tyr Glu Ala Met Asp Leu Leu Thr Arg Glu Asn Val
145                 150                 155                 160

Ala Leu Lys Val Glu Ser Ala Gln Gln Pro Lys Gln Val Leu Lys Met
                165                 170                 175

Glu Val Ala Val Leu Lys Lys Leu Gln Gly Lys Asp His Val Cys Arg
            180                 185                 190

Phe Ile Gly Cys Gly Arg Asn Glu Lys Phe Asn Tyr Val Val Met Gln
        195                 200                 205

Leu Gln Gly Arg Asn Leu Ala Asp Leu Arg Arg Ser Gln Pro Arg Gly
    210                 215                 220

Thr Phe Thr Leu Ser Thr Thr Leu Arg Leu Gly Lys Gln Ile Leu Glu
225                 230                 235                 240

Ser Ile Glu Ala Ile His Ser Val Gly Phe Leu His Arg Asp Ile Lys
                245                 250                 255

Pro Ser Asn Phe Ala Met Gly Arg Leu Pro Ser Thr Tyr Arg Lys Cys
            260                 265                 270

Tyr Met Leu Asp Phe Gly Leu Ala Arg Gln Tyr Thr Asn Thr Thr Gly
        275                 280                 285

Asp Val Arg Pro Pro Arg Asn Val Ala Gly Phe Arg Gly Thr Val Arg
    290                 295                 300

Tyr Ala Ser Val Asn Ala His Lys Asn Arg Glu Met Gly Arg His Asp
305                 310                 315                 320

Asp Leu Trp Ser Leu Phe Tyr Met Leu Val Glu Phe Ala Val Gly Gln
                325                 330                 335

Leu Pro Trp Arg Lys Ile Lys Asp Lys Glu Gln Val Gly Met Ile Lys
            340                 345                 350

Glu Lys Tyr Glu His Arg Met Leu Leu Lys His Met Pro Ser Glu Phe
        355                 360                 365

His Leu Phe Leu Asp His Ile Ala Ser Leu Asp Tyr Phe Thr Lys Pro
    370                 375                 380

Asp Tyr Gln Leu Ile Met Ser Val Phe Glu Asn Ser Met Lys Glu Arg
385                 390                 395                 400

Gly Ile Ala Glu Asn Glu Ala Phe Asp Trp Glu Lys Ala Gly Thr Asp
                405                 410                 415

Ala Leu Leu Ser Thr Ser Thr Ser Thr Pro Pro Gln Gln Asn Thr Arg
            420                 425                 430

Gln Thr Ala Ala Met Phe Gly Val Val Asn Val Thr Pro Val Pro Gly
        435                 440                 445

Asp Leu Leu Arg Glu Asn Thr Glu Asp Val Leu Gln Gly Glu His Leu
    450                 455                 460

Ser Asp Gln Glu Asn Ala Pro Pro Ile Leu Pro Gly Arg Pro Ser Glu
465                 470                 475                 480
```

-continued

```
Gly Leu Gly Pro Ser Pro His Leu Val Pro His Pro Gly Gly Pro Glu
                485                 490                 495

Ala Glu Val Trp Glu Glu Thr Asp Val Asn Arg Asn Lys Leu Arg Ile
            500                 505                 510

Asn Ile Gly Lys Ser Pro Cys Val Glu Glu Glu Gln Ser Arg Gly Met
        515                 520                 525

Gly Val Pro Ser Ser Pro Val Arg Ala Pro Pro Asp Ser Pro Thr Thr
    530                 535                 540

Pro Val Arg Ser Leu Arg Tyr Arg Arg Val Asn Ser Pro Glu Ser Glu
545                 550                 555                 560

Arg Leu Ser Thr Ala Asp Gly Arg Val Glu Leu Pro Glu Arg Arg Ser
                565                 570                 575

Arg Met Asp Leu Pro Gly Ser Pro Ser Arg Gln Ala Cys Ser Ser Gln
            580                 585                 590

Pro Ala Gln Met Leu Ser Val Asp Thr Gly His Ala Asp Arg Gln Ala
        595                 600                 605

Ser Gly Arg Met Asp Val Ser Ala Ser Val Glu Gln Glu Ala Leu Ser
    610                 615                 620

Asn Ala Phe Arg Ser Val Pro Leu Ala Glu Glu Glu Asp Phe Asp Ser
625                 630                 635                 640

Lys Glu Trp Val Ile Ile Asp Lys Glu Thr Glu Leu Lys Asp Phe Pro
                645                 650                 655

Pro Gly Ala Glu Pro Ser Thr Ser Gly Thr Thr Asp Glu Glu Pro Glu
            660                 665                 670

Glu Leu Arg Pro Leu Pro Glu Glu Gly Glu Glu Arg Arg Arg Leu Gly
        675                 680                 685

Ala Glu Pro Thr Val Arg Pro Arg Gly Arg Ser Met Gln Ala Leu Ala
    690                 695                 700

Glu Glu Asp Leu Gln His Leu Pro Pro Gln Pro Leu Pro Pro Gln Leu
705                 710                 715                 720

Ser Gln Xaa Asp Gly Arg Ser Glu Thr Ser Gln Pro Pro Thr Pro Gly
                725                 730                 735

Ser Pro Ser His Ser Pro Leu His Ser Gly Pro Arg Pro Arg Arg Arg
            740                 745                 750

Glu Ser Asp Pro Thr Gly Pro Gln Arg Gln Ala Gly Val Gln Trp Arg
        755                 760                 765

Asp Leu Gly Ser Leu Gln Pro Pro Pro Pro Arg Phe Lys Gln Phe Ser
    770                 775                 780

Cys Leu Ser Leu Pro Arg Ser Trp Asp Tyr Arg His Ala Pro Pro Pro
785                 790                 795                 800

His Pro Ala Asn Phe Val Phe Leu Val Glu Thr Gly Phe Leu His Val
                805                 810                 815

Glu Ala Gly Leu Glu Leu Leu Thr Ser Gly Asp Leu Pro Ala Ser Ala
            820                 825                 830

Ser Gln Ile Ala Gly Ile Thr Gly Val Ser His Arg Ala Gln Pro Glu
        835                 840                 845

Val Cys Glu Phe Asn Arg Lys His Thr Gly Gln Arg Glu Gln Met Val
    850                 855                 860

Cys Ala Gly Ser Glu Arg Ala Trp Ser Met Arg Asp Leu Pro Gly Arg
865                 870                 875                 880

Pro Leu Glu Pro Tyr Ser Glu Ser Tyr
                885
```

<210> SEQ ID NO 21
<211> LENGTH: 2370
<212> TYPE: DNA
<213> ORGANISM: homo sapiens

<400> SEQUENCE: 21

```
atgcagtgcc tagcggccgc ccttaaggac gaaaccaaca tgagtggggg aggggagcag     60
gccgacatcc tgccggccaa ctacgtggtc aaggatcgct ggaaggtgct gaaaaagatc    120
gggggcgggg gctttggtga gatctacgag gccatggacc tgctgaccag ggagaatgtg    180
gccctcaagg tggagtcagc ccagcagccc aagcaggtcc tcaagatgga ggtggccgtg    240
ctcaagaagt tgcaagggaa ggaccatgtg tgcaggttca ttggctgtgg caggaacgag    300
aagtttaact atgtagtgat gcagctccag ggccggaacc tggccgacct gcgccgtagc    360
cagccgcgag gcaccttcac gctgagcacc acattgcggc tgggcaagca gatcttggag    420
tccatcgagg ccatccactc tgtgggcttc ctgcaccgtg acatcaagcc ttcaaacttt    480
gccatgggca ggctgccctc cacctacagg aagtgctata tgctggactt cgggctggcc    540
cggcagtaca ccaacaccac ggggggatgtg cggcccccctc ggaatgtggc cgggtttcga    600
ggaacggttc gctatgcctc agtcaatgcc cacaagaacc gggagatggg ccgccacgac    660
gacctgtggt ccctcttcta catgctggtg gagtttgcag tgggccagct gccctggagg    720
aagatcaagg acaaggaaca ggtagggatg atcaaggaga agtatgagca ccggatgctg    780
ctgaagcaca tgccgtcaga gttccacctc ttcctggacc acattgccag cctcgactac    840
ttcaccaagc ccgactacca gttgatcatg tcagtgtttg agaacagcat gaaggagagg    900
ggcattgccg agaatgaggc ctttgactgg gagaaggcag gcaccgatgc cctcctgtcc    960
acgagcacct ctaccccgcc ccagcagaac acccggcaga cggcagccat gtttggggtg   1020
gtcaatgtga cgccagtgcc tggggacctg ctccgggaga acaccgagga tgtgctacag   1080
ggagagcacc tgagtgacca ggagaatgca cccccaattc tgcccgggag gccctctgag   1140
gggctgggcc ccagtcccca ccttgtcccc caccccgggg gtcctgaggc tgaagtctgg   1200
gaggagacag atgtcaaccg gaacaaactc cggatcaaca tcggcaaaag cccctgtgtg   1260
gaggaggaac agagccgagg catgggggtc cccagctccc cagtgcgtgc ccccccagac   1320
tcccccacaa ccccagtccg ttctctgcgc taccggaggg tgaacagccc tgagtcagaa   1380
aggctgtcca cggcggacgg gcgagtggag ctacctgaga ggaggtcacg gatggatctg   1440
cctggctcgc cctcgcgcca ggcctgctcc tctcagccag cccagatgct gtcagtggac   1500
acaggccacg ctgaccgaca ggccagtggc cgcatggayg tgtcagcctc tgtggagcag   1560
gaggccctga gcaacgcctt ccgctcggtg ccgctggctg aggaggagga tttcgacagc   1620
aaagagtggg tcatcatcga caaggagacg gagctcaagg acttccctcc aggggctgag   1680
cccagcacat cgggcaccac ggatgaggag cccgaggagc tgcggccact gcccgaggag   1740
ggcgaagagc ggcggcggct gggggcagag cccaccgtcc ggccccgggg acgcagcatg   1800
caggcgctgg cggaggagga cctgcagcat ttgccgcccc agcccctgcc accccagctg   1860
agccaggscg atggccgttc cgagacgtca cagcccccca cgcctggcag cccttcccac   1920
tcacccctgc actcgggacc ccgccctcga cggagagagt cggaccccac aggcccacag   1980
agacaggctg gagtgcaatg gcgtgatctc ggctcactgc aacctccacc tcccaggttc   2040
aagcaattct cctgcctcag cctcccgaga agctgggatt acaggcatgc accaccacca   2100
cacccggcta attttgtatt tttagtagag acggggtttc tccatgttga ggctggtctt   2160
```

```
gagctcctga cctcaggtga tctgcctgcc tcggcctccc aaattgctgg gattacaggc   2220

gtgagccatc gcgcccagcc tgaggtctgt gagtttaaca gaaaacatac aggccagaga   2280

gagcagatgg tttgtgcagg atcagagaga gcctggagca tgcgtgacct gcccgggcgg   2340

ccgctcgagc cctatagtga gtcgtattag                                    2370


<210> SEQ ID NO 22
<211> LENGTH: 789
<212> TYPE: PRT
<213> ORGANISM: homo sapiens
<220> FEATURE:
<221> NAME/KEY: VARIANT
<222> LOCATION: (1)...(789)
<223> OTHER INFORMATION: Xaa = Any Amino Acid

<400> SEQUENCE: 22

Met Gln Cys Leu Ala Ala Ala Leu Lys Asp Glu Thr Asn Met Ser Gly
 1               5                  10                  15

Gly Gly Glu Gln Ala Asp Ile Leu Pro Ala Asn Tyr Val Val Lys Asp
            20                  25                  30

Arg Trp Lys Val Leu Lys Lys Ile Gly Gly Gly Gly Phe Gly Glu Ile
        35                  40                  45

Tyr Glu Ala Met Asp Leu Leu Thr Arg Glu Asn Val Ala Leu Lys Val
    50                  55                  60

Glu Ser Ala Gln Gln Pro Lys Gln Val Leu Lys Met Glu Val Ala Val
65                  70                  75                  80

Leu Lys Lys Leu Gln Gly Lys Asp His Val Cys Arg Phe Ile Gly Cys
                85                  90                  95

Gly Arg Asn Glu Lys Phe Asn Tyr Val Val Met Gln Leu Gln Gly Arg
            100                 105                 110

Asn Leu Ala Asp Leu Arg Arg Ser Gln Pro Arg Gly Thr Phe Thr Leu
        115                 120                 125

Ser Thr Thr Leu Arg Leu Gly Lys Gln Ile Leu Glu Ser Ile Glu Ala
    130                 135                 140

Ile His Ser Val Gly Phe Leu His Arg Asp Ile Lys Pro Ser Asn Phe
145                 150                 155                 160

Ala Met Gly Arg Leu Pro Ser Thr Tyr Arg Lys Cys Tyr Met Leu Asp
                165                 170                 175

Phe Gly Leu Ala Arg Gln Tyr Thr Asn Thr Thr Gly Asp Val Arg Pro
            180                 185                 190

Pro Arg Asn Val Ala Gly Phe Arg Gly Thr Val Arg Tyr Ala Ser Val
        195                 200                 205

Asn Ala His Lys Asn Arg Glu Met Gly Arg His Asp Asp Leu Trp Ser
    210                 215                 220

Leu Phe Tyr Met Leu Val Glu Phe Ala Val Gly Gln Leu Pro Trp Arg
225                 230                 235                 240

Lys Ile Lys Asp Lys Glu Gln Val Gly Met Ile Lys Glu Lys Tyr Glu
                245                 250                 255

His Arg Met Leu Leu Lys His Met Pro Ser Glu Phe His Leu Phe Leu
            260                 265                 270

Asp His Ile Ala Ser Leu Asp Tyr Phe Thr Lys Pro Asp Tyr Gln Leu
        275                 280                 285

Ile Met Ser Val Phe Glu Asn Ser Met Lys Glu Arg Gly Ile Ala Glu
    290                 295                 300

Asn Glu Ala Phe Asp Trp Glu Lys Ala Gly Thr Asp Ala Leu Leu Ser
```

-continued

```
305                 310                 315                 320

Thr Ser Thr Ser Thr Pro Pro Gln Gln Asn Thr Arg Gln Thr Ala Ala
                325                 330                 335

Met Phe Gly Val Val Asn Val Thr Pro Val Pro Gly Asp Leu Leu Arg
            340                 345                 350

Glu Asn Thr Glu Asp Val Leu Gln Gly Glu His Leu Ser Asp Gln Glu
        355                 360                 365

Asn Ala Pro Pro Ile Leu Pro Gly Arg Pro Ser Glu Gly Leu Gly Pro
    370                 375                 380

Ser Pro His Leu Val Pro His Pro Gly Gly Pro Glu Ala Glu Val Trp
385                 390                 395                 400

Glu Glu Thr Asp Val Asn Arg Asn Lys Leu Arg Ile Asn Ile Gly Lys
                405                 410                 415

Ser Pro Cys Val Glu Glu Glu Gln Ser Arg Gly Met Gly Val Pro Ser
            420                 425                 430

Ser Pro Val Arg Ala Pro Pro Asp Ser Pro Thr Thr Pro Val Arg Ser
        435                 440                 445

Leu Arg Tyr Arg Arg Val Asn Ser Pro Glu Ser Glu Arg Leu Ser Thr
    450                 455                 460

Ala Asp Gly Arg Val Glu Leu Pro Glu Arg Arg Ser Arg Met Asp Leu
465                 470                 475                 480

Pro Gly Ser Pro Ser Arg Gln Ala Cys Ser Ser Gln Pro Ala Gln Met
                485                 490                 495

Leu Ser Val Asp Thr Gly His Ala Asp Arg Gln Ala Ser Gly Arg Met
            500                 505                 510

Asp Val Ser Ala Ser Val Glu Gln Glu Ala Leu Ser Asn Ala Phe Arg
        515                 520                 525

Ser Val Pro Leu Ala Glu Glu Glu Asp Phe Asp Ser Lys Glu Trp Val
    530                 535                 540

Ile Ile Asp Lys Glu Thr Glu Leu Lys Asp Phe Pro Pro Gly Ala Glu
545                 550                 555                 560

Pro Ser Thr Ser Gly Thr Thr Asp Glu Glu Pro Glu Glu Leu Arg Pro
                565                 570                 575

Leu Pro Glu Glu Gly Glu Glu Arg Arg Arg Leu Gly Ala Glu Pro Thr
            580                 585                 590

Val Arg Pro Arg Gly Arg Ser Met Gln Ala Leu Ala Glu Glu Asp Leu
        595                 600                 605

Gln His Leu Pro Pro Gln Pro Leu Pro Pro Gln Leu Ser Gln Xaa Asp
    610                 615                 620

Gly Arg Ser Glu Thr Ser Gln Pro Pro Thr Pro Gly Ser Pro Ser His
625                 630                 635                 640

Ser Pro Leu His Ser Gly Pro Arg Pro Arg Arg Arg Glu Ser Asp Pro
                645                 650                 655

Thr Gly Pro Gln Arg Gln Ala Gly Val Gln Trp Arg Asp Leu Gly Ser
            660                 665                 670

Leu Gln Pro Pro Pro Pro Arg Phe Lys Gln Phe Ser Cys Leu Ser Leu
        675                 680                 685

Pro Arg Ser Trp Asp Tyr Arg His Ala Pro Pro Pro His Pro Ala Asn
    690                 695                 700

Phe Val Phe Leu Val Glu Thr Gly Phe Leu His Val Glu Ala Gly Leu
705                 710                 715                 720

Glu Leu Leu Thr Ser Gly Asp Leu Pro Ala Ser Ala Ser Gln Ile Ala
                725                 730                 735
```

```
Gly Ile Thr Gly Val Ser His Arg Ala Gln Pro Glu Val Cys Glu Phe
            740                 745                 750

Asn Arg Lys His Thr Gly Gln Arg Glu Gln Met Val Cys Ala Gly Ser
        755                 760                 765

Glu Arg Ala Trp Ser Met Arg Asp Leu Pro Gly Arg Pro Leu Glu Pro
    770                 775                 780

Tyr Ser Glu Ser Tyr
785
```

<210> SEQ ID NO 23
<211> LENGTH: 2331
<212> TYPE: DNA
<213> ORGANISM: homo sapiens

<400> SEQUENCE: 23

```
atgagtgggg gaggggagca ggccgacatc ctgccggcca actacgtggt caaggatcgc     60

tggaaggtgc tgaaaaagat cgggggcggg ggctttggtg agatctacga ggccatggac    120

ctgctgacca gggagaatgt ggccctcaag gtggagtcag cccagcagcc caagcaggtc    180

ctcaagatgg aggtggccgt gctcaagaag ttgcaaggga aggaccatgt gtgcaggttc    240

attggctgtg gcaggaacga gaagtttaac tatgtagtga tgcagctcca gggccggaac    300

ctggccgacc tgcgccgtag ccagccgcga ggcaccttca cgctgagcac cacattgcgg    360

ctgggcaagc agatcttgga gtccatcgag gccatccact ctgtgggctt cctgcaccgt    420

gacatcaagc cttcaaactt tgccatgggc aggctgccct ccacctacag gaagtgctat    480

atgctggact tcgggctggc ccggcagtac accaacacca cgggggatgt gcggcccccct    540

cggaatgtgg ccgggtttcg aggaacggtt cgctatgcct cagtcaatgc ccacaagaac    600

cgggagatgg gccgccacga cgacctgtgg tccctcttct acatgctggt ggagtttgca    660

gtgggccagc tgccctggag gaagatcaag gacaaggaac aggtagggat gatcaaggag    720

aagtatgagc accggatgct gctgaagcac atgccgtcag agttccacct cttcctggac    780

cacattgcca gcctcgacta cttcaccaag cccgactacc agttgatcat gtcagtgttt    840

gagaacagca tgaaggagag ggcattgcc gagaatgagg cctttgactg ggagaaggca     900

ggcaccgatg ccctcctgtc cacgagcacc tctaccccgc cccagcagaa cacccggcag    960

acggcagcca tgtttggggt ggtcaatgtg acgccagtgc ctggggacct gctccgggag   1020

aacaccgagg atgtgctaca gggagagcac ctgagtgacc aggagaatgc acccccaatt   1080

ctgcccggga ggccctctga ggggctgggc cccagtcccc accttgtccc ccaccccggg   1140

ggtcctgagg ctgaagtctg ggaggagaca gatgtcaacc ggaacaaact ccggatcaac   1200

atcggcaaaa gcccctgtgt ggaggaggaa cagagccgag gcatgggggt ccccagctcc   1260

ccagtgcgtg cccccccaga ctcccccaca accccagtcc gttctctgcg ctaccggagg   1320

gtgaacagcc ctgagtcaga aaggctgtcc acggcggacg ggcgagtgga gctacctgag   1380

aggaggtcac ggatggatct gcctggctcg ccctcgcgcc aggcctgctc ctctcagcca   1440

gcccagatgc tgtcagtgga cacaggccac gctgaccgac aggccagtgg ccgcatggay   1500

gtgtcagcct ctgtggagca ggaggccctg agcaacgcct tccgctcggt gccgctggct   1560

gaggaggagg atttcgacag caaagagtgg gtcatcatcg acaaggagac ggagctcaag   1620

gacttccctc caggggctga gcccagcaca tcgggcacca cggatgagga gcccgaggag   1680

ctgcggccac tgcccgagga gggcgaagag cggcggcggc tgggggcaga gcccaccgtc   1740
```

-continued

```
cggccccggg gacgcagcat gcaggcgctg gcggaggagg acctgcagca tttgccgccc   1800

cagcccctgc caccccagct gagccaggsc gatggccgtt ccgagacgtc acagcccccc   1860

acgcctggca gcccttccca ctcaccccctg cactcgggac cccgccctcg acggagagag   1920

tcggacccca caggcccaca gagacaggct ggagtgcaat ggcgtgatct cggctcactg   1980

caacctccac ctcccaggtt caagcaattc tcctgcctca gcctcccgag aagctgggat   2040

tacaggcatg caccaccacc acacccggct aattttgtat ttttagtaga gacggggttt   2100

ctccatgttg aggctggtct tgagctcctg acctcaggtg atctgcctgc ctcggcctcc   2160

caaattgctg ggattacagg cgtgagccat cgcgcccagc ctgaggtctg tgagtttaac   2220

agaaaacata caggccagag agagcagatg gtttgtgcag gatcagagag agcctggagc   2280

atgcgtgacc tgcccgggcg gccgctcgag ccctatagtg agtcgtatta g           2331


<210> SEQ ID NO 24
<211> LENGTH: 776
<212> TYPE: PRT
<213> ORGANISM: homo sapiens
<220> FEATURE:
<221> NAME/KEY: VARIANT
<222> LOCATION: (1)...(776)
<223> OTHER INFORMATION: Xaa = Any Amino Acid

<400> SEQUENCE: 24

Met Ser Gly Gly Gly Glu Gln Ala Asp Ile Leu Pro Ala Asn Tyr Val
 1               5                  10                  15

Val Lys Asp Arg Trp Lys Val Leu Lys Lys Ile Gly Gly Gly Gly Phe
            20                  25                  30

Gly Glu Ile Tyr Glu Ala Met Asp Leu Leu Thr Arg Glu Asn Val Ala
        35                  40                  45

Leu Lys Val Glu Ser Ala Gln Gln Pro Lys Gln Val Leu Lys Met Glu
    50                  55                  60

Val Ala Val Leu Lys Lys Leu Gln Gly Lys Asp His Val Cys Arg Phe
65                  70                  75                  80

Ile Gly Cys Gly Arg Asn Glu Lys Phe Asn Tyr Val Val Met Gln Leu
                85                  90                  95

Gln Gly Arg Asn Leu Ala Asp Leu Arg Arg Ser Gln Pro Arg Gly Thr
            100                 105                 110

Phe Thr Leu Ser Thr Thr Leu Arg Leu Gly Lys Gln Ile Leu Glu Ser
        115                 120                 125

Ile Glu Ala Ile His Ser Val Gly Phe Leu His Arg Asp Ile Lys Pro
    130                 135                 140

Ser Asn Phe Ala Met Gly Arg Leu Pro Ser Thr Tyr Arg Lys Cys Tyr
145                 150                 155                 160

Met Leu Asp Phe Gly Leu Ala Arg Gln Tyr Thr Asn Thr Thr Gly Asp
                165                 170                 175

Val Arg Pro Pro Arg Asn Val Ala Gly Phe Arg Gly Thr Val Arg Tyr
            180                 185                 190

Ala Ser Val Asn Ala His Lys Asn Arg Glu Met Gly Arg His Asp Asp
        195                 200                 205

Leu Trp Ser Leu Phe Tyr Met Leu Val Glu Phe Ala Val Gly Gln Leu
    210                 215                 220

Pro Trp Arg Lys Ile Lys Asp Lys Glu Gln Val Gly Met Ile Lys Glu
225                 230                 235                 240

Lys Tyr Glu His Arg Met Leu Leu Lys His Met Pro Ser Glu Phe His
                245                 250                 255
```

-continued

```
Leu Phe Leu Asp His Ile Ala Ser Leu Asp Tyr Phe Thr Lys Pro Asp
            260                 265                 270

Tyr Gln Leu Ile Met Ser Val Phe Glu Asn Ser Met Lys Glu Arg Gly
        275                 280                 285

Ile Ala Glu Asn Glu Ala Phe Asp Trp Glu Lys Ala Gly Thr Asp Ala
    290                 295                 300

Leu Leu Ser Thr Ser Thr Ser Thr Pro Pro Gln Gln Asn Thr Arg Gln
305                 310                 315                 320

Thr Ala Ala Met Phe Gly Val Val Asn Val Thr Pro Val Pro Gly Asp
                325                 330                 335

Leu Leu Arg Glu Asn Thr Glu Asp Val Leu Gln Gly Glu His Leu Ser
            340                 345                 350

Asp Gln Glu Asn Ala Pro Pro Ile Leu Pro Gly Arg Pro Ser Glu Gly
        355                 360                 365

Leu Gly Pro Ser Pro His Leu Val Pro His Pro Gly Gly Pro Glu Ala
    370                 375                 380

Glu Val Trp Glu Glu Thr Asp Val Asn Arg Asn Lys Leu Arg Ile Asn
385                 390                 395                 400

Ile Gly Lys Ser Pro Cys Val Glu Glu Glu Gln Ser Arg Gly Met Gly
                405                 410                 415

Val Pro Ser Ser Pro Val Arg Ala Pro Pro Asp Ser Pro Thr Thr Pro
            420                 425                 430

Val Arg Ser Leu Arg Tyr Arg Arg Val Asn Ser Pro Glu Ser Glu Arg
        435                 440                 445

Leu Ser Thr Ala Asp Gly Arg Val Glu Leu Pro Glu Arg Arg Ser Arg
    450                 455                 460

Met Asp Leu Pro Gly Ser Pro Ser Arg Gln Ala Cys Ser Ser Gln Pro
465                 470                 475                 480

Ala Gln Met Leu Ser Val Asp Thr Gly His Ala Asp Arg Gln Ala Ser
                485                 490                 495

Gly Arg Met Asp Val Ser Ala Ser Val Glu Gln Glu Ala Leu Ser Asn
            500                 505                 510

Ala Phe Arg Ser Val Pro Leu Ala Glu Glu Glu Asp Phe Asp Ser Lys
        515                 520                 525

Glu Trp Val Ile Ile Asp Lys Glu Thr Glu Leu Lys Asp Phe Pro Pro
    530                 535                 540

Gly Ala Glu Pro Ser Thr Ser Gly Thr Thr Asp Glu Glu Pro Glu Glu
545                 550                 555                 560

Leu Arg Pro Leu Pro Glu Glu Gly Glu Glu Arg Arg Arg Leu Gly Ala
                565                 570                 575

Glu Pro Thr Val Arg Pro Arg Gly Arg Ser Met Gln Ala Leu Ala Glu
            580                 585                 590

Glu Asp Leu Gln His Leu Pro Pro Gln Pro Leu Pro Pro Gln Leu Ser
        595                 600                 605

Gln Xaa Asp Gly Arg Ser Glu Thr Ser Gln Pro Pro Thr Pro Gly Ser
    610                 615                 620

Pro Ser His Ser Pro Leu His Ser Gly Pro Arg Pro Arg Arg Arg Glu
625                 630                 635                 640

Ser Asp Pro Thr Gly Pro Gln Arg Gln Ala Gly Val Gln Trp Arg Asp
                645                 650                 655

Leu Gly Ser Leu Gln Pro Pro Pro Pro Arg Phe Lys Gln Phe Ser Cys
            660                 665                 670
```

-continued

```
Leu Ser Leu Pro Arg Ser Trp Asp Tyr Arg His Ala Pro Pro Pro His
        675                 680                 685

Pro Ala Asn Phe Val Phe Leu Val Glu Thr Gly Phe Leu His Val Glu
    690                 695                 700

Ala Gly Leu Glu Leu Leu Thr Ser Gly Asp Leu Pro Ala Ser Ala Ser
705                 710                 715                 720

Gln Ile Ala Gly Ile Thr Gly Val Ser His Arg Ala Gln Pro Glu Val
                725                 730                 735

Cys Glu Phe Asn Arg Lys His Thr Gly Gln Arg Glu Gln Met Val Cys
            740                 745                 750

Ala Gly Ser Glu Arg Ala Trp Ser Met Arg Asp Leu Pro Gly Arg Pro
        755                 760                 765

Leu Glu Pro Tyr Ser Glu Ser Tyr
    770                 775


<210> SEQ ID NO 25
<211> LENGTH: 2949
<212> TYPE: DNA
<213> ORGANISM: homo sapiens

<400> SEQUENCE: 25

atgtcagggc tggtgctgat gctggcggcg cggtgcattg tgggcagctc cccgctctgc      60

cgctgccgcc gccgtcgccc aaggaggatc ggggccgggc cgggccggga tgatccgggt     120

cggaaggccg ccgccgccgg agggagcggg tcacccaacg ccgcactgag ccgccccccgc     180

cccgccccgg ccccggggga tgcgccgccc cgagctgctg cctccgccgc cgccgcagcc     240

gcagccgcag cgggcacaga gcaggtagat ggccccctca gggcaggccc ggcggacacc     300

cctccctctg gctggcggat gcagtgccta gcggccgccc ttaaggacga aaccaacatg     360

agtgggggag gggagcaggc cgacatcctg ccggccaact acgtggtcaa ggatcgctgg     420

aaggtgctga aaaagatcgg gggcgggggc tttggtgaga tctacgaggc catggacctg     480

ctgaccaggg agaatgtggc cctcaaggtg gagtcagccc agcagcccaa gcaggtcctc     540

aagatggagg tggccgtgct caagaagttg caagggaagg accatgtgtg caggttcatt     600

ggctgtggca ggaacgagaa gtttaactat gtagtgatgc agctccaggg ccggaacctg     660

gccgacctgc gccgtagcca gccgcgaggc accttcacgc tgagcaccac attgcggctg     720

ggcaagcaga tcttggagtc catcgaggcc atccactctg tgggcttcct gcaccgtgac     780

atcaagcctt caaactttgc catgggcagg ctgccctcca cctacaggaa gtgctatatg     840

ctggacttcg ggctggcccg gcagtacacc aacaccacgg gggatgtgcg gccccctcgg     900

aatgtggccg ggtttcgagg aacggttcgc tatgcctcag tcaatgccca caagaaccgg     960

gagatgggcc gccacgacga cctgtggtcc ctcttctaca tgctggtgga gtttgcagtg    1020

ggccagctgc cctggaggaa gatcaaggac aaggaacagg tagggatgat caaggagaag    1080

tatgagcacc ggatgctgct gaagcacatg ccgtcagagt tccacctctt cctggaccac    1140

attgccagcc tcgactactt caccaagccc gactaccagt tgatcatgtc agtgtttgag    1200

aacagcatga aggagagggg cattgccgag aatgaggcct ttgactggga gaaggcaggc    1260

accgatgccc tcctgtccac gagcacctct accccgcccc agcagaacac ccggcagacg    1320

gcagccatgt ttggggtggt caatgtgacg ccagtgcctg gggacctgct ccgggagaac    1380

accgaggatg tgctacaggg agagcacctg agtgaccagg agaatgcacc cccaattctg    1440

cccgggaggc cctctgaggg gctgggcccc agtccccacc ttgtccccca ccccgggggt    1500
```

-continued

```
cctgaggctg aagtctggga ggagacagat gtcaaccgga acaaactccg gatcaacatc   1560

ggcaaagtaa ctgccgccag ggcgaagggc gtgggtggcc ttttctctca cccccgattc   1620

ccagccttgt gcccctgccc tgttcctcct aagcaccctg tccccggcca tctgcctgct   1680

tgccctgcct ctgtttcccg gtccctcccc gcactagcct cgctgtgtct tccatcatca   1740

tcatcctctg tctccttcac cctgaggaga ccatccgccc acagccgcct catcagcccc   1800

agctcatggc actcccctct cctgcagagc ccctgtgtgg aggaggaaca gagccgaggc   1860

atgggggtcc ccagctcccc agtgcgtgcc cccccagact cccccacaac cccagtccgt   1920

tctctgcgct accggagggt gaacagccct gagtcagaaa ggctgtccac ggcggacggg   1980

cgagtggagc tacctgagag gaggtcacgg atggatctgc ctggctcgcc ctcgcgccag   2040

gcctgctcct ctcagccagc ccagatgctg tcagtggaca caggccacgc tgaccgacag   2100

gccagtggcc gcatggaygt gtcagcctct gtggagcagg aggccctgag caacgccttc   2160

cgctcggtgc cgctggctga ggaggaggat ttcgacagca aagagtgggt catcatcgac   2220

aaggagacgg agctcaagga cttccctcca ggggctgagc ccagcacatc gggcaccacg   2280

gatgaggagc ccgaggagct gcggccactg cccgaggagg gcgaagagcg gcggcggctg   2340

ggggcagagc ccaccgtccg gccccgggga cgcagcatgc aggcgctggc ggaggaggac   2400

ctgcagcatt tgccgcccca gcccctgcca ccccagctga gccaggscga tggccgttcc   2460

gagacgtcac agccccccac gcctggcagc ccttcccact cacccctgca ctcgggaccc   2520

cgccctcgac ggagagagtc ggaccccaca ggcccacaga gacaggctgg agtgcaatgg   2580

cgtgatctcg gctcactgca acctccacct cccaggttca agcaattctc ctgcctcagc   2640

ctcccgagaa gctgggatta caggcatgca ccaccaccac acccggctaa ttttgtattt   2700

ttagtagaga cggggtttct ccatgttgag gctggtcttg agctcctgac ctcaggtgat   2760

ctgcctgcct cggcctccca aattgctggg attacaggcg tgagccatcg cgcccagcct   2820

gaggtctgtg agtttaacag aaaacataca ggccagagag agcagatggt ttgtgcagga   2880

tcagagagag cctggagcat gcgtgacctg cccgggcggc cgctcgagcc ctatagtgag   2940

tcgtattag                                                           2949
```

```
<210> SEQ ID NO 26
<211> LENGTH: 982
<212> TYPE: PRT
<213> ORGANISM: homo sapiens
<220> FEATURE:
<221> NAME/KEY: VARIANT
<222> LOCATION: (1)...(982)
<223> OTHER INFORMATION: Xaa = Any Amino Acid

<400> SEQUENCE: 26

Met Ser Gly Leu Val Leu Met Leu Ala Ala Arg Cys Ile Val Gly Ser
 1               5                  10                  15

Ser Pro Leu Cys Arg Cys Arg Arg Arg Arg Pro Arg Arg Ile Gly Ala
            20                  25                  30

Gly Pro Gly Arg Asp Asp Pro Gly Arg Lys Ala Ala Ala Ala Gly Gly
        35                  40                  45

Ser Gly Ser Pro Asn Ala Ala Leu Ser Arg Pro Arg Pro Ala Pro Ala
    50                  55                  60

Pro Gly Asp Ala Pro Pro Arg Ala Ala Ala Ser Ala Ala Ala Ala Ala
65                  70                  75                  80

Ala Ala Ala Ala Gly Thr Glu Gln Val Asp Gly Pro Leu Arg Ala Gly
                85                  90                  95
```

-continued

```
Pro Ala Asp Thr Pro Pro Ser Gly Trp Arg Met Gln Cys Leu Ala Ala
            100                 105                 110

Ala Leu Lys Asp Glu Thr Asn Met Ser Gly Gly Gly Glu Gln Ala Asp
        115                 120                 125

Ile Leu Pro Ala Asn Tyr Val Val Lys Asp Arg Trp Lys Val Leu Lys
    130                 135                 140

Lys Ile Gly Gly Gly Gly Phe Gly Glu Ile Tyr Glu Ala Met Asp Leu
145                 150                 155                 160

Leu Thr Arg Glu Asn Val Ala Leu Lys Val Glu Ser Ala Gln Gln Pro
                165                 170                 175

Lys Gln Val Leu Lys Met Glu Val Ala Val Leu Lys Lys Leu Gln Gly
            180                 185                 190

Lys Asp His Val Cys Arg Phe Ile Gly Cys Gly Arg Asn Glu Lys Phe
        195                 200                 205

Asn Tyr Val Val Met Gln Leu Gln Gly Arg Asn Leu Ala Asp Leu Arg
    210                 215                 220

Arg Ser Gln Pro Arg Gly Thr Phe Thr Leu Ser Thr Thr Leu Arg Leu
225                 230                 235                 240

Gly Lys Gln Ile Leu Glu Ser Ile Glu Ala Ile His Ser Val Gly Phe
                245                 250                 255

Leu His Arg Asp Ile Lys Pro Ser Asn Phe Ala Met Gly Arg Leu Pro
            260                 265                 270

Ser Thr Tyr Arg Lys Cys Tyr Met Leu Asp Phe Gly Leu Ala Arg Gln
        275                 280                 285

Tyr Thr Asn Thr Thr Gly Asp Val Arg Pro Pro Arg Asn Val Ala Gly
    290                 295                 300

Phe Arg Gly Thr Val Arg Tyr Ala Ser Val Asn Ala His Lys Asn Arg
305                 310                 315                 320

Glu Met Gly Arg His Asp Asp Leu Trp Ser Leu Phe Tyr Met Leu Val
                325                 330                 335

Glu Phe Ala Val Gly Gln Leu Pro Trp Arg Lys Ile Lys Asp Lys Glu
            340                 345                 350

Gln Val Gly Met Ile Lys Glu Lys Tyr Glu His Arg Met Leu Leu Lys
        355                 360                 365

His Met Pro Ser Glu Phe His Leu Phe Leu Asp His Ile Ala Ser Leu
    370                 375                 380

Asp Tyr Phe Thr Lys Pro Asp Tyr Gln Leu Ile Met Ser Val Phe Glu
385                 390                 395                 400

Asn Ser Met Lys Glu Arg Gly Ile Ala Glu Asn Glu Ala Phe Asp Trp
                405                 410                 415

Glu Lys Ala Gly Thr Asp Ala Leu Leu Ser Thr Ser Thr Ser Thr Pro
            420                 425                 430

Pro Gln Gln Asn Thr Arg Gln Thr Ala Ala Met Phe Gly Val Val Asn
        435                 440                 445

Val Thr Pro Val Pro Gly Asp Leu Leu Arg Glu Asn Thr Glu Asp Val
    450                 455                 460

Leu Gln Gly Glu His Leu Ser Asp Gln Glu Asn Ala Pro Pro Ile Leu
465                 470                 475                 480

Pro Gly Arg Pro Ser Glu Gly Leu Gly Pro Ser Pro His Leu Val Pro
                485                 490                 495

His Pro Gly Gly Pro Glu Ala Glu Val Trp Glu Glu Thr Asp Val Asn
            500                 505                 510
```

-continued

```
Arg Asn Lys Leu Arg Ile Asn Ile Gly Lys Val Thr Ala Ala Arg Ala
        515                 520                 525

Lys Gly Val Gly Gly Leu Phe Ser His Pro Arg Phe Pro Ala Leu Cys
    530                 535                 540

Pro Cys Pro Val Pro Pro Lys His Pro Val Pro Gly His Leu Pro Ala
545                 550                 555                 560

Cys Pro Ala Ser Val Ser Arg Ser Leu Pro Ala Leu Ala Ser Leu Cys
                565                 570                 575

Leu Pro Ser Ser Ser Ser Ser Val Ser Phe Thr Leu Arg Arg Pro Ser
            580                 585                 590

Ala His Ser Arg Leu Ile Ser Pro Ser Ser Trp His Ser Pro Leu Leu
        595                 600                 605

Gln Ser Pro Cys Val Glu Glu Glu Gln Ser Arg Gly Met Gly Val Pro
    610                 615                 620

Ser Ser Pro Val Arg Ala Pro Pro Asp Ser Pro Thr Thr Pro Val Arg
625                 630                 635                 640

Ser Leu Arg Tyr Arg Arg Val Asn Ser Pro Glu Ser Glu Arg Leu Ser
                645                 650                 655

Thr Ala Asp Gly Arg Val Glu Leu Pro Glu Arg Arg Ser Arg Met Asp
            660                 665                 670

Leu Pro Gly Ser Pro Ser Arg Gln Ala Cys Ser Ser Gln Pro Ala Gln
        675                 680                 685

Met Leu Ser Val Asp Thr Gly His Ala Asp Arg Gln Ala Ser Gly Arg
    690                 695                 700

Met Asp Val Ser Ala Ser Val Glu Gln Glu Ala Leu Ser Asn Ala Phe
705                 710                 715                 720

Arg Ser Val Pro Leu Ala Glu Glu Glu Asp Phe Asp Ser Lys Glu Trp
                725                 730                 735

Val Ile Ile Asp Lys Glu Thr Glu Leu Lys Asp Phe Pro Pro Gly Ala
            740                 745                 750

Glu Pro Ser Thr Ser Gly Thr Thr Asp Glu Glu Pro Glu Glu Leu Arg
        755                 760                 765

Pro Leu Pro Glu Glu Gly Glu Glu Arg Arg Arg Leu Gly Ala Glu Pro
    770                 775                 780

Thr Val Arg Pro Arg Gly Arg Ser Met Gln Ala Leu Ala Glu Glu Asp
785                 790                 795                 800

Leu Gln His Leu Pro Pro Gln Pro Leu Pro Pro Gln Leu Ser Gln Xaa
                805                 810                 815

Asp Gly Arg Ser Glu Thr Ser Gln Pro Pro Thr Pro Gly Ser Pro Ser
            820                 825                 830

His Ser Pro Leu His Ser Gly Pro Arg Pro Arg Arg Arg Glu Ser Asp
        835                 840                 845

Pro Thr Gly Pro Gln Arg Gln Ala Gly Val Gln Trp Arg Asp Leu Gly
    850                 855                 860

Ser Leu Gln Pro Pro Pro Pro Arg Phe Lys Gln Phe Ser Cys Leu Ser
865                 870                 875                 880

Leu Pro Arg Ser Trp Asp Tyr Arg His Ala Pro Pro Pro His Pro Ala
                885                 890                 895

Asn Phe Val Phe Leu Val Glu Thr Gly Phe Leu His Val Glu Ala Gly
            900                 905                 910

Leu Glu Leu Leu Thr Ser Gly Asp Leu Pro Ala Ser Ala Ser Gln Ile
        915                 920                 925

Ala Gly Ile Thr Gly Val Ser His Arg Ala Gln Pro Glu Val Cys Glu
```

-continued

```
930                 935                 940

Phe Asn Arg Lys His Thr Gly Gln Arg Glu Gln Met Val Cys Ala Gly
945                 950                 955                 960

Ser Glu Arg Ala Trp Ser Met Arg Asp Leu Pro Gly Arg Pro Leu Glu
                965                 970                 975

Pro Tyr Ser Glu Ser Tyr
            980


<210> SEQ ID NO 27
<211> LENGTH: 2931
<212> TYPE: DNA
<213> ORGANISM: homo sapiens

<400> SEQUENCE: 27

atgctggcgg cgcggtgcat tgtgggcagc tccccgctct gccgctgccg ccgccgtcgc     60

ccaaggagga tcggggccgg gccgggccgg gatgatccgg gtcggaaggc cgccgccgcc    120

ggagggagcg ggtcacccaa cgccgcactg agccgccccc gccccgcccc ggccccgggg    180

gatgcgccgc cccgagctgc tgcctccgcc gccgccgcag ccgcagccgc agcgggcaca    240

gagcaggtag atggccccct cagggcaggc ccggcggaca cccctccctc tggctggcgg    300

atgcagtgcc tagcggccgc ccttaaggac gaaaccaaca tgagtggggg aggggagcag    360

gccgacatcc tgccggccaa ctacgtggtc aaggatcgct ggaaggtgct gaaaaagatc    420

gggggcgggg gctttggtga gatctacgag gccatggacc tgctgaccag ggagaatgtg    480

gccctcaagg tggagtcagc ccagcagccc aagcaggtcc tcaagatgga ggtggccgtg    540

ctcaagaagt tgcaagggaa ggaccatgtg tgcaggttca ttggctgtgg caggaacgag    600

aagtttaact atgtagtgat gcagctccag ggccggaacc tggccgacct gcgccgtagc    660

cagccgcgag gcaccttcac gctgagcacc acattgcggc tgggcaagca gatcttggag    720

tccatcgagg ccatccactc tgtgggcttc ctgcaccgtg acatcaagcc ttcaaacttt    780

gccatgggca ggctgccctc cacctacagg aagtgctata tgctggactt cgggctggcc    840

cggcagtaca ccaacaccac gggggatgtg cggcccccctc ggaatgtggc cgggtttcga    900

ggaacggttc gctatgcctc agtcaatgcc cacaagaacc gggagatggg ccgccacgac    960

gacctgtggt ccctcttcta catgctggtg gagtttgcag tgggccagct gccctggagg   1020

aagatcaagg acaaggaaca ggtagggatg atcaaggaga agtatgagca ccggatgctg   1080

ctgaagcaca tgccgtcaga gttccacctc ttcctggacc acattgccag cctcgactac   1140

ttcaccaagc ccgactacca gttgatcatg tcagtgtttg agaacagcat gaaggagagg   1200

ggcattgccg agaatgaggc ctttgactgg gagaaggcag gcaccgatgc cctcctgtcc   1260

acgagcacct ctaccccgcc ccagcagaac acccggcaga cggcagccat gtttggggtg   1320

gtcaatgtga cgccagtgcc tggggacctg ctccgggaga acaccgagga tgtgctacag   1380

ggagagcacc tgagtgacca ggagaatgca cccccaattc tgcccgggag gccctctgag   1440

gggctgggcc ccagtcccca ccttgtcccc caccccgggg gtcctgaggc tgaagtctgg   1500

gaggagacag atgtcaaccg gaacaaactc cggatcaaca tcggcaaagt aactgccgcc   1560

agggcgaagg gcgtgggtgg ccttttctct cacccccgat tcccagcctt gtgcccctgc   1620

cctgttcctc ctaagcaccc tgtccccggc catctgcctg cttgccctgc ctctgtttcc   1680

cggtccctcc ccgcactagc ctcgctgtgt cttccatcat catcatcctc tgtctccttc   1740

accctgagga gaccatccgc ccacagccgc ctcatcagcc ccagctcatg gcactcccct   1800
```

-continued

```
ctcctgcaga gcccctgtgt ggaggaggaa cagagccgag gcatgggggt ccccagctcc   1860

ccagtgcgtg cccccccaga ctcccccaca accccagtcc gttctctgcg ctaccggagg   1920

gtgaacagcc ctgagtcaga aaggctgtcc acggcggacg ggcgagtgga gctacctgag   1980

aggaggtcac ggatggatct gcctggctcg ccctcgcgcc aggcctgctc ctctcagcca   2040

gcccagatgc tgtcagtgga cacaggccac gctgaccgac aggccagtgg ccgcatggay   2100

gtgtcagcct ctgtggagca ggaggccctg agcaacgcct tccgctcggt gccgctggct   2160

gaggaggagg atttcgacag caaagagtgg gtcatcatcg acaaggagac ggagctcaag   2220

gacttccctc caggggctga gcccagcaca tcgggcacca cggatgagga gcccgaggag   2280

ctgcggccac tgcccgagga gggcgaagag cggcggcggc tgggggcaga gcccaccgtc   2340

cggccccggg gacgcagcat gcaggcgctg gcggaggagg acctgcagca tttgccgccc   2400

cagcccctgc caccccagct gagccaggsc gatggccgtt ccgagacgtc acagcccccc   2460

acgcctggca gcccttccca ctcaccccctg cactcgggac cccgccctcg acggagagag   2520

tcggacccca caggcccaca gagacaggct ggagtgcaat ggcgtgatct cggctcactg   2580

caacctccac ctcccaggtt caagcaattc tcctgcctca gcctcccgag aagctgggat   2640

tacaggcatg caccaccacc acacccggct aattttgtat ttttagtaga gacggggttt   2700

ctccatgttg aggctggtct tgagctcctg acctcaggtg atctgcctgc ctcggcctcc   2760

caaattgctg ggattacagg cgtgagccat cgcgcccagc ctgaggtctg tgagtttaac   2820

agaaaacata caggccagag agagcagatg gtttgtgcag gatcagagag agcctggagc   2880

atgcgtgacc tgcccgggcg gccgctcgag ccctatagtg agtcgtatta g            2931
```

<210> SEQ ID NO 28
<211> LENGTH: 976
<212> TYPE: PRT
<213> ORGANISM: homo sapiens
<220> FEATURE:
<221> NAME/KEY: VARIANT
<222> LOCATION: (1)...(976)
<223> OTHER INFORMATION: Xaa = Any Amino Acid

<400> SEQUENCE: 28

```
Met Leu Ala Ala Arg Cys Ile Val Gly Ser Ser Pro Leu Cys Arg Cys
 1               5                  10                  15

Arg Arg Arg Arg Pro Arg Arg Ile Gly Ala Gly Pro Gly Arg Asp Asp
            20                  25                  30

Pro Gly Arg Lys Ala Ala Ala Ala Gly Gly Ser Gly Ser Pro Asn Ala
        35                  40                  45

Ala Leu Ser Arg Pro Arg Pro Ala Pro Ala Pro Gly Asp Ala Pro Pro
    50                  55                  60

Arg Ala Ala Ala Ser Ala Ala Ala Ala Ala Ala Ala Ala Ala Gly Thr
65                  70                  75                  80

Glu Gln Val Asp Gly Pro Leu Arg Ala Gly Pro Ala Asp Thr Pro Pro
                85                  90                  95

Ser Gly Trp Arg Met Gln Cys Leu Ala Ala Ala Leu Lys Asp Glu Thr
            100                 105                 110

Asn Met Ser Gly Gly Gly Glu Gln Ala Asp Ile Leu Pro Ala Asn Tyr
        115                 120                 125

Val Val Lys Asp Arg Trp Lys Val Leu Lys Lys Ile Gly Gly Gly Gly
    130                 135                 140

Phe Gly Glu Ile Tyr Glu Ala Met Asp Leu Leu Thr Arg Glu Asn Val
145                 150                 155                 160
```

-continued

```
Ala Leu Lys Val Glu Ser Ala Gln Gln Pro Lys Gln Val Leu Lys Met
                165                 170                 175

Glu Val Ala Val Leu Lys Lys Leu Gln Gly Lys Asp His Val Cys Arg
            180                 185                 190

Phe Ile Gly Cys Gly Arg Asn Glu Lys Phe Asn Tyr Val Val Met Gln
        195                 200                 205

Leu Gln Gly Arg Asn Leu Ala Asp Leu Arg Arg Ser Gln Pro Arg Gly
    210                 215                 220

Thr Phe Thr Leu Ser Thr Thr Leu Arg Leu Gly Lys Gln Ile Leu Glu
225                 230                 235                 240

Ser Ile Glu Ala Ile His Ser Val Gly Phe Leu His Arg Asp Ile Lys
                245                 250                 255

Pro Ser Asn Phe Ala Met Gly Arg Leu Pro Ser Thr Tyr Arg Lys Cys
            260                 265                 270

Tyr Met Leu Asp Phe Gly Leu Ala Arg Gln Tyr Thr Asn Thr Thr Gly
        275                 280                 285

Asp Val Arg Pro Pro Arg Asn Val Ala Gly Phe Arg Gly Thr Val Arg
    290                 295                 300

Tyr Ala Ser Val Asn Ala His Lys Asn Arg Glu Met Gly Arg His Asp
305                 310                 315                 320

Asp Leu Trp Ser Leu Phe Tyr Met Leu Val Glu Phe Ala Val Gly Gln
                325                 330                 335

Leu Pro Trp Arg Lys Ile Lys Asp Lys Glu Gln Val Gly Met Ile Lys
            340                 345                 350

Glu Lys Tyr Glu His Arg Met Leu Leu Lys His Met Pro Ser Glu Phe
        355                 360                 365

His Leu Phe Leu Asp His Ile Ala Ser Leu Asp Tyr Phe Thr Lys Pro
    370                 375                 380

Asp Tyr Gln Leu Ile Met Ser Val Phe Glu Asn Ser Met Lys Glu Arg
385                 390                 395                 400

Gly Ile Ala Glu Asn Glu Ala Phe Asp Trp Glu Lys Ala Gly Thr Asp
                405                 410                 415

Ala Leu Leu Ser Thr Ser Thr Ser Thr Pro Pro Gln Gln Asn Thr Arg
            420                 425                 430

Gln Thr Ala Ala Met Phe Gly Val Val Asn Val Thr Pro Val Pro Gly
        435                 440                 445

Asp Leu Leu Arg Glu Asn Thr Glu Asp Val Leu Gln Gly Glu His Leu
    450                 455                 460

Ser Asp Gln Glu Asn Ala Pro Pro Ile Leu Pro Gly Arg Pro Ser Glu
465                 470                 475                 480

Gly Leu Gly Pro Ser Pro His Leu Val Pro His Pro Gly Gly Pro Glu
                485                 490                 495

Ala Glu Val Trp Glu Glu Thr Asp Val Asn Arg Asn Lys Leu Arg Ile
            500                 505                 510

Asn Ile Gly Lys Val Thr Ala Ala Arg Ala Lys Gly Val Gly Gly Leu
        515                 520                 525

Phe Ser His Pro Arg Phe Pro Ala Leu Cys Pro Cys Pro Val Pro Pro
    530                 535                 540

Lys His Pro Val Pro Gly His Leu Pro Ala Cys Pro Ala Ser Val Ser
545                 550                 555                 560

Arg Ser Leu Pro Ala Leu Ala Ser Leu Cys Leu Pro Ser Ser Ser Ser
                565                 570                 575
```

-continued

```
Ser Val Ser Phe Thr Leu Arg Arg Pro Ser Ala His Ser Arg Leu Ile
            580                 585                 590

Ser Pro Ser Ser Trp His Ser Pro Leu Leu Gln Ser Pro Cys Val Glu
        595                 600                 605

Glu Glu Gln Ser Arg Gly Met Gly Val Pro Ser Ser Pro Val Arg Ala
    610                 615                 620

Pro Pro Asp Ser Pro Thr Thr Pro Val Arg Ser Leu Arg Tyr Arg Arg
625                 630                 635                 640

Val Asn Ser Pro Glu Ser Glu Arg Leu Ser Thr Ala Asp Gly Arg Val
                645                 650                 655

Glu Leu Pro Glu Arg Arg Ser Arg Met Asp Leu Pro Gly Ser Pro Ser
            660                 665                 670

Arg Gln Ala Cys Ser Ser Gln Pro Ala Gln Met Leu Ser Val Asp Thr
        675                 680                 685

Gly His Ala Asp Arg Gln Ala Ser Gly Arg Met Asp Val Ser Ala Ser
    690                 695                 700

Val Glu Gln Glu Ala Leu Ser Asn Ala Phe Arg Ser Val Pro Leu Ala
705                 710                 715                 720

Glu Glu Glu Asp Phe Asp Ser Lys Glu Trp Val Ile Ile Asp Lys Glu
                725                 730                 735

Thr Glu Leu Lys Asp Phe Pro Pro Gly Ala Glu Pro Ser Thr Ser Gly
            740                 745                 750

Thr Thr Asp Glu Glu Pro Glu Glu Leu Arg Pro Leu Pro Glu Glu Gly
        755                 760                 765

Glu Glu Arg Arg Arg Leu Gly Ala Glu Pro Thr Val Arg Pro Arg Gly
    770                 775                 780

Arg Ser Met Gln Ala Leu Ala Glu Glu Asp Leu Gln His Leu Pro Pro
785                 790                 795                 800

Gln Pro Leu Pro Pro Gln Leu Ser Gln Xaa Asp Gly Arg Ser Glu Thr
                805                 810                 815

Ser Gln Pro Pro Thr Pro Gly Ser Pro Ser His Ser Pro Leu His Ser
            820                 825                 830

Gly Pro Arg Pro Arg Arg Arg Glu Ser Asp Pro Thr Gly Pro Gln Arg
        835                 840                 845

Gln Ala Gly Val Gln Trp Arg Asp Leu Gly Ser Leu Gln Pro Pro Pro
    850                 855                 860

Pro Arg Phe Lys Gln Phe Ser Cys Leu Ser Leu Pro Arg Ser Trp Asp
865                 870                 875                 880

Tyr Arg His Ala Pro Pro Pro His Pro Ala Asn Phe Val Phe Leu Val
                885                 890                 895

Glu Thr Gly Phe Leu His Val Glu Ala Gly Leu Glu Leu Leu Thr Ser
            900                 905                 910

Gly Asp Leu Pro Ala Ser Ala Ser Gln Ile Ala Gly Ile Thr Gly Val
        915                 920                 925

Ser His Arg Ala Gln Pro Glu Val Cys Glu Phe Asn Arg Lys His Thr
    930                 935                 940

Gly Gln Arg Glu Gln Met Val Cys Ala Gly Ser Glu Arg Ala Trp Ser
945                 950                 955                 960

Met Arg Asp Leu Pro Gly Arg Pro Leu Glu Pro Tyr Ser Glu Ser Tyr
                965                 970                 975
```

<210> SEQ ID NO 29
<211> LENGTH: 2631
<212> TYPE: DNA

-continued

<213> ORGANISM: homo sapiens

<400> SEQUENCE: 29

```
atgcagtgcc tagcggccgc ccttaaggac gaaaccaaca tgagtggggg aggggagcag     60
gccgacatcc tgccggccaa ctacgtggtc aaggatcgct ggaaggtgct gaaaaagatc    120
gggggcgggg gctttggtga gatctacgag gccatggacc tgctgaccag ggagaatgtg    180
gccctcaagg tggagtcagc ccagcagccc aagcaggtcc tcaagatgga ggtggccgtg    240
ctcaagaagt tgcaagggaa ggaccatgtg tgcaggttca ttggctgtgg caggaacgag    300
aagtttaact atgtagtgat gcagctccag ggccggaacc tggccgacct gcgccgtagc    360
cagccgcgag gcaccttcac gctgagcacc acattgcggc tgggcaagca gatcttggag    420
tccatcgagg ccatccactc tgtgggcttc ctgcaccgtg acatcaagcc ttcaaacttt    480
gccatgggca ggctgccctc cacctacagg aagtgctata tgctggactt cgggctggcc    540
cggcagtaca ccaacaccac gggggatgtg cggcccccctc ggaatgtggc cgggtttcga    600
ggaacggttc gctatgcctc agtcaatgcc cacaagaacc gggagatggg ccgccacgac    660
gacctgtggt ccctcttcta catgctggtg gagtttgcag tgggccagct gccctggagg    720
aagatcaagg acaaggaaca ggtagggatg atcaaggaga agtatgagca ccggatgctg    780
ctgaagcaca tgccgtcaga gttccacctc ttcctggacc acattgccag cctcgactac    840
ttcaccaagc ccgactacca gttgatcatg tcagtgtttg agaacagcat gaaggagagg    900
ggcattgccg agaatgaggc ctttgactgg gagaaggcag gcaccgatgc cctcctgtcc    960
acgagcacct ctaccccgcc ccagcagaac acccggcaga cggcagccat gtttggggtg   1020
gtcaatgtga cgccagtgcc tggggacctg ctccgggaga acaccgagga tgtgctacag   1080
ggagagcacc tgagtgacca ggagaatgca cccccaattc tgcccgggag gccctctgag   1140
gggctgggcc ccagtcccca ccttgtcccc caccccgggg gtcctgaggc tgaagtctgg   1200
gaggagacag atgtcaaccg gaacaaactc cggatcaaca tcggcaaagt aactgccgcc   1260
agggcgaagg gcgtgggtgg ccttttctct cacccccgat tcccagcctt gtgcccctgc   1320
cctgttcctc ctaagcaccc tgtccccggc catctgcctg cttgccctgc ctctgtttcc   1380
cggtccctcc ccgcactagc ctcgctgtgt cttccatcat catcatcctc tgtctccttc   1440
accctgagga gaccatccgc ccacagccgc ctcatcagcc ccagctcatg gcactcccct   1500
ctcctgcaga gcccctgtgt ggaggaggaa cagagccgag gcatggggt ccccagctcc   1560
ccagtgcgtg cccccccaga ctcccccaca accccagtcc gttctctgcg ctaccggagg   1620
gtgaacagcc ctgagtcaga aaggctgtcc acggcggacg ggcgagtgga gctacctgag   1680
aggaggtcac ggatggatct gcctggctcg ccctcgcgcc aggcctgctc ctctcagcca   1740
gcccagatgc tgtcagtgga cacaggccac gctgaccgac aggccagtgg ccgcatggay   1800
gtgtcagcct ctgtggagca ggaggccctg agcaacgcct tccgctcggt gccgctggct   1860
gaggaggagg atttcgacag caaagagtgg gtcatcatcg acaaggagac ggagctcaag   1920
gacttccctc caggggctga gcccagcaca tcgggcacca cggatgagga gcccgaggag   1980
ctgcggccac tgcccgagga gggcgaagag cggcggcggc tgggggcaga gcccaccgtc   2040
cggccccggg gacgcagcat gcaggcgctg gcggaggagg acctgcagca tttgccgccc   2100
cagcccctgc caccccagct gagccaggsc gatggccgtt ccgagacgtc acagcccccc   2160
acgcctggca gcccttccca ctcacccctg cactcgggac cccgccctcg acggagagag   2220
tcggacccca caggcccaca gagacaggct ggagtgcaat ggcgtgatct cggctcactg   2280
```

```
caacctccac ctcccaggtt caagcaattc tcctgcctca gcctcccgag aagctgggat   2340

tacaggcatg caccaccacc acacccggct aattttgtat ttttagtaga gacggggttt   2400

ctccatgttg aggctggtct tgagctcctg acctcaggtg atctgcctgc ctcggcctcc   2460

caaattgctg ggattacagg cgtgagccat cgcgcccagc ctgaggtctg tgagtttaac   2520

agaaaacata caggccagag agagcagatg gtttgtgcag gatcagagag agcctggagc   2580

atgcgtgacc tgcccgggcg gccgctcgag ccctatagtg agtcgtatta g            2631


<210> SEQ ID NO 30
<211> LENGTH: 876
<212> TYPE: PRT
<213> ORGANISM: homo sapiens
<220> FEATURE:
<221> NAME/KEY: VARIANT
<222> LOCATION: (1)...(876)
<223> OTHER INFORMATION: Xaa = Any Amino Acid

<400> SEQUENCE: 30

Met Gln Cys Leu Ala Ala Ala Leu Lys Asp Glu Thr Asn Met Ser Gly
 1               5                  10                  15

Gly Gly Glu Gln Ala Asp Ile Leu Pro Ala Asn Tyr Val Val Lys Asp
            20                  25                  30

Arg Trp Lys Val Leu Lys Lys Ile Gly Gly Gly Gly Phe Gly Glu Ile
        35                  40                  45

Tyr Glu Ala Met Asp Leu Leu Thr Arg Glu Asn Val Ala Leu Lys Val
    50                  55                  60

Glu Ser Ala Gln Gln Pro Lys Gln Val Leu Lys Met Glu Val Ala Val
65                  70                  75                  80

Leu Lys Lys Leu Gln Gly Lys Asp His Val Cys Arg Phe Ile Gly Cys
                85                  90                  95

Gly Arg Asn Glu Lys Phe Asn Tyr Val Val Met Gln Leu Gln Gly Arg
            100                 105                 110

Asn Leu Ala Asp Leu Arg Arg Ser Gln Pro Arg Gly Thr Phe Thr Leu
        115                 120                 125

Ser Thr Thr Leu Arg Leu Gly Lys Gln Ile Leu Glu Ser Ile Glu Ala
    130                 135                 140

Ile His Ser Val Gly Phe Leu His Arg Asp Ile Lys Pro Ser Asn Phe
145                 150                 155                 160

Ala Met Gly Arg Leu Pro Ser Thr Tyr Arg Lys Cys Tyr Met Leu Asp
                165                 170                 175

Phe Gly Leu Ala Arg Gln Tyr Thr Asn Thr Thr Gly Asp Val Arg Pro
            180                 185                 190

Pro Arg Asn Val Ala Gly Phe Arg Gly Thr Val Arg Tyr Ala Ser Val
        195                 200                 205

Asn Ala His Lys Asn Arg Glu Met Gly Arg His Asp Asp Leu Trp Ser
    210                 215                 220

Leu Phe Tyr Met Leu Val Glu Phe Ala Val Gly Gln Leu Pro Trp Arg
225                 230                 235                 240

Lys Ile Lys Asp Lys Glu Gln Val Gly Met Ile Lys Glu Lys Tyr Glu
                245                 250                 255

His Arg Met Leu Leu Lys His Met Pro Ser Glu Phe His Leu Phe Leu
            260                 265                 270

Asp His Ile Ala Ser Leu Asp Tyr Phe Thr Lys Pro Asp Tyr Gln Leu
        275                 280                 285
```

-continued

```
Ile Met Ser Val Phe Glu Asn Ser Met Lys Glu Arg Gly Ile Ala Glu
    290                 295                 300

Asn Glu Ala Phe Asp Trp Glu Lys Ala Gly Thr Asp Ala Leu Leu Ser
305                 310                 315                 320

Thr Ser Thr Ser Thr Pro Pro Gln Gln Asn Thr Arg Gln Thr Ala Ala
                325                 330                 335

Met Phe Gly Val Val Asn Val Thr Pro Val Pro Gly Asp Leu Leu Arg
            340                 345                 350

Glu Asn Thr Glu Asp Val Leu Gln Gly Glu His Leu Ser Asp Gln Glu
        355                 360                 365

Asn Ala Pro Pro Ile Leu Pro Gly Arg Pro Ser Glu Gly Leu Gly Pro
    370                 375                 380

Ser Pro His Leu Val Pro His Pro Gly Gly Pro Glu Ala Glu Val Trp
385                 390                 395                 400

Glu Glu Thr Asp Val Asn Arg Asn Lys Leu Arg Ile Asn Ile Gly Lys
                405                 410                 415

Val Thr Ala Ala Arg Ala Lys Gly Val Gly Gly Leu Phe Ser His Pro
            420                 425                 430

Arg Phe Pro Ala Leu Cys Pro Cys Pro Val Pro Pro Lys His Pro Val
        435                 440                 445

Pro Gly His Leu Pro Ala Cys Pro Ala Ser Val Ser Arg Ser Leu Pro
    450                 455                 460

Ala Leu Ala Ser Leu Cys Leu Pro Ser Ser Ser Ser Ser Val Ser Phe
465                 470                 475                 480

Thr Leu Arg Arg Pro Ser Ala His Ser Arg Leu Ile Ser Pro Ser Ser
                485                 490                 495

Trp His Ser Pro Leu Leu Gln Ser Pro Cys Val Glu Glu Glu Gln Ser
            500                 505                 510

Arg Gly Met Gly Val Pro Ser Ser Pro Val Arg Ala Pro Pro Asp Ser
        515                 520                 525

Pro Thr Thr Pro Val Arg Ser Leu Arg Tyr Arg Arg Val Asn Ser Pro
    530                 535                 540

Glu Ser Glu Arg Leu Ser Thr Ala Asp Gly Arg Val Glu Leu Pro Glu
545                 550                 555                 560

Arg Arg Ser Arg Met Asp Leu Pro Gly Ser Pro Ser Arg Gln Ala Cys
                565                 570                 575

Ser Ser Gln Pro Ala Gln Met Leu Ser Val Asp Thr Gly His Ala Asp
            580                 585                 590

Arg Gln Ala Ser Gly Arg Met Asp Val Ser Ala Ser Val Glu Gln Glu
        595                 600                 605

Ala Leu Ser Asn Ala Phe Arg Ser Val Pro Leu Ala Glu Glu Glu Asp
    610                 615                 620

Phe Asp Ser Lys Glu Trp Val Ile Ile Asp Lys Glu Thr Glu Leu Lys
625                 630                 635                 640

Asp Phe Pro Pro Gly Ala Glu Pro Ser Thr Ser Gly Thr Thr Asp Glu
                645                 650                 655

Glu Pro Glu Glu Leu Arg Pro Leu Pro Glu Glu Gly Glu Glu Arg Arg
            660                 665                 670

Arg Leu Gly Ala Glu Pro Thr Val Arg Pro Arg Gly Arg Ser Met Gln
        675                 680                 685

Ala Leu Ala Glu Glu Asp Leu Gln His Leu Pro Pro Gln Pro Leu Pro
    690                 695                 700

Pro Gln Leu Ser Gln Xaa Asp Gly Arg Ser Glu Thr Ser Gln Pro Pro
```

-continued

```
705                 710                 715                 720

Thr Pro Gly Ser Pro Ser His Ser Pro Leu His Ser Gly Pro Arg Pro
                725                 730                 735

Arg Arg Arg Glu Ser Asp Pro Thr Gly Pro Gln Arg Gln Ala Gly Val
            740                 745                 750

Gln Trp Arg Asp Leu Gly Ser Leu Gln Pro Pro Pro Pro Arg Phe Lys
        755                 760                 765

Gln Phe Ser Cys Leu Ser Leu Pro Arg Ser Trp Asp Tyr Arg His Ala
    770                 775                 780

Pro Pro Pro His Pro Ala Asn Phe Val Phe Leu Val Glu Thr Gly Phe
785                 790                 795                 800

Leu His Val Glu Ala Gly Leu Glu Leu Leu Thr Ser Gly Asp Leu Pro
                805                 810                 815

Ala Ser Ala Ser Gln Ile Ala Gly Ile Thr Gly Val Ser His Arg Ala
            820                 825                 830

Gln Pro Glu Val Cys Glu Phe Asn Arg Lys His Thr Gly Gln Arg Glu
        835                 840                 845

Gln Met Val Cys Ala Gly Ser Glu Arg Ala Trp Ser Met Arg Asp Leu
    850                 855                 860

Pro Gly Arg Pro Leu Glu Pro Tyr Ser Glu Ser Tyr
865                 870                 875


<210> SEQ ID NO 31
<211> LENGTH: 2592
<212> TYPE: DNA
<213> ORGANISM: homo sapiens

<400> SEQUENCE: 31

atgagtgggg gaggggagca ggccgacatc ctgccggcca actacgtggt caaggatcgc      60

tggaaggtgc tgaaaaagat cgggggcggg ggctttggtg agatctacga ggccatggac     120

ctgctgacca gggagaatgt ggccctcaag gtggagtcag cccagcagcc caagcaggtc     180

ctcaagatgg aggtggccgt gctcaagaag ttgcaaggga aggaccatgt gtgcaggttc     240

attggctgtg gcaggaacga gaagtttaac tatgtagtga tgcagctcca gggccggaac     300

ctggccgacc tgcgccgtag ccagccgcga ggcaccttca cgctgagcac cacattgcgg     360

ctgggcaagc agatcttgga gtccatcgag gccatccact ctgtgggctt cctgcaccgt     420

gacatcaagc cttcaaactt tgccatgggc aggctgccct ccacctacag gaagtgctat     480

atgctggact tcgggctggc ccggcagtac accaacacca cgggggatgt gcggcccccct     540

cggaatgtgg ccgggtttcg aggaacggtt cgctatgcct cagtcaatgc ccacaagaac     600

cgggagatgg gccgccacga cgacctgtgg tccctcttct acatgctggt ggagtttgca     660

gtgggccagc tgccctggag gaagatcaag gacaaggaac aggtagggat gatcaaggag     720

aagtatgagc accggatgct gctgaagcac atgccgtcag agttccacct cttcctggac     780

cacattgcca gcctcgacta cttcaccaag cccgactacc agttgatcat gtcagtgttt     840

gagaacagca tgaaggagag ggcattgcc gagaatgagg cctttgactg ggagaaggca      900

ggcaccgatg ccctcctgtc cacgagcacc tctaccccgc cccagcagaa cacccggcag     960

acggcagcca tgtttggggt ggtcaatgtg acgccagtgc ctggggacct gctccgggag    1020

aacaccgagg atgtgctaca gggagagcac ctgagtgacc aggagaatgc acccccaatt    1080

ctgcccggga ggccctctga ggggctgggc cccagtcccc accttgtccc ccaccccggg    1140

ggtcctgagg ctgaagtctg ggaggagaca gatgtcaacc ggaacaaact ccggatcaac    1200
```

```
atcggcaaag taactgccgc cagggcgaag ggcgtgggtg gccttttctc tcacccccga   1260
ttcccagcct tgtgcccctg ccctgttcct cctaagcacc ctgtccccgg ccatctgcct   1320
gcttgccctg cctctgtttc ccggtccctc cccgcactag cctcgctgtg tcttccatca   1380
tcatcatcct ctgtctcctt caccctgagg agaccatccg cccacagccg cctcatcagc   1440
cccagctcat ggcactcccc tctcctgcag agcccctgtg tggaggagga acagagccga   1500
ggcatggggg tccccagctc cccagtgcgt gcccccccag actcccccac aaccccagtc   1560
cgttctctgc gctaccggag ggtgaacagc cctgagtcag aaaggctgtc cacggcggac   1620
gggcgagtgg agctacctga gaggaggtca cggatggatc tgcctggctc gccctcgcgc   1680
caggcctgct cctctcagcc agcccagatg ctgtcagtgg acacaggcca cgctgaccga   1740
caggccagtg gccgcatgga ygtgtcagcc tctgtggagc aggaggccct gagcaacgcc   1800
ttccgctcgg tgccgctggc tgaggaggag gatttcgaca gcaaagagtg ggtcatcatc   1860
gacaaggaga cggagctcaa ggacttccct ccaggggctg agcccagcac atcgggcacc   1920
acggatgagg agcccgagga gctgcggcca ctgcccgagg agggcgaaga gcggcggcgg   1980
ctgggggcag agcccaccgt ccggccccgg ggacgcagca tgcaggcgct ggcggaggag   2040
gacctgcagc atttgccgcc ccagcccctg ccaccccagc tgagccaggs cgatggccgt   2100
tccgagacgt cacagccccc cacgcctggc agcccttccc actcacccct gcactcggga   2160
ccccgccctc gacggagaga gtcggacccc acaggcccac agagacaggc tggagtgcaa   2220
tggcgtgatc tcggctcact gcaacctcca cctcccaggt tcaagcaatt ctcctgcctc   2280
agcctcccga gaagctggga ttacaggcat gcaccaccac cacacccggc taattttgta   2340
tttttagtag agacggggtt tctccatgtt gaggctggtc ttgagctcct gacctcaggt   2400
gatctgcctg cctcggcctc ccaaattgct gggattacag gcgtgagcca tcgcgcccag   2460
cctgaggtct gtgagtttaa cagaaaacat acaggccaga gagagcagat ggtttgtgca   2520
ggatcagaga gagcctggag catgcgtgac ctgcccgggc ggccgctcga gccctatagt   2580
gagtcgtatt ag                                                       2592
```

```
<210> SEQ ID NO 32
<211> LENGTH: 863
<212> TYPE: PRT
<213> ORGANISM: homo sapiens
<220> FEATURE:
<221> NAME/KEY: VARIANT
<222> LOCATION: (1)...(863)
<223> OTHER INFORMATION: Xaa = Any Amino Acid

<400> SEQUENCE: 32

Met Ser Gly Gly Gly Glu Gln Ala Asp Ile Leu Pro Ala Asn Tyr Val
 1               5                  10                  15

Val Lys Asp Arg Trp Lys Val Leu Lys Lys Ile Gly Gly Gly Gly Phe
            20                  25                  30

Gly Glu Ile Tyr Glu Ala Met Asp Leu Leu Thr Arg Glu Asn Val Ala
        35                  40                  45

Leu Lys Val Glu Ser Ala Gln Gln Pro Lys Gln Val Leu Lys Met Glu
    50                  55                  60

Val Ala Val Leu Lys Lys Leu Gln Gly Lys Asp His Val Cys Arg Phe
65                  70                  75                  80

Ile Gly Cys Gly Arg Asn Glu Lys Phe Asn Tyr Val Val Met Gln Leu
                85                  90                  95
```

-continued

```
Gln Gly Arg Asn Leu Ala Asp Leu Arg Arg Ser Gln Pro Arg Gly Thr
            100                 105                 110

Phe Thr Leu Ser Thr Thr Leu Arg Leu Gly Lys Gln Ile Leu Glu Ser
        115                 120                 125

Ile Glu Ala Ile His Ser Val Gly Phe Leu His Arg Asp Ile Lys Pro
    130                 135                 140

Ser Asn Phe Ala Met Gly Arg Leu Pro Ser Thr Tyr Arg Lys Cys Tyr
145                 150                 155                 160

Met Leu Asp Phe Gly Leu Ala Arg Gln Tyr Thr Asn Thr Thr Gly Asp
                165                 170                 175

Val Arg Pro Pro Arg Asn Val Ala Gly Phe Arg Gly Thr Val Arg Tyr
            180                 185                 190

Ala Ser Val Asn Ala His Lys Asn Arg Glu Met Gly Arg His Asp Asp
        195                 200                 205

Leu Trp Ser Leu Phe Tyr Met Leu Val Glu Phe Ala Val Gly Gln Leu
    210                 215                 220

Pro Trp Arg Lys Ile Lys Asp Lys Glu Gln Val Gly Met Ile Lys Glu
225                 230                 235                 240

Lys Tyr Glu His Arg Met Leu Leu Lys His Met Pro Ser Glu Phe His
                245                 250                 255

Leu Phe Leu Asp His Ile Ala Ser Leu Asp Tyr Phe Thr Lys Pro Asp
            260                 265                 270

Tyr Gln Leu Ile Met Ser Val Phe Glu Asn Ser Met Lys Glu Arg Gly
        275                 280                 285

Ile Ala Glu Asn Glu Ala Phe Asp Trp Glu Lys Ala Gly Thr Asp Ala
    290                 295                 300

Leu Leu Ser Thr Ser Thr Ser Thr Pro Pro Gln Gln Asn Thr Arg Gln
305                 310                 315                 320

Thr Ala Ala Met Phe Gly Val Val Asn Val Thr Pro Val Pro Gly Asp
                325                 330                 335

Leu Leu Arg Glu Asn Thr Glu Asp Val Leu Gln Gly Glu His Leu Ser
            340                 345                 350

Asp Gln Glu Asn Ala Pro Pro Ile Leu Pro Gly Arg Pro Ser Glu Gly
        355                 360                 365

Leu Gly Pro Ser Pro His Leu Val Pro His Pro Gly Gly Pro Glu Ala
    370                 375                 380

Glu Val Trp Glu Glu Thr Asp Val Asn Arg Asn Lys Leu Arg Ile Asn
385                 390                 395                 400

Ile Gly Lys Val Thr Ala Ala Arg Ala Lys Gly Val Gly Gly Leu Phe
                405                 410                 415

Ser His Pro Arg Phe Pro Ala Leu Cys Pro Cys Pro Val Pro Pro Lys
            420                 425                 430

His Pro Val Pro Gly His Leu Pro Ala Cys Pro Ala Ser Val Ser Arg
        435                 440                 445

Ser Leu Pro Ala Leu Ala Ser Leu Cys Leu Pro Ser Ser Ser Ser Ser
    450                 455                 460

Val Ser Phe Thr Leu Arg Arg Pro Ser Ala His Ser Arg Leu Ile Ser
465                 470                 475                 480

Pro Ser Ser Trp His Ser Pro Leu Leu Gln Ser Pro Cys Val Glu Glu
                485                 490                 495

Glu Gln Ser Arg Gly Met Gly Val Pro Ser Ser Pro Val Arg Ala Pro
            500                 505                 510

Pro Asp Ser Pro Thr Thr Pro Val Arg Ser Leu Arg Tyr Arg Arg Val
```

-continued

```
        515                 520                 525

Asn Ser Pro Glu Ser Glu Arg Leu Ser Thr Ala Asp Gly Arg Val Glu
    530                 535                 540

Leu Pro Glu Arg Arg Ser Arg Met Asp Leu Pro Gly Ser Pro Ser Arg
545                 550                 555                 560

Gln Ala Cys Ser Ser Gln Pro Ala Gln Met Leu Ser Val Asp Thr Gly
                565                 570                 575

His Ala Asp Arg Gln Ala Ser Gly Arg Met Asp Val Ser Ala Ser Val
            580                 585                 590

Glu Gln Glu Ala Leu Ser Asn Ala Phe Arg Ser Val Pro Leu Ala Glu
        595                 600                 605

Glu Glu Asp Phe Asp Ser Lys Glu Trp Val Ile Ile Asp Lys Glu Thr
    610                 615                 620

Glu Leu Lys Asp Phe Pro Pro Gly Ala Glu Pro Ser Thr Ser Gly Thr
625                 630                 635                 640

Thr Asp Glu Glu Pro Glu Glu Leu Arg Pro Leu Pro Glu Glu Gly Glu
                645                 650                 655

Glu Arg Arg Arg Leu Gly Ala Glu Pro Thr Val Arg Pro Arg Gly Arg
            660                 665                 670

Ser Met Gln Ala Leu Ala Glu Glu Asp Leu Gln His Leu Pro Pro Gln
        675                 680                 685

Pro Leu Pro Pro Gln Leu Ser Gln Xaa Asp Gly Arg Ser Glu Thr Ser
    690                 695                 700

Gln Pro Pro Thr Pro Gly Ser Pro Ser His Ser Pro Leu His Ser Gly
705                 710                 715                 720

Pro Arg Pro Arg Arg Arg Glu Ser Asp Pro Thr Gly Pro Gln Arg Gln
                725                 730                 735

Ala Gly Val Gln Trp Arg Asp Leu Gly Ser Leu Gln Pro Pro Pro Pro
            740                 745                 750

Arg Phe Lys Gln Phe Ser Cys Leu Ser Leu Pro Arg Ser Trp Asp Tyr
        755                 760                 765

Arg His Ala Pro Pro Pro His Pro Ala Asn Phe Val Phe Leu Val Glu
    770                 775                 780

Thr Gly Phe Leu His Val Glu Ala Gly Leu Glu Leu Leu Thr Ser Gly
785                 790                 795                 800

Asp Leu Pro Ala Ser Ala Ser Gln Ile Ala Gly Ile Thr Gly Val Ser
                805                 810                 815

His Arg Ala Gln Pro Glu Val Cys Glu Phe Asn Arg Lys His Thr Gly
            820                 825                 830

Gln Arg Glu Gln Met Val Cys Ala Gly Ser Glu Arg Ala Trp Ser Met
        835                 840                 845

Arg Asp Leu Pro Gly Arg Pro Leu Glu Pro Tyr Ser Glu Ser Tyr
    850                 855                 860

<210> SEQ ID NO 33
<211> LENGTH: 2874
<212> TYPE: DNA
<213> ORGANISM: homo sapiens

<400> SEQUENCE: 33

atgtcagggc tggtgctgat gctggcggcg cggtgcattg tgggcagctc cccgctctgc      60

cgctgccgcc gccgtcgccc aaggaggatc ggggccgggc cgggccggga tgatccgggt     120

cggaaggccg ccgccgccgg agggagcggg tcacccaacg ccgcactgag ccgccccgc      180
```

-continued

```
cccgccccgg ccccggggga tgcgccgccc cgagctgctg cctccgccgc cgccgcagcc    240
gcagccgcag cgggcacaga gcaggtagat ggccccctca gggcaggccc ggcggacacc    300
cctccctctg gctggcggat gcagtgccta gcggccgccc ttaaggacga aaccaacatg    360
agtgggggag gggagcaggc cgacatcctg ccggccaact acgtggtcaa ggatcgctgg    420
aaggtgctga aaaagatcgg gggcgggggc tttggtgaga tctacgaggc catggacctg    480
ctgaccaggg agaatgtggc cctcaaggtg gagtcagccc agcagcccaa gcaggtcctc    540
aagatggagg tggccgtgct caagaagttg caagggaagg accatgtgtg caggttcatt    600
ggctgtggca ggaacgagaa gtttaactat gtagtgatgc agctccaggg ccggaacctg    660
gccgacctgc gccgtagcca gccgcgaggc accttcacgc tgagcaccac attgcggctg    720
ggcaagcaga tcttggagtc catcgaggcc atccactctg tgggcttcct gcaccgtgac    780
atcaagcctt caaactttgc catgggcagg ctgccctcca cctacaggaa gtgctatatg    840
ctggacttcg ggctggcccg gcagtacacc aacaccacgg gggatgtgcg gccccctcgg    900
aatgtggccg ggtttcgagg aacggttcgc tatgcctcag tcaatgccca caagaaccgg    960
gagatgggcc gccacgacga cctgtggtcc ctcttctaca tgctggtgga gtttgcagtg   1020
ggccagctgc cctggaggaa gatcaaggac aaggaacagg tagggatgat caaggagaag   1080
tatgagcacc ggatgctgct gaagcacatg ccgtcagagt tccacctctt cctggaccac   1140
attgccagcc tcgactactt caccaagccc gactaccagt tgatcatgtc agtgtttgag   1200
aacagcatga aggagagggg cattgccgag aatgaggcct ttgactggga gaaggcaggc   1260
accgatgccc tcctgtccac gagcacctct accccgcccc agcagaacac ccggcagacg   1320
gcagccatgt ttggggtggt caatgtgacg ccagtgcctg gggacctgct ccgggagaac   1380
accgaggatg tgctacaggg agagcacctg agtgaccagg agaatgcacc cccaattctg   1440
cccgggaggc cctctgaggg gctgggcccc agtccccacc ttgtccccca ccccgggggt   1500
cctgaggctg aagtctggga ggagacagat gtcaaccgga acaaactccg gatcaacatc   1560
ggcaaagtaa ctgccgccag ggcgaagggc gtgggtggcc ttttctctca cccccgattc   1620
ccagccttgt gcccctgccc tgttcctcct aagcaccctg tccccggcca tctgcctgct   1680
tgccctgcct ctgtttcccg gtccctcccc gcactagcct cgctgtgtct tccatcatca   1740
tcatcctctg tctccttcac cctgaggaga ccatccgccc acagccgcct catcagcccc   1800
agctcatggc actcccctct cctgcagagc ccctgtgtgg aggaggaaca gagccgaggc   1860
atgggggtcc ccagctcccc agtgcgtgcc cccccagact cccccacaac cccagtccgt   1920
tctctgcgct accggagggt gaacagccct gagtcagaaa ggctgtccac ggcggacggg   1980
cgagtggagc tacctgagag gaggtcacgg atggatctgc ctggctcgcc ctcgcgccag   2040
gcctgctcct ctcagccagc ccagatgctg tcagtggaca caggccacgc tgaccgacag   2100
gccagtggcc gcatggaygt gtcagcctct gtggagcagg aggccctgag caacgccttc   2160
cgctcggtgc cgctggctga ggaggaggat ttcgacagca aagagtgggt catcatcgac   2220
aaggagacgg agctcaagga cttccctcca ggggctgagc ccagcacatc gggcaccacg   2280
gatgaggagc ccgaggagct gcggccactg cccgaggagg gcgaagagcg gcggcggctg   2340
ggggcagagc ccaccgtccg gccccgggga cgcagcatgc aggcgctggc ggaggaggac   2400
ctgcagcatt tgccgcccca gcccctgcca ccccagctga gccaggscga tggccgttcc   2460
gagacgtcac agccccccac gcctggcagc ccttcccact cacccctgca ctcgggaccc   2520
cgccctcgac ggagagagtc ggaccccaca ggcccacaga gacagttgga ggaggacaga   2580
```

```
ctctcggggc actccctccc gcggtacagc cccctgcgac gactggcgtc ctccgtgttc   2640

tcctcctcca cgctggagac ggagcattac cctcaccccg gcggcggcgg ctcctcgggc   2700

tcctccggtt ccctcattca gcgcagccgc tcggctgaga gcagccctgt gcgggcgccc   2760

caccggcgcc acgcgcccct cgctgctggc aaccacagac tcatgccctc ggtgctccgc   2820

atctcgcggt cccagctgca gcaggtgtgg gcccggttca cccacaagac ctag         2874
```

```
<210> SEQ ID NO 34
<211> LENGTH: 957
<212> TYPE: PRT
<213> ORGANISM: homo sapiens
<220> FEATURE:
<221> NAME/KEY: VARIANT
<222> LOCATION: (1)...(957)
<223> OTHER INFORMATION: Xaa = Any Amino Acid

<400> SEQUENCE: 34

Met Ser Gly Leu Val Leu Met Leu Ala Ala Arg Cys Ile Val Gly Ser
 1               5                  10                  15

Ser Pro Leu Cys Arg Cys Arg Arg Arg Arg Pro Arg Arg Ile Gly Ala
            20                  25                  30

Gly Pro Gly Arg Asp Asp Pro Gly Arg Lys Ala Ala Ala Ala Gly Gly
        35                  40                  45

Ser Gly Ser Pro Asn Ala Ala Leu Ser Arg Pro Arg Pro Ala Pro Ala
    50                  55                  60

Pro Gly Asp Ala Pro Pro Arg Ala Ala Ala Ser Ala Ala Ala Ala Ala
65                  70                  75                  80

Ala Ala Ala Ala Gly Thr Glu Gln Val Asp Gly Pro Leu Arg Ala Gly
                85                  90                  95

Pro Ala Asp Thr Pro Pro Ser Gly Trp Arg Met Gln Cys Leu Ala Ala
            100                 105                 110

Ala Leu Lys Asp Glu Thr Asn Met Ser Gly Gly Gly Glu Gln Ala Asp
        115                 120                 125

Ile Leu Pro Ala Asn Tyr Val Val Lys Asp Arg Trp Lys Val Leu Lys
    130                 135                 140

Lys Ile Gly Gly Gly Gly Phe Gly Glu Ile Tyr Glu Ala Met Asp Leu
145                 150                 155                 160

Leu Thr Arg Glu Asn Val Ala Leu Lys Val Glu Ser Ala Gln Gln Pro
                165                 170                 175

Lys Gln Val Leu Lys Met Glu Val Ala Val Leu Lys Lys Leu Gln Gly
            180                 185                 190

Lys Asp His Val Cys Arg Phe Ile Gly Cys Gly Arg Asn Glu Lys Phe
        195                 200                 205

Asn Tyr Val Val Met Gln Leu Gln Gly Arg Asn Leu Ala Asp Leu Arg
    210                 215                 220

Arg Ser Gln Pro Arg Gly Thr Phe Thr Leu Ser Thr Thr Leu Arg Leu
225                 230                 235                 240

Gly Lys Gln Ile Leu Glu Ser Ile Glu Ala Ile His Ser Val Gly Phe
                245                 250                 255

Leu His Arg Asp Ile Lys Pro Ser Asn Phe Ala Met Gly Arg Leu Pro
            260                 265                 270

Ser Thr Tyr Arg Lys Cys Tyr Met Leu Asp Phe Gly Leu Ala Arg Gln
        275                 280                 285

Tyr Thr Asn Thr Thr Gly Asp Val Arg Pro Pro Arg Asn Val Ala Gly
    290                 295                 300
```

```
Phe Arg Gly Thr Val Arg Tyr Ala Ser Val Asn Ala His Lys Asn Arg
305                 310                 315                 320

Glu Met Gly Arg His Asp Asp Leu Trp Ser Leu Phe Tyr Met Leu Val
                325                 330                 335

Glu Phe Ala Val Gly Gln Leu Pro Trp Arg Lys Ile Lys Asp Lys Glu
            340                 345                 350

Gln Val Gly Met Ile Lys Glu Lys Tyr Glu His Arg Met Leu Leu Lys
        355                 360                 365

His Met Pro Ser Glu Phe His Leu Phe Leu Asp His Ile Ala Ser Leu
    370                 375                 380

Asp Tyr Phe Thr Lys Pro Asp Tyr Gln Leu Ile Met Ser Val Phe Glu
385                 390                 395                 400

Asn Ser Met Lys Glu Arg Gly Ile Ala Glu Asn Glu Ala Phe Asp Trp
                405                 410                 415

Glu Lys Ala Gly Thr Asp Ala Leu Leu Ser Thr Ser Thr Ser Thr Pro
            420                 425                 430

Pro Gln Gln Asn Thr Arg Gln Thr Ala Ala Met Phe Gly Val Val Asn
        435                 440                 445

Val Thr Pro Val Pro Gly Asp Leu Leu Arg Glu Asn Thr Glu Asp Val
    450                 455                 460

Leu Gln Gly Glu His Leu Ser Asp Gln Glu Asn Ala Pro Pro Ile Leu
465                 470                 475                 480

Pro Gly Arg Pro Ser Glu Gly Leu Gly Pro Ser Pro His Leu Val Pro
                485                 490                 495

His Pro Gly Gly Pro Glu Ala Glu Val Trp Glu Glu Thr Asp Val Asn
            500                 505                 510

Arg Asn Lys Leu Arg Ile Asn Ile Gly Lys Val Thr Ala Ala Arg Ala
        515                 520                 525

Lys Gly Val Gly Gly Leu Phe Ser His Pro Arg Phe Pro Ala Leu Cys
    530                 535                 540

Pro Cys Pro Val Pro Pro Lys His Pro Val Pro Gly His Leu Pro Ala
545                 550                 555                 560

Cys Pro Ala Ser Val Ser Arg Ser Leu Pro Ala Leu Ala Ser Leu Cys
                565                 570                 575

Leu Pro Ser Ser Ser Ser Ser Val Ser Phe Thr Leu Arg Arg Pro Ser
            580                 585                 590

Ala His Ser Arg Leu Ile Ser Pro Ser Ser Trp His Ser Pro Leu Leu
        595                 600                 605

Gln Ser Pro Cys Val Glu Glu Glu Gln Ser Arg Gly Met Gly Val Pro
    610                 615                 620

Ser Ser Pro Val Arg Ala Pro Pro Asp Ser Pro Thr Thr Pro Val Arg
625                 630                 635                 640

Ser Leu Arg Tyr Arg Arg Val Asn Ser Pro Glu Ser Glu Arg Leu Ser
                645                 650                 655

Thr Ala Asp Gly Arg Val Glu Leu Pro Glu Arg Arg Ser Arg Met Asp
            660                 665                 670

Leu Pro Gly Ser Pro Ser Arg Gln Ala Cys Ser Ser Gln Pro Ala Gln
        675                 680                 685

Met Leu Ser Val Asp Thr Gly His Ala Asp Arg Gln Ala Ser Gly Arg
    690                 695                 700

Met Asp Val Ser Ala Ser Val Glu Gln Glu Ala Leu Ser Asn Ala Phe
705                 710                 715                 720
```

-continued

```
Arg Ser Val Pro Leu Ala Glu Glu Glu Asp Phe Asp Ser Lys Glu Trp
                725                 730                 735

Val Ile Ile Asp Lys Glu Thr Glu Leu Lys Asp Phe Pro Pro Gly Ala
            740                 745                 750

Glu Pro Ser Thr Ser Gly Thr Thr Asp Glu Glu Pro Glu Glu Leu Arg
        755                 760                 765

Pro Leu Pro Glu Glu Gly Glu Glu Arg Arg Arg Leu Gly Ala Glu Pro
    770                 775                 780

Thr Val Arg Pro Arg Gly Arg Ser Met Gln Ala Leu Ala Glu Glu Asp
785                 790                 795                 800

Leu Gln His Leu Pro Pro Gln Pro Leu Pro Pro Gln Leu Ser Gln Xaa
                805                 810                 815

Asp Gly Arg Ser Glu Thr Ser Gln Pro Pro Thr Pro Gly Ser Pro Ser
            820                 825                 830

His Ser Pro Leu His Ser Gly Pro Arg Pro Arg Arg Arg Glu Ser Asp
        835                 840                 845

Pro Thr Gly Pro Gln Arg Gln Leu Glu Glu Asp Arg Leu Ser Gly His
    850                 855                 860

Ser Leu Pro Arg Tyr Ser Pro Leu Arg Arg Leu Ala Ser Ser Val Phe
865                 870                 875                 880

Ser Ser Ser Thr Leu Glu Thr Glu His Tyr Pro His Pro Gly Gly Gly
                885                 890                 895

Gly Ser Ser Gly Ser Ser Gly Ser Leu Ile Gln Arg Ser Arg Ser Ala
            900                 905                 910

Glu Ser Ser Pro Val Arg Ala Pro His Arg Arg His Ala Pro Leu Ala
        915                 920                 925

Ala Gly Asn His Arg Leu Met Pro Ser Val Leu Arg Ile Ser Arg Ser
    930                 935                 940

Gln Leu Gln Gln Val Trp Ala Arg Phe Thr His Lys Thr
945                 950                 955
```

<210> SEQ ID NO 35
<211> LENGTH: 2856
<212> TYPE: DNA
<213> ORGANISM: homo sapiens

<400> SEQUENCE: 35

```
atgctggcgg cgcggtgcat tgtgggcagc tccccgctct gccgctgccg ccgccgtcgc      60

ccaaggagga tcggggccgg gccgggccgg gatgatccgg gtcggaaggc cgccgccgcc     120

ggagggagcg ggtcacccaa cgccgcactg agccgccccc gccccgcccc ggccccgggg     180

gatgcgccgc cccgagctgc tgcctccgcc gccgccgcag ccgcagccgc agcgggcaca     240

gagcaggtag atggccccct cagggcaggc ccggcggaca cccctccctc tggctggcgg     300

atgcagtgcc tagcggccgc ccttaaggac gaaaccaaca tgagtggggg aggggagcag     360

gccgacatcc tgccggccaa ctacgtggtc aaggatcgct ggaaggtgct gaaaaagatc     420

gggggcgggg gctttggtga gatctacgag gccatggacc tgctgaccag ggagaatgtg     480

gccctcaagg tggagtcagc ccagcagccc aagcaggtcc tcaagatgga ggtggccgtg     540

ctcaagaagt tgcaagggaa ggaccatgtg tgcaggttca ttggctgtgg caggaacgag     600

aagtttaact atgtagtgat gcagctccag ggccggaacc tggccgacct gcgccgtagc     660

cagccgcgag gcaccttcac gctgagcacc acattgcggc tgggcaagca gatcttggag     720

tccatcgagg ccatccactc tgtgggcttc ctgcaccgtg acatcaagcc ttcaaacttt     780
```

-continued

```
gccatgggca ggctgccctc cacctacagg aagtgctata tgctggactt cgggctggcc    840
cggcagtaca ccaacaccac gggggatgtg cggccccctc ggaatgtggc cgggtttcga    900
ggaacggttc gctatgcctc agtcaatgcc cacaagaacc gggagatggg ccgccacgac    960
gacctgtggt ccctcttcta catgctggtg gagtttgcag tgggccagct gccctggagg   1020
aagatcaagg acaaggaaca ggtagggatg atcaaggaga agtatgagca ccggatgctg   1080
ctgaagcaca tgccgtcaga gttccacctc ttcctggacc acattgccag cctcgactac   1140
ttcaccaagc ccgactacca gttgatcatg tcagtgtttg agaacagcat gaaggagagg   1200
ggcattgccg agaatgaggc ctttgactgg gagaaggcag gcaccgatgc cctcctgtcc   1260
acgagcacct ctaccccgcc ccagcagaac acccggcaga cggcagccat gtttggggtg   1320
gtcaatgtga cgccagtgcc tggggacctg ctccgggaga acaccgagga tgtgctacag   1380
ggagagcacc tgagtgacca ggagaatgca cccccaattc tgcccgggag gccctctgag   1440
gggctgggcc ccagtcccca ccttgtcccc caccccgggg gtcctgaggc tgaagtctgg   1500
gaggagacag atgtcaaccg gaacaaactc cggatcaaca tcggcaaagt aactgccgcc   1560
agggcgaagg gcgtgggtgg ccttttctct caccccgat tcccagcctt gtgcccctgc    1620
cctgttcctc ctaagcaccc tgtccccggc catctgcctg cttgccctgc ctctgtttcc   1680
cggtccctcc ccgcactagc ctcgctgtgt cttccatcat catcatcctc tgtctccttc   1740
accctgagga gaccatccgc ccacagccgc ctcatcagcc ccagctcatg gcactcccct   1800
ctcctgcaga gcccctgtgt ggaggaggaa cagagccgag gcatgggggt ccccagctcc   1860
ccagtgcgtg cccccccaga ctcccccaca accccagtcc gttctctgcg ctaccggagg   1920
gtgaacagcc ctgagtcaga aaggctgtcc acggcggacg ggcgagtgga gctacctgag   1980
aggaggtcac ggatggatct gcctggctcg ccctcgcgcc aggcctgctc ctctcagcca   2040
gcccagatgc tgtcagtgga cacaggccac gctgaccgac aggccagtgg ccgcatggay   2100
gtgtcagcct ctgtggagca ggaggccctg agcaacgcct tccgctcggt gccgctggct   2160
gaggaggagg atttcgacag caaagagtgg gtcatcatcg acaaggagac ggagctcaag   2220
gacttccctc caggggctga gcccagcaca tcgggcacca cggatgagga gcccgaggag   2280
ctgcggccac tgcccgagga gggcgaagag cggcggcggc tgggggcaga gcccaccgtc   2340
cggcccgggg gacgcagcat gcaggcgctg gcggaggagg acctgcagca tttgccgccc   2400
cagcccctgc caccccagct gagccaggsc gatggccgtt ccgagacgtc acagcccccc   2460
acgcctggca gcccttccca ctcacccctg cactcgggac cccgccctcg acggagagag   2520
tcggacccca caggcccaca gagacagttg gaggaggaca gactctcggg gcactccctc   2580
ccgcggtaca gcccccctgcg acgactggcg tcctccgtgt tctcctcctc cacgctggag   2640
acggagcatt accctcaccc cggcggcggc ggctcctcgg gctcctccgg ttccctcatt   2700
cagcgcagcc gctcggctga gagcagccct gtgcgggcgc cccaccggcg ccacgcgccc   2760
ctcgctgctg gcaaccacag actcatgccc tcggtgctcc gcatctcgcg gtcccagctg   2820
cagcaggtgt gggcccggtt cacccacaag acctag                              2856
```

<210> SEQ ID NO 36
<211> LENGTH: 951
<212> TYPE: PRT
<213> ORGANISM: homo sapiens
<220> FEATURE:
<221> NAME/KEY: VARIANT
<222> LOCATION: (1)...(951)
<223> OTHER INFORMATION: Xaa = Any Amino Acid

<400> SEQUENCE: 36

```
Met Leu Ala Ala Arg Cys Ile Val Gly Ser Ser Pro Leu Cys Arg Cys
 1               5                  10                  15

Arg Arg Arg Arg Pro Arg Arg Ile Gly Ala Gly Pro Gly Arg Asp Asp
            20                  25                  30

Pro Gly Arg Lys Ala Ala Ala Ala Gly Gly Ser Gly Ser Pro Asn Ala
        35                  40                  45

Ala Leu Ser Arg Pro Arg Pro Ala Pro Ala Pro Gly Asp Ala Pro Pro
    50                  55                  60

Arg Ala Ala Ala Ser Ala Ala Ala Ala Ala Ala Ala Ala Ala Gly Thr
65                  70                  75                  80

Glu Gln Val Asp Gly Pro Leu Arg Ala Gly Pro Ala Asp Thr Pro Pro
                85                  90                  95

Ser Gly Trp Arg Met Gln Cys Leu Ala Ala Ala Leu Lys Asp Glu Thr
            100                 105                 110

Asn Met Ser Gly Gly Gly Glu Gln Ala Asp Ile Leu Pro Ala Asn Tyr
        115                 120                 125

Val Val Lys Asp Arg Trp Lys Val Leu Lys Lys Ile Gly Gly Gly Gly
    130                 135                 140

Phe Gly Glu Ile Tyr Glu Ala Met Asp Leu Leu Thr Arg Glu Asn Val
145                 150                 155                 160

Ala Leu Lys Val Glu Ser Ala Gln Gln Pro Lys Gln Val Leu Lys Met
                165                 170                 175

Glu Val Ala Val Leu Lys Lys Leu Gln Gly Lys Asp His Val Cys Arg
            180                 185                 190

Phe Ile Gly Cys Gly Arg Asn Glu Lys Phe Asn Tyr Val Val Met Gln
        195                 200                 205

Leu Gln Gly Arg Asn Leu Ala Asp Leu Arg Arg Ser Gln Pro Arg Gly
    210                 215                 220

Thr Phe Thr Leu Ser Thr Thr Leu Arg Leu Gly Lys Gln Ile Leu Glu
225                 230                 235                 240

Ser Ile Glu Ala Ile His Ser Val Gly Phe Leu His Arg Asp Ile Lys
                245                 250                 255

Pro Ser Asn Phe Ala Met Gly Arg Leu Pro Ser Thr Tyr Arg Lys Cys
            260                 265                 270

Tyr Met Leu Asp Phe Gly Leu Ala Arg Gln Tyr Thr Asn Thr Thr Gly
        275                 280                 285

Asp Val Arg Pro Pro Arg Asn Val Ala Gly Phe Arg Gly Thr Val Arg
    290                 295                 300

Tyr Ala Ser Val Asn Ala His Lys Asn Arg Glu Met Gly Arg His Asp
305                 310                 315                 320

Asp Leu Trp Ser Leu Phe Tyr Met Leu Val Glu Phe Ala Val Gly Gln
                325                 330                 335

Leu Pro Trp Arg Lys Ile Lys Asp Lys Glu Gln Val Gly Met Ile Lys
            340                 345                 350

Glu Lys Tyr Glu His Arg Met Leu Leu Lys His Met Pro Ser Glu Phe
        355                 360                 365

His Leu Phe Leu Asp His Ile Ala Ser Leu Asp Tyr Phe Thr Lys Pro
    370                 375                 380

Asp Tyr Gln Leu Ile Met Ser Val Phe Glu Asn Ser Met Lys Glu Arg
385                 390                 395                 400

Gly Ile Ala Glu Asn Glu Ala Phe Asp Trp Glu Lys Ala Gly Thr Asp
```

-continued

```
            405                 410                 415

Ala Leu Leu Ser Thr Ser Thr Ser Thr Pro Pro Gln Gln Asn Thr Arg
            420                 425                 430

Gln Thr Ala Ala Met Phe Gly Val Val Asn Val Thr Pro Val Pro Gly
        435                 440                 445

Asp Leu Leu Arg Glu Asn Thr Glu Asp Val Leu Gln Gly Glu His Leu
    450                 455                 460

Ser Asp Gln Glu Asn Ala Pro Pro Ile Leu Pro Gly Arg Pro Ser Glu
465                 470                 475                 480

Gly Leu Gly Pro Ser Pro His Leu Val Pro His Pro Gly Gly Pro Glu
            485                 490                 495

Ala Glu Val Trp Glu Glu Thr Asp Val Asn Arg Asn Lys Leu Arg Ile
            500                 505                 510

Asn Ile Gly Lys Val Thr Ala Ala Arg Ala Lys Gly Val Gly Gly Leu
        515                 520                 525

Phe Ser His Pro Arg Phe Pro Ala Leu Cys Pro Cys Pro Val Pro Pro
    530                 535                 540

Lys His Pro Val Pro Gly His Leu Pro Ala Cys Pro Ala Ser Val Ser
545                 550                 555                 560

Arg Ser Leu Pro Ala Leu Ala Ser Leu Cys Leu Pro Ser Ser Ser Ser
            565                 570                 575

Ser Val Ser Phe Thr Leu Arg Arg Pro Ser Ala His Ser Arg Leu Ile
            580                 585                 590

Ser Pro Ser Ser Trp His Ser Pro Leu Leu Gln Ser Pro Cys Val Glu
        595                 600                 605

Glu Glu Gln Ser Arg Gly Met Gly Val Pro Ser Ser Pro Val Arg Ala
    610                 615                 620

Pro Pro Asp Ser Pro Thr Thr Pro Val Arg Ser Leu Arg Tyr Arg Arg
625                 630                 635                 640

Val Asn Ser Pro Glu Ser Glu Arg Leu Ser Thr Ala Asp Gly Arg Val
            645                 650                 655

Glu Leu Pro Glu Arg Arg Ser Arg Met Asp Leu Pro Gly Ser Pro Ser
            660                 665                 670

Arg Gln Ala Cys Ser Ser Gln Pro Ala Gln Met Leu Ser Val Asp Thr
        675                 680                 685

Gly His Ala Asp Arg Gln Ala Ser Gly Arg Met Asp Val Ser Ala Ser
    690                 695                 700

Val Glu Gln Glu Ala Leu Ser Asn Ala Phe Arg Ser Val Pro Leu Ala
705                 710                 715                 720

Glu Glu Glu Asp Phe Asp Ser Lys Glu Trp Val Ile Ile Asp Lys Glu
            725                 730                 735

Thr Glu Leu Lys Asp Phe Pro Pro Gly Ala Glu Pro Ser Thr Ser Gly
            740                 745                 750

Thr Thr Asp Glu Glu Pro Glu Glu Leu Arg Pro Leu Pro Glu Glu Gly
        755                 760                 765

Glu Glu Arg Arg Arg Leu Gly Ala Glu Pro Thr Val Arg Pro Arg Gly
    770                 775                 780

Arg Ser Met Gln Ala Leu Ala Glu Glu Asp Leu Gln His Leu Pro Pro
785                 790                 795                 800

Gln Pro Leu Pro Pro Gln Leu Ser Gln Xaa Asp Gly Arg Ser Glu Thr
            805                 810                 815

Ser Gln Pro Pro Thr Pro Gly Ser Pro Ser His Ser Pro Leu His Ser
            820                 825                 830
```

-continued

```
Gly Pro Arg Pro Arg Arg Arg Glu Ser Asp Pro Thr Gly Pro Gln Arg
        835                 840                 845

Gln Leu Glu Glu Asp Arg Leu Ser Gly His Ser Leu Pro Arg Tyr Ser
    850                 855                 860

Pro Leu Arg Arg Leu Ala Ser Ser Val Phe Ser Ser Ser Thr Leu Glu
865                 870                 875                 880

Thr Glu His Tyr Pro His Pro Gly Gly Gly Gly Ser Ser Gly Ser Ser
                885                 890                 895

Gly Ser Leu Ile Gln Arg Ser Arg Ser Ala Glu Ser Ser Pro Val Arg
            900                 905                 910

Ala Pro His Arg Arg His Ala Pro Leu Ala Ala Gly Asn His Arg Leu
        915                 920                 925

Met Pro Ser Val Leu Arg Ile Ser Arg Ser Gln Leu Gln Gln Val Trp
    930                 935                 940

Ala Arg Phe Thr His Lys Thr
945                 950
```

<210> SEQ ID NO 37
<211> LENGTH: 2556
<212> TYPE: DNA
<213> ORGANISM: homo sapiens

<400> SEQUENCE: 37

```
atgcagtgcc tagcggccgc ccttaaggac gaaaccaaca tgagtggggg aggggagcag     60

gccgacatcc tgccggccaa ctacgtggtc aaggatcgct ggaaggtgct gaaaaagatc    120

gggggcgggg gctttggtga gatctacgag gccatggacc tgctgaccag ggagaatgtg    180

gccctcaagg tggagtcagc ccagcagccc aagcaggtcc tcaagatgga ggtggccgtg    240

ctcaagaagt tgcaagggaa ggaccatgtg tgcaggttca ttggctgtgg caggaacgag    300

aagtttaact atgtagtgat gcagctccag ggccggaacc tggccgacct gcgccgtagc    360

cagccgcgag gcaccttcac gctgagcacc acattgcggc tgggcaagca gatcttggag    420

tccatcgagg ccatccactc tgtgggcttc ctgcaccgtg acatcaagcc ttcaaacttt    480

gccatgggca ggctgccctc cacctacagg aagtgctata tgctggactt cgggctggcc    540

cggcagtaca ccaacaccac gggggatgtg cggccccctc ggaatgtggc cgggtttcga    600

ggaacggttc gctatgcctc agtcaatgcc cacaagaacc gggagatggg ccgccacgac    660

gacctgtggt ccctcttcta catgctggtg gagtttgcag tgggccagct gccctggagg    720

aagatcaagg acaaggaaca ggtagggatg atcaaggaga agtatgagca ccggatgctg    780

ctgaagcaca tgccgtcaga gttccacctc ttcctggacc acattgccag cctcgactac    840

ttcaccaagc ccgactacca gttgatcatg tcagtgtttg agaacagcat gaaggagagg    900

ggcattgccg agaatgaggc ctttgactgg gagaaggcag gcaccgatgc cctcctgtcc    960

acgagcacct ctaccccgcc ccagcagaac acccggcaga cggcagccat gtttggggtg   1020

gtcaatgtga cgccagtgcc tggggacctg ctccgggaga acaccgagga tgtgctacag   1080

ggagagcacc tgagtgacca ggagaatgca cccccaattc tgcccgggag gccctctgag   1140

gggctgggcc ccagtcccca ccttgtcccc caccccgggg gtcctgaggc tgaagtctgg   1200

gaggagacag atgtcaaccg gaacaaactc cggatcaaca tcggcaaagt aactgccgcc   1260

agggcgaagg gcgtgggtgg ccttttctct cacccccgat tcccagcctt gtgcccctgc   1320

cctgttcctc ctaagcaccc tgtccccggc catctgcctg cttgccctgc ctctgtttcc   1380
```

-continued

```
cggtccctcc ccgcactagc ctcgctgtgt cttccatcat catcatcctc tgtctccttc   1440

accctgagga gaccatccgc ccacagccgc ctcatcagcc ccagctcatg gcactcccct   1500

ctcctgcaga gcccctgtgt ggaggaggaa cagagccgag gcatgggggt ccccagctcc   1560

ccagtgcgtg cccccccaga ctcccccaca accccagtcc gttctctgcg ctaccggagg   1620

gtgaacagcc ctgagtcaga aaggctgtcc acggcggacg ggcgagtgga gctacctgag   1680

aggaggtcac ggatggatct gcctggctcg ccctcgcgcc aggcctgctc ctctcagcca   1740

gcccagatgc tgtcagtgga cacaggccac gctgaccgac aggccagtgg ccgcatggay   1800

gtgtcagcct ctgtggagca ggaggccctg agcaacgcct tccgctcggt gccgctggct   1860

gaggaggagg atttcgacag caaagagtgg gtcatcatcg acaaggagac ggagctcaag   1920

gacttccctc caggggctga gcccagcaca tcgggcacca cggatgagga gcccgaggag   1980

ctgcggccac tgcccgagga gggcgaagag cggcggcggc tgggggcaga gcccaccgtc   2040

cggccccggg gacgcagcat gcaggcgctg gcggaggagg acctgcagca tttgccgccc   2100

cagcccctgc caccccagct gagccaggsc gatggccgtt ccgagacgtc acagcccccc   2160

acgcctggca gcccttccca ctcacccctg cactcgggac cccgccctcg acggagagag   2220

tcggacccca caggcccaca gagacagttg gaggaggaca gactctcggg gcactccctc   2280

ccgcggtaca gcccccctgcg acgactggcg tcctccgtgt tctcctcctc cacgctggag   2340

acggagcatt accctcaccc cggcggcggc ggctcctcgg gctcctccgg ttccctcatt   2400

cagcgcagcc gctcggctga gagcagccct gtgcgggcgc cccaccggcg ccacgcgccc   2460

ctcgctgctg gcaaccacag actcatgccc tcggtgctcc gcatctcgcg gtcccagctg   2520

cagcaggtgt gggcccggtt cacccacaag acctag                               2556
```

<210> SEQ ID NO 38
<211> LENGTH: 851
<212> TYPE: PRT
<213> ORGANISM: homo sapiens
<220> FEATURE:
<221> NAME/KEY: VARIANT
<222> LOCATION: (1)...(851)
<223> OTHER INFORMATION: Xaa = Any Amino Acid

<400> SEQUENCE: 38

```
Met Gln Cys Leu Ala Ala Ala Leu Lys Asp Glu Thr Asn Met Ser Gly
 1               5                  10                  15

Gly Gly Glu Gln Ala Asp Ile Leu Pro Ala Asn Tyr Val Val Lys Asp
            20                  25                  30

Arg Trp Lys Val Leu Lys Lys Ile Gly Gly Gly Gly Phe Gly Glu Ile
        35                  40                  45

Tyr Glu Ala Met Asp Leu Leu Thr Arg Glu Asn Val Ala Leu Lys Val
    50                  55                  60

Glu Ser Ala Gln Gln Pro Lys Gln Val Leu Lys Met Glu Val Ala Val
65                  70                  75                  80

Leu Lys Lys Leu Gln Gly Lys Asp His Val Cys Arg Phe Ile Gly Cys
                85                  90                  95

Gly Arg Asn Glu Lys Phe Asn Tyr Val Val Met Gln Leu Gln Gly Arg
            100                 105                 110

Asn Leu Ala Asp Leu Arg Arg Ser Gln Pro Arg Gly Thr Phe Thr Leu
        115                 120                 125

Ser Thr Thr Leu Arg Leu Gly Lys Gln Ile Leu Glu Ser Ile Glu Ala
    130                 135                 140
```

-continued

```
Ile His Ser Val Gly Phe Leu His Arg Asp Ile Lys Pro Ser Asn Phe
145                 150                 155                 160

Ala Met Gly Arg Leu Pro Ser Thr Tyr Arg Lys Cys Tyr Met Leu Asp
                165                 170                 175

Phe Gly Leu Ala Arg Gln Tyr Thr Asn Thr Thr Gly Asp Val Arg Pro
            180                 185                 190

Pro Arg Asn Val Ala Gly Phe Arg Gly Thr Val Arg Tyr Ala Ser Val
        195                 200                 205

Asn Ala His Lys Asn Arg Glu Met Gly Arg His Asp Asp Leu Trp Ser
    210                 215                 220

Leu Phe Tyr Met Leu Val Glu Phe Ala Val Gly Gln Leu Pro Trp Arg
225                 230                 235                 240

Lys Ile Lys Asp Lys Glu Gln Val Gly Met Ile Lys Glu Lys Tyr Glu
                245                 250                 255

His Arg Met Leu Leu Lys His Met Pro Ser Glu Phe His Leu Phe Leu
            260                 265                 270

Asp His Ile Ala Ser Leu Asp Tyr Phe Thr Lys Pro Asp Tyr Gln Leu
        275                 280                 285

Ile Met Ser Val Phe Glu Asn Ser Met Lys Glu Arg Gly Ile Ala Glu
    290                 295                 300

Asn Glu Ala Phe Asp Trp Glu Lys Ala Gly Thr Asp Ala Leu Leu Ser
305                 310                 315                 320

Thr Ser Thr Ser Thr Pro Pro Gln Gln Asn Thr Arg Gln Thr Ala Ala
                325                 330                 335

Met Phe Gly Val Val Asn Val Thr Pro Val Pro Gly Asp Leu Leu Arg
            340                 345                 350

Glu Asn Thr Glu Asp Val Leu Gln Gly Glu His Leu Ser Asp Gln Glu
        355                 360                 365

Asn Ala Pro Pro Ile Leu Pro Gly Arg Pro Ser Glu Gly Leu Gly Pro
    370                 375                 380

Ser Pro His Leu Val Pro His Pro Gly Gly Pro Glu Ala Glu Val Trp
385                 390                 395                 400

Glu Glu Thr Asp Val Asn Arg Asn Lys Leu Arg Ile Asn Ile Gly Lys
                405                 410                 415

Val Thr Ala Ala Arg Ala Lys Gly Val Gly Gly Leu Phe Ser His Pro
            420                 425                 430

Arg Phe Pro Ala Leu Cys Pro Cys Pro Val Pro Pro Lys His Pro Val
        435                 440                 445

Pro Gly His Leu Pro Ala Cys Pro Ala Ser Val Ser Arg Ser Leu Pro
    450                 455                 460

Ala Leu Ala Ser Leu Cys Leu Pro Ser Ser Ser Ser Ser Val Ser Phe
465                 470                 475                 480

Thr Leu Arg Arg Pro Ser Ala His Ser Arg Leu Ile Ser Pro Ser Ser
                485                 490                 495

Trp His Ser Pro Leu Leu Gln Ser Pro Cys Val Glu Glu Glu Gln Ser
            500                 505                 510

Arg Gly Met Gly Val Pro Ser Ser Pro Val Arg Ala Pro Pro Asp Ser
        515                 520                 525

Pro Thr Thr Pro Val Arg Ser Leu Arg Tyr Arg Arg Val Asn Ser Pro
    530                 535                 540

Glu Ser Glu Arg Leu Ser Thr Ala Asp Gly Arg Val Glu Leu Pro Glu
545                 550                 555                 560

Arg Arg Ser Arg Met Asp Leu Pro Gly Ser Pro Ser Arg Gln Ala Cys
```

-continued

```
                565                 570                 575

Ser Ser Gln Pro Ala Gln Met Leu Ser Val Asp Thr Gly His Ala Asp
            580                 585                 590

Arg Gln Ala Ser Gly Arg Met Asp Val Ser Ala Ser Val Glu Gln Glu
        595                 600                 605

Ala Leu Ser Asn Ala Phe Arg Ser Val Pro Leu Ala Glu Glu Glu Asp
    610                 615                 620

Phe Asp Ser Lys Glu Trp Val Ile Ile Asp Lys Glu Thr Glu Leu Lys
625                 630                 635                 640

Asp Phe Pro Pro Gly Ala Glu Pro Ser Thr Ser Gly Thr Thr Asp Glu
                645                 650                 655

Glu Pro Glu Glu Leu Arg Pro Leu Pro Glu Glu Gly Glu Glu Arg Arg
            660                 665                 670

Arg Leu Gly Ala Glu Pro Thr Val Arg Pro Arg Gly Arg Ser Met Gln
        675                 680                 685

Ala Leu Ala Glu Glu Asp Leu Gln His Leu Pro Pro Gln Pro Leu Pro
    690                 695                 700

Pro Gln Leu Ser Gln Xaa Asp Gly Arg Ser Glu Thr Ser Gln Pro Pro
705                 710                 715                 720

Thr Pro Gly Ser Pro Ser His Ser Pro Leu His Ser Gly Pro Arg Pro
                725                 730                 735

Arg Arg Arg Glu Ser Asp Pro Thr Gly Pro Gln Arg Gln Leu Glu Glu
            740                 745                 750

Asp Arg Leu Ser Gly His Ser Leu Pro Arg Tyr Ser Pro Leu Arg Arg
        755                 760                 765

Leu Ala Ser Ser Val Phe Ser Ser Ser Thr Leu Glu Thr Glu His Tyr
    770                 775                 780

Pro His Pro Gly Gly Gly Gly Ser Ser Gly Ser Ser Gly Ser Leu Ile
785                 790                 795                 800

Gln Arg Ser Arg Ser Ala Glu Ser Ser Pro Val Arg Ala Pro His Arg
                805                 810                 815

Arg His Ala Pro Leu Ala Ala Gly Asn His Arg Leu Met Pro Ser Val
            820                 825                 830

Leu Arg Ile Ser Arg Ser Gln Leu Gln Gln Val Trp Ala Arg Phe Thr
        835                 840                 845

His Lys Thr
    850
```

<210> SEQ ID NO 39
<211> LENGTH: 2517
<212> TYPE: DNA
<213> ORGANISM: homo sapiens

<400> SEQUENCE: 39

```
atgagtgggg gaggggagca ggccgacatc ctgccggcca actacgtggt caaggatcgc      60

tggaaggtgc tgaaaaagat cgggggcggg ggctttggtg agatctacga ggccatggac     120

ctgctgacca gggagaatgt ggccctcaag gtggagtcag cccagcagcc caagcaggtc     180

ctcaagatgg aggtggccgt gctcaagaag ttgcaaggga aggaccatgt gtgcaggttc     240

attggctgtg gcaggaacga gaagtttaac tatgtagtga tgcagctcca gggccggaac     300

ctggccgacc tgcgccgtag ccagccgcga ggcaccttca cgctgagcac cacattgcgg     360

ctgggcaagc agatcttgga gtccatcgag gccatccact ctgtgggctt cctgcaccgt     420

gacatcaagc cttcaaactt tgccatgggc aggctgccct ccacctacag gaagtgctat     480
```

-continued

```
atgctggact tcgggctggc ccggcagtac accaacacca cgggggatgt gcggccccct    540
cggaatgtgg ccgggtttcg aggaacggtt cgctatgcct cagtcaatgc ccacaagaac    600
cgggagatgg gccgccacga cgacctgtgg tccctcttct acatgctggt ggagtttgca    660
gtgggccagc tgccctggag gaagatcaag gacaaggaac aggtagggat gatcaaggag    720
aagtatgagc accggatgct gctgaagcac atgccgtcag agttccacct cttcctggac    780
cacattgcca gcctcgacta cttcaccaag cccgactacc agttgatcat gtcagtgttt    840
gagaacagca tgaaggagag ggcattgcc gagaatgagg cctttgactg ggagaaggca    900
ggcaccgatg ccctcctgtc cacgagcacc tctaccccgc cccagcagaa cacccggcag    960
acggcagcca tgtttggggt ggtcaatgtg acgccagtgc ctggggacct gctccgggag   1020
aacaccgagg atgtgctaca gggagagcac ctgagtgacc aggagaatgc acccccaatt   1080
ctgcccggga ggccctctga ggggctgggc cccagtcccc accttgtccc ccaccccggg   1140
ggtcctgagg ctgaagtctg ggaggagaca gatgtcaacc ggaacaaact ccggatcaac   1200
atcggcaaag taactgccgc cagggcgaag ggcgtgggtg gccttttctc tcacccccga   1260
ttcccagcct tgtgcccctg ccctgttcct cctaagcacc ctgtccccgg ccatctgcct   1320
gcttgccctg cctctgtttc ccggtccctc cccgcactag cctcgctgtg tcttccatca   1380
tcatcatcct ctgtctcctt caccctgagg agaccatccg cccacagccg cctcatcagc   1440
cccagctcat ggcactcccc tctcctgcag agcccctgtg tggaggagga acagagccga   1500
ggcatggggg tccccagctc cccagtgcgt gcccccccag actcccccac aaccccagtc   1560
cgttctctgc gctaccggag ggtgaacagc cctgagtcag aaaggctgtc cacggcggac   1620
gggcgagtgg agctacctga gaggaggtca cggatggatc tgcctggctc gccctcgcgc   1680
caggcctgct cctctcagcc agcccagatg ctgtcagtgg acacaggcca cgctgaccga   1740
caggccagtg gccgcatgga ygtgtcagcc tctgtggagc aggaggccct gagcaacgcc   1800
ttccgctcgg tgccgctggc tgaggaggag gatttcgaca gcaaagagtg ggtcatcatc   1860
gacaaggaga cggagctcaa ggacttccct ccaggggctg agcccagcac atcgggcacc   1920
acggatgagg agcccgagga gctgcggcca ctgcccgagg agggcgaaga gcggcggcgg   1980
ctgggggcag agcccaccgt ccggccccgg ggacgcagca tgcaggcgct ggcggaggag   2040
gacctgcagc atttgccgcc ccagcccctg ccaccccagc tgagccaggs cgatggccgt   2100
tccgagacgt cacagccccc cacgcctggc agcccttccc actcacccct gcactcggga   2160
ccccgccctc gacggagaga gtcggacccc acaggcccac agagacagtt ggaggaggac   2220
agactctcgg ggcactccct cccgcggtac agcccccctgc gacgactggc gtcctccgtg   2280
ttctcctcct ccacgctgga gacggagcat taccctcacc ccggcggcgg cggctcctcg   2340
ggctcctccg gttccctcat tcagcgcagc cgctcggctg agagcagccc tgtgcgggcg   2400
ccccaccggc gccacgcgcc cctcgctgct ggcaaccaca gactcatgcc ctcggtgctc   2460
cgcatctcgc ggtcccagct gcagcaggtg tgggcccggt tcacccacaa gacctag      2517
```

<210> SEQ ID NO 40
<211> LENGTH: 838
<212> TYPE: PRT
<213> ORGANISM: homo sapiens
<220> FEATURE:
<221> NAME/KEY: VARIANT
<222> LOCATION: (1)...(838)
<223> OTHER INFORMATION: Xaa = Any Amino Acid -continued

<400> SEQUENCE: 40

```
Met Ser Gly Gly Gly Glu Gln Ala Asp Ile Leu Pro Ala Asn Tyr Val
 1               5                  10                  15

Val Lys Asp Arg Trp Lys Val Leu Lys Lys Ile Gly Gly Gly Gly Phe
            20                  25                  30

Gly Glu Ile Tyr Glu Ala Met Asp Leu Leu Thr Arg Glu Asn Val Ala
        35                  40                  45

Leu Lys Val Glu Ser Ala Gln Gln Pro Lys Gln Val Leu Lys Met Glu
    50                  55                  60

Val Ala Val Leu Lys Lys Leu Gln Gly Lys Asp His Val Cys Arg Phe
65                  70                  75                  80

Ile Gly Cys Gly Arg Asn Glu Lys Phe Asn Tyr Val Val Met Gln Leu
                85                  90                  95

Gln Gly Arg Asn Leu Ala Asp Leu Arg Arg Ser Gln Pro Arg Gly Thr
            100                 105                 110

Phe Thr Leu Ser Thr Thr Leu Arg Leu Gly Lys Gln Ile Leu Glu Ser
        115                 120                 125

Ile Glu Ala Ile His Ser Val Gly Phe Leu His Arg Asp Ile Lys Pro
    130                 135                 140

Ser Asn Phe Ala Met Gly Arg Leu Pro Ser Thr Tyr Arg Lys Cys Tyr
145                 150                 155                 160

Met Leu Asp Phe Gly Leu Ala Arg Gln Tyr Thr Asn Thr Thr Gly Asp
                165                 170                 175

Val Arg Pro Pro Arg Asn Val Ala Gly Phe Arg Gly Thr Val Arg Tyr
            180                 185                 190

Ala Ser Val Asn Ala His Lys Asn Arg Glu Met Gly Arg His Asp Asp
        195                 200                 205

Leu Trp Ser Leu Phe Tyr Met Leu Val Glu Phe Ala Val Gly Gln Leu
    210                 215                 220

Pro Trp Arg Lys Ile Lys Asp Lys Glu Gln Val Gly Met Ile Lys Glu
225                 230                 235                 240

Lys Tyr Glu His Arg Met Leu Leu Lys His Met Pro Ser Glu Phe His
                245                 250                 255

Leu Phe Leu Asp His Ile Ala Ser Leu Asp Tyr Phe Thr Lys Pro Asp
            260                 265                 270

Tyr Gln Leu Ile Met Ser Val Phe Glu Asn Ser Met Lys Glu Arg Gly
        275                 280                 285

Ile Ala Glu Asn Glu Ala Phe Asp Trp Glu Lys Ala Gly Thr Asp Ala
    290                 295                 300

Leu Leu Ser Thr Ser Thr Ser Thr Pro Pro Gln Gln Asn Thr Arg Gln
305                 310                 315                 320

Thr Ala Ala Met Phe Gly Val Val Asn Val Thr Pro Val Pro Gly Asp
                325                 330                 335

Leu Leu Arg Glu Asn Thr Glu Asp Val Leu Gln Gly Glu His Leu Ser
            340                 345                 350

Asp Gln Glu Asn Ala Pro Pro Ile Leu Pro Gly Arg Pro Ser Glu Gly
        355                 360                 365

Leu Gly Pro Ser Pro His Leu Val Pro His Pro Gly Gly Pro Glu Ala
    370                 375                 380

Glu Val Trp Glu Glu Thr Asp Val Asn Arg Asn Lys Leu Arg Ile Asn
385                 390                 395                 400

Ile Gly Lys Val Thr Ala Ala Arg Ala Lys Gly Val Gly Gly Leu Phe
                405                 410                 415
```

-continued

```
Ser His Pro Arg Phe Pro Ala Leu Cys Pro Cys Pro Val Pro Pro Lys
        420                 425                 430

His Pro Val Pro Gly His Leu Pro Ala Cys Pro Ala Ser Val Ser Arg
        435                 440                 445

Ser Leu Pro Ala Leu Ala Ser Leu Cys Leu Pro Ser Ser Ser Ser Ser
    450                 455                 460

Val Ser Phe Thr Leu Arg Arg Pro Ser Ala His Ser Arg Leu Ile Ser
465                 470                 475                 480

Pro Ser Ser Trp His Ser Pro Leu Leu Gln Ser Pro Cys Val Glu Glu
                485                 490                 495

Glu Gln Ser Arg Gly Met Gly Val Pro Ser Ser Pro Val Arg Ala Pro
            500                 505                 510

Pro Asp Ser Pro Thr Thr Pro Val Arg Ser Leu Arg Tyr Arg Arg Val
        515                 520                 525

Asn Ser Pro Glu Ser Glu Arg Leu Ser Thr Ala Asp Gly Arg Val Glu
    530                 535                 540

Leu Pro Glu Arg Arg Ser Arg Met Asp Leu Pro Gly Ser Pro Ser Arg
545                 550                 555                 560

Gln Ala Cys Ser Ser Gln Pro Ala Gln Met Leu Ser Val Asp Thr Gly
                565                 570                 575

His Ala Asp Arg Gln Ala Ser Gly Arg Met Asp Val Ser Ala Ser Val
            580                 585                 590

Glu Gln Glu Ala Leu Ser Asn Ala Phe Arg Ser Val Pro Leu Ala Glu
        595                 600                 605

Glu Glu Asp Phe Asp Ser Lys Glu Trp Val Ile Ile Asp Lys Glu Thr
    610                 615                 620

Glu Leu Lys Asp Phe Pro Pro Gly Ala Glu Pro Ser Thr Ser Gly Thr
625                 630                 635                 640

Thr Asp Glu Glu Pro Glu Glu Leu Arg Pro Leu Pro Glu Glu Gly Glu
                645                 650                 655

Glu Arg Arg Arg Leu Gly Ala Glu Pro Thr Val Arg Pro Arg Gly Arg
            660                 665                 670

Ser Met Gln Ala Leu Ala Glu Glu Asp Leu Gln His Leu Pro Pro Gln
        675                 680                 685

Pro Leu Pro Pro Gln Leu Ser Gln Xaa Asp Gly Arg Ser Glu Thr Ser
    690                 695                 700

Gln Pro Pro Thr Pro Gly Ser Pro Ser His Ser Pro Leu His Ser Gly
705                 710                 715                 720

Pro Arg Pro Arg Arg Arg Glu Ser Asp Pro Thr Gly Pro Gln Arg Gln
                725                 730                 735

Leu Glu Glu Asp Arg Leu Ser Gly His Ser Leu Pro Arg Tyr Ser Pro
            740                 745                 750

Leu Arg Arg Leu Ala Ser Ser Val Phe Ser Ser Ser Thr Leu Glu Thr
        755                 760                 765

Glu His Tyr Pro His Pro Gly Gly Gly Gly Ser Ser Gly Ser Ser Gly
    770                 775                 780

Ser Leu Ile Gln Arg Ser Arg Ser Ala Glu Ser Ser Pro Val Arg Ala
785                 790                 795                 800

Pro His Arg Arg His Ala Pro Leu Ala Ala Gly Asn His Arg Leu Met
                805                 810                 815
```

-continued

```
Pro Ser Val Leu Arg Ile Ser Arg Ser Gln Leu Gln Gln Val Trp Ala
            820                 825                 830

Arg Phe Thr His Lys Thr
        835
```